United States Patent
Lac et al.

(10) Patent No.: US 10,588,982 B2
(45) Date of Patent: Mar. 17, 2020

(54) SITE-SPECIFIC COVALENT CHEMICAL LIGATION TO MONOCLONAL AND POLYCLONAL IMMUNOGLOBULIN

(71) Applicant: The Regents of the University of California, Oakland, CA (US)

(72) Inventors: Diana Lac, Oakland, CA (US); Chun Feng, Oakland, CA (US); Gaurav Bhardwaj, Oakland, CA (US); Siddarth Chandrasekaran, Oakland, CA (US); Kit S. Lam, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/727,490

(22) Filed: Oct. 6, 2017

(65) Prior Publication Data

US 2018/0140715 A1  May 24, 2018

Related U.S. Application Data

(63) Continuation of application No. PCT/US2016/026816, filed on Apr. 8, 2016.

(60) Provisional application No. 62/144,710, filed on Apr. 8, 2015.

(51) Int. Cl.

| | |
|---|---|
| *A61K 47/65* | (2017.01) |
| *C07D 495/04* | (2006.01) |
| *C07D 403/12* | (2006.01) |
| *A61K 47/68* | (2017.01) |

(52) U.S. Cl.
CPC .......... *A61K 47/65* (2017.08); *A61K 47/6803* (2017.08); *A61K 47/6845* (2017.08); *A61K 47/6849* (2017.08); *A61K 47/6855* (2017.08); *A61K 47/6867* (2017.08); *C07D 403/12* (2013.01); *C07D 495/04* (2013.01)

(58) Field of Classification Search
CPC ................ A61K 47/65; A61K 47/6845; A61K 47/6867; A61K 47/6803; A61K 47/6849; A61K 47/6855; C07D 403/12; C07D 495/04
USPC ....................................................... 548/400
See application file for complete search history.

(56) References Cited

FOREIGN PATENT DOCUMENTS

| WO | 2013068874 A1 | 5/2013 |
|---|---|---|
| WO | 2013103707 A1 | 7/2013 |
| WO | 2016164843 A1 | 10/2016 |

OTHER PUBLICATIONS

Doronina, Enhance Activity of Monomethylauristatin F through Monoclonal Antibody Delivery: Effects of Linker Technology and Toxicity, Bioconjugate Chem, 17, 114-124, 2006.
International Search Report for International Application No. PCT/US2016/026816 dated Jul. 5, 2016.
Handlogten et al., Design of a Heterobivalent Ligand to Inhibit IgE Clustering on Mast Cells, Chemistry & Biology 18, 1179-1188, Sep. 23, 2011.
Lac et al., Covalent chemical ligation strategy for monclonal and polyclonal immununoglobulins at the nucleotide binding sites. Bioconjugate Chem., 17(1), 159-169; 2016.

*Primary Examiner* — Kristin A Vajda

(74) *Attorney, Agent, or Firm* — Mintz, Levin, Cohn, Ferris, Glovsky and Popeo, P.C.

(57) ABSTRACT

Methods and compositions are described herein for covalently linking an antibody to a molecular payload. Compositions are described herein containing an antibody covalently linked to a molecular payload.

21 Claims, 35 Drawing Sheets

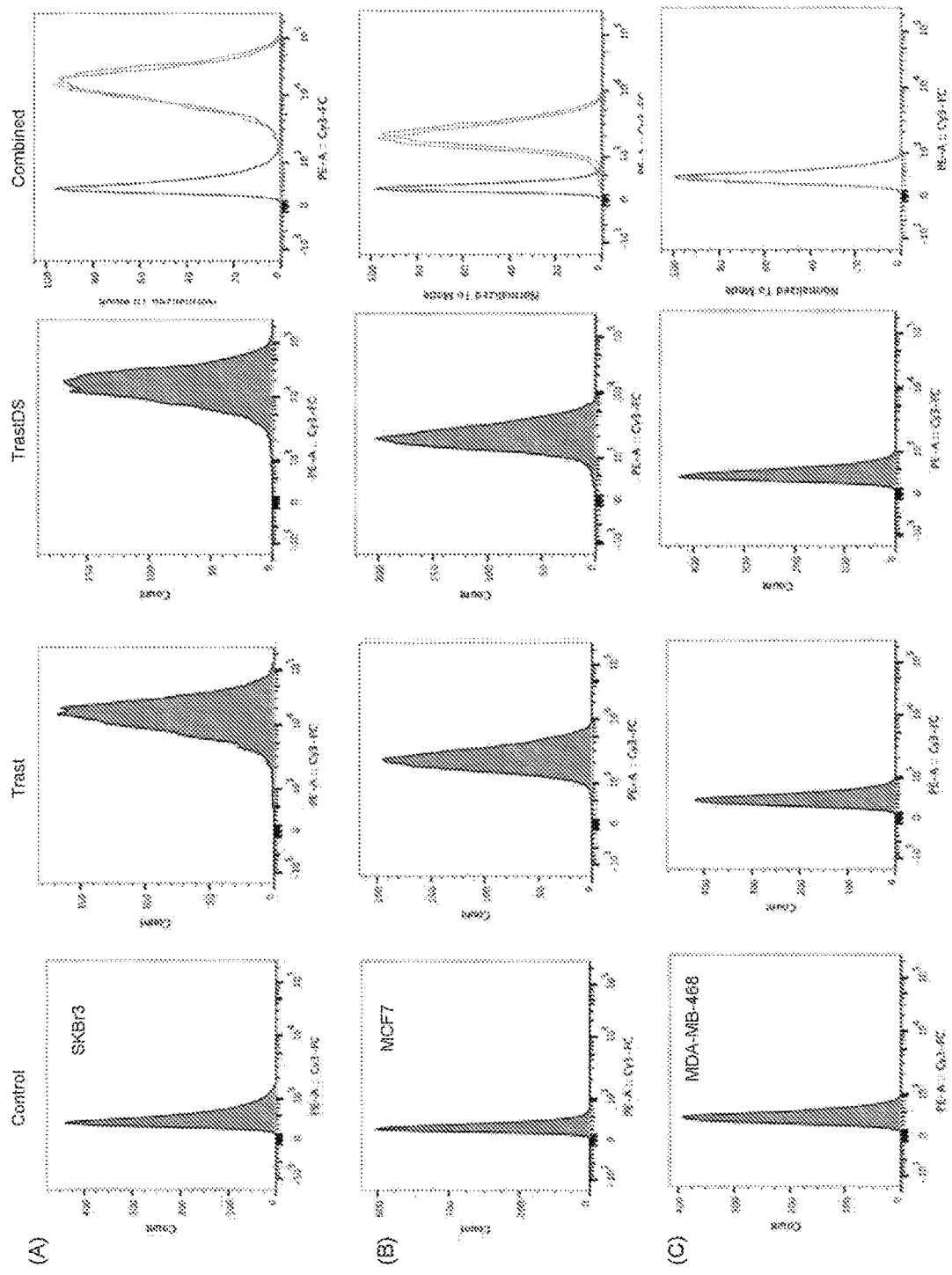

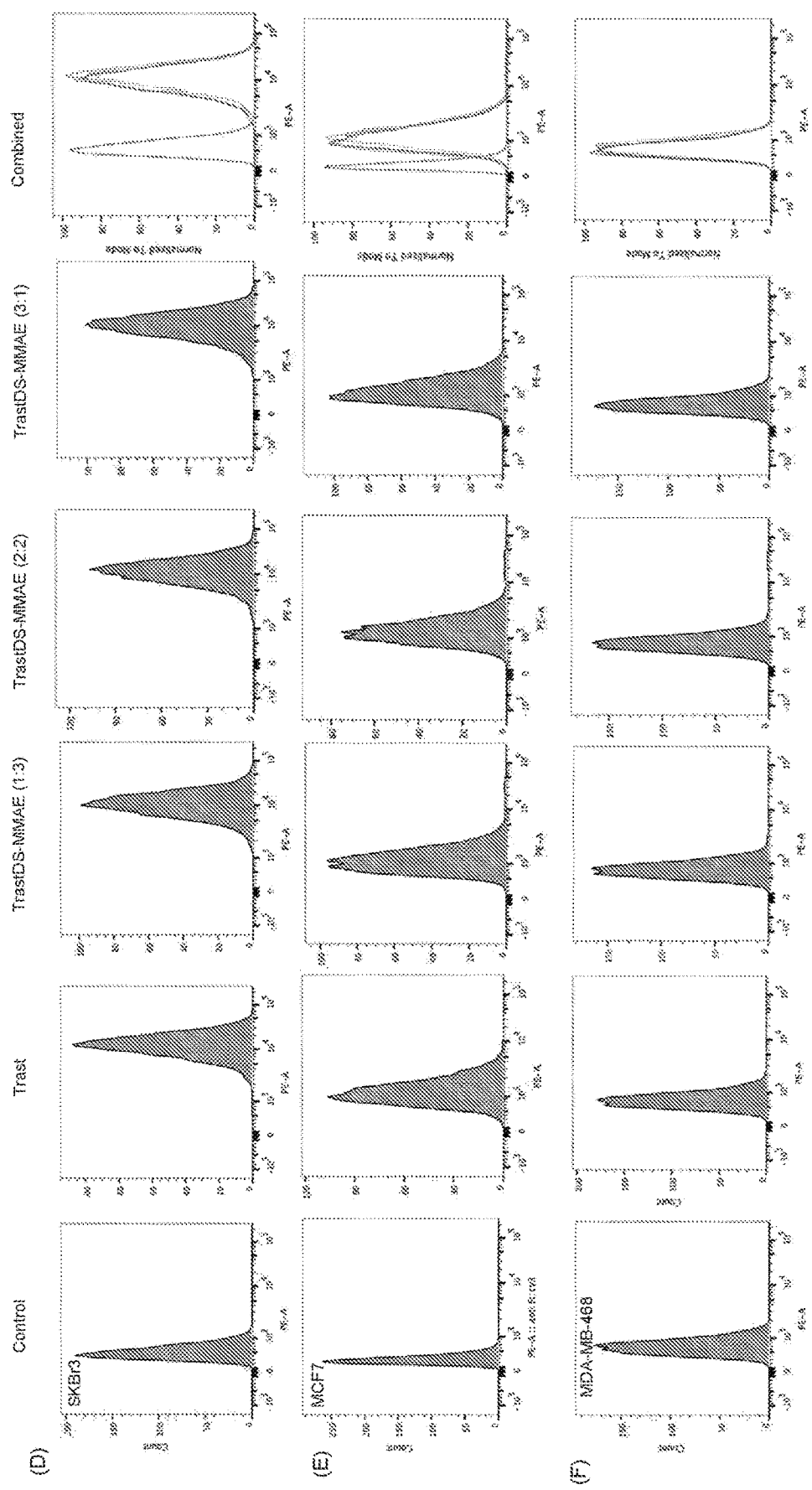
Figure 9-Cont.

Figure 12-Cont.
Indole-peg linker – K(acrylic acid) 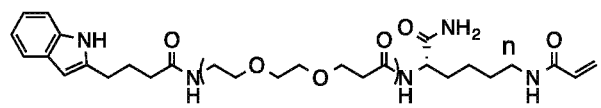
Indole – K(acrylic acid) [α-amine] 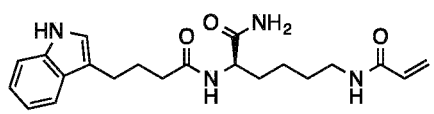
Indole – K(acrylic acid) [ε-amine] 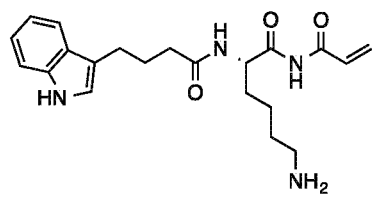
Indole – Pro – K(acrylic acid) 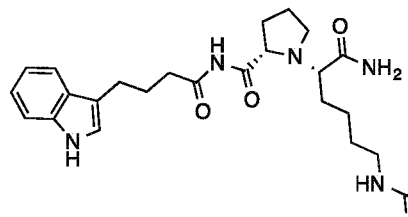
Indole – Pro – Gly – K(acrylic acid) 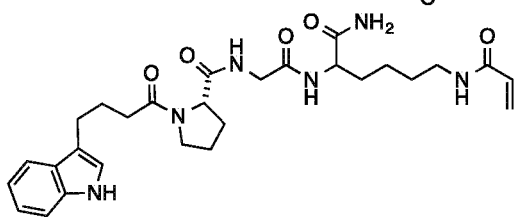
Indole – Gly – K(acrylic acid) 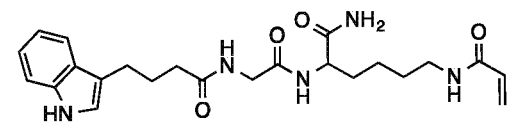
Indole – Gly – Glu – K(acrylic acid) 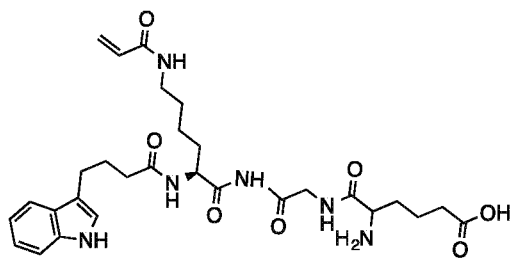

Figure 20
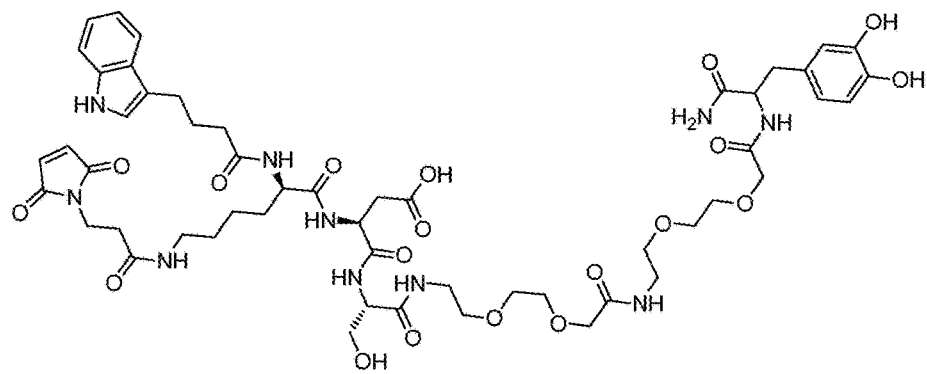
Chemical Formula: $C_{53}H_{72}N_{10}O_{19}$
Exact Mass: 1152.4975
Molecular Weight: 1153.1944
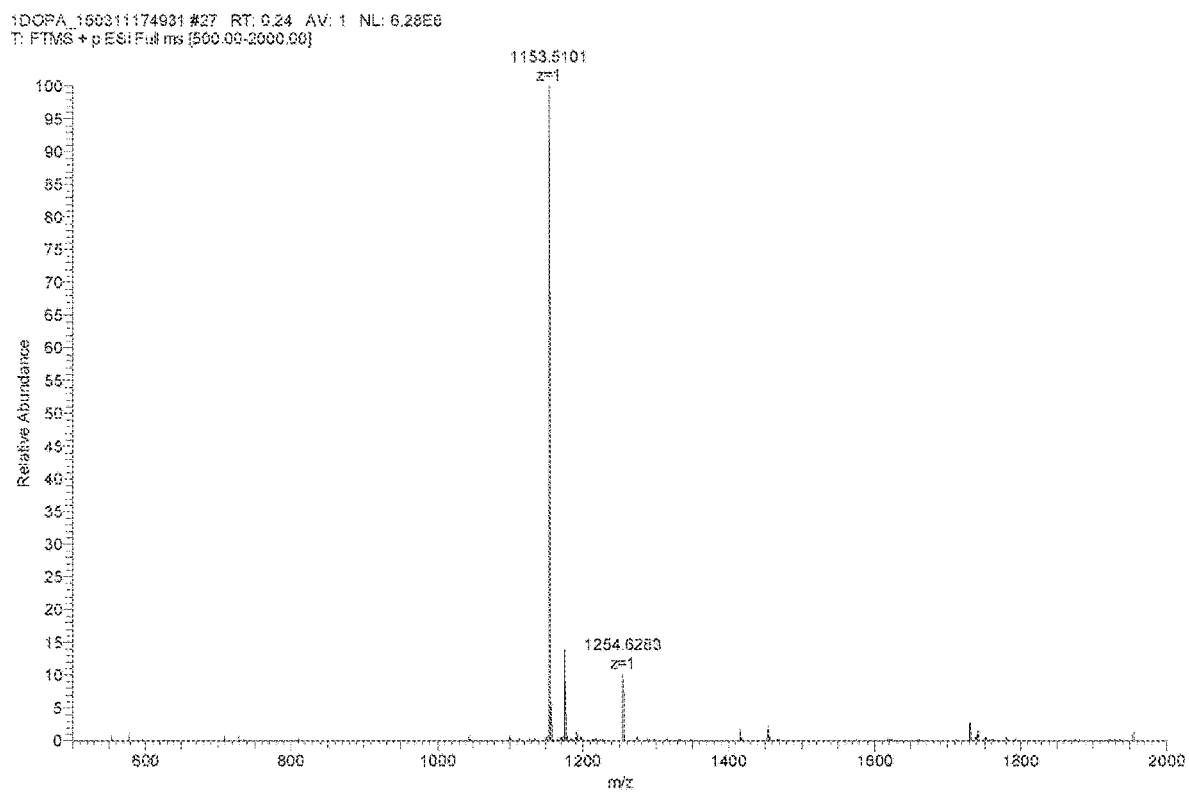

Figure 22
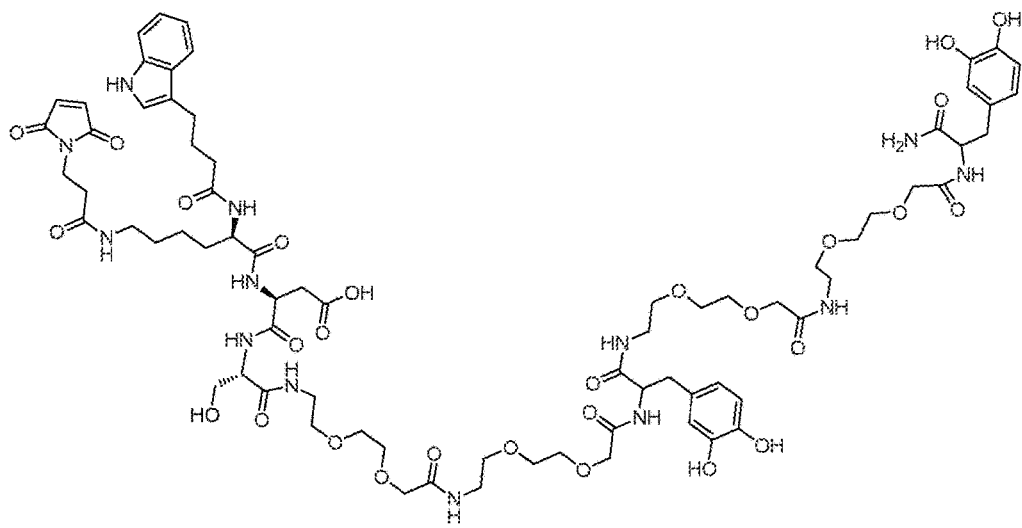
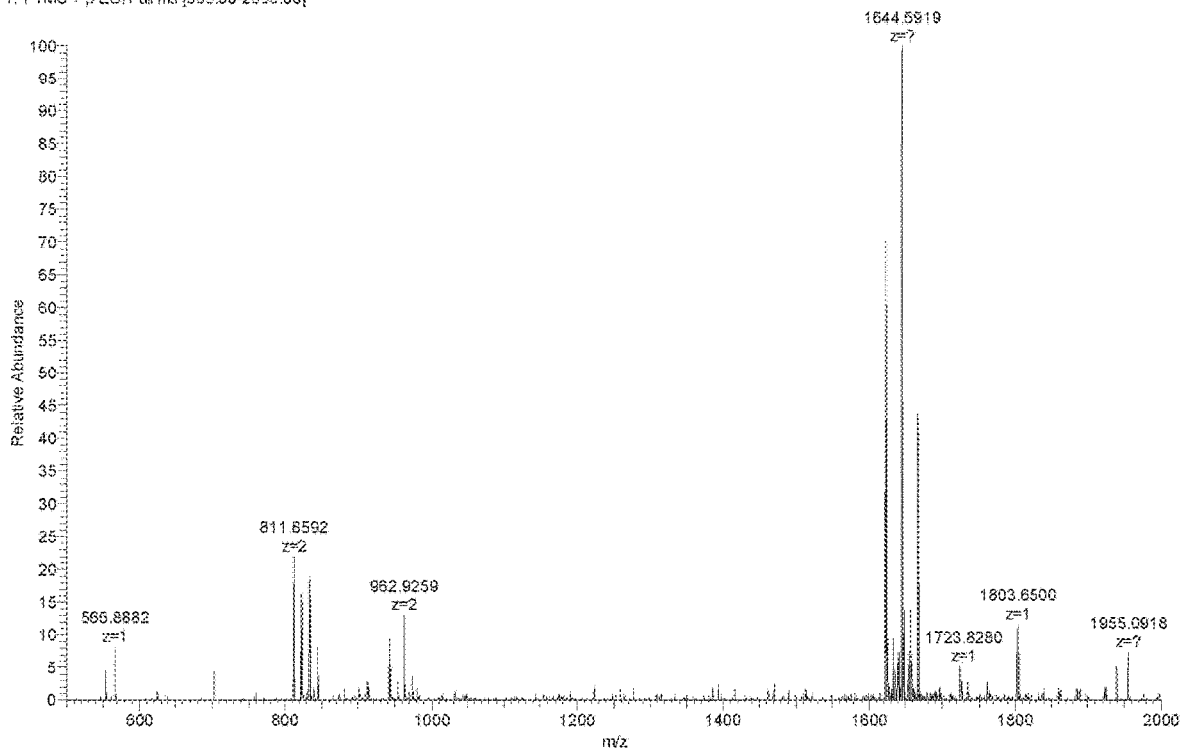

Figure 29
Picture 1
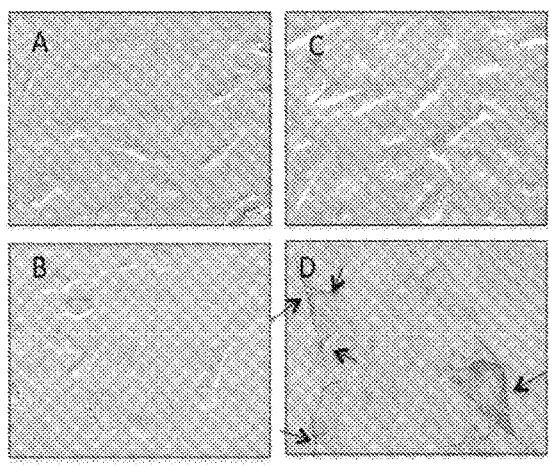
Picture 2
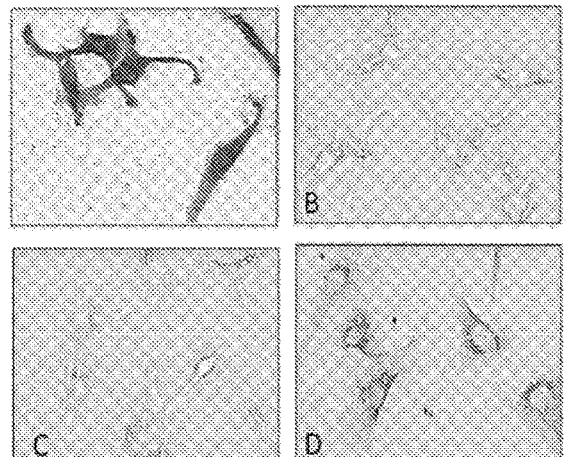
SKOV3    U87
SKOV3
Biotin-LXY30
+
Avidin-HRP
+
DAB
Picture 3
|  | A: Blank | B: NMDS-LXY30 only | C: PD-1 Only | D: NMDS-LXY30 |
|---|---|---|---|---|
| LXY30-NMDS | – | ✓ | – | ✓ |
| PD-1-GST | – | – | ✓ | ✓ |
| GST HRP | ✓ | ✓ | ✓ | ✓ |

Figure 32
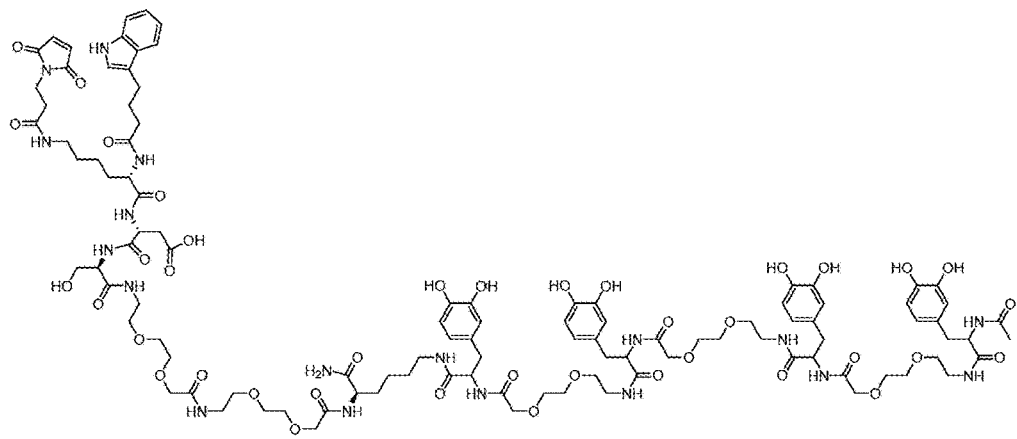
MDS-4DOPA
Chemical Formula: $C_{106}H_{146}N_{18}O_{39}$
Exact Mass: 2295.00
Molecular Weight: 2296.42
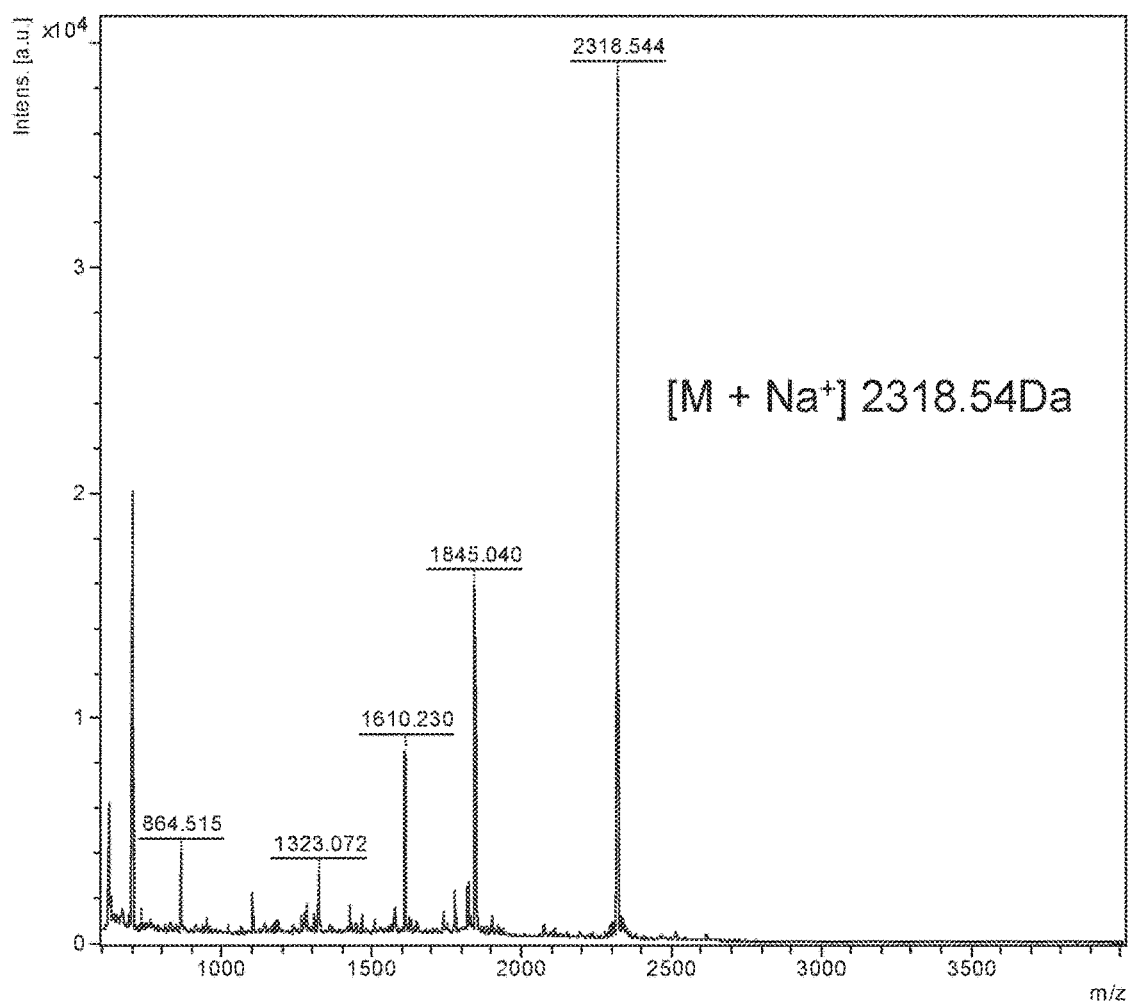
[M + Na⁺] 2318.54Da

SITE-SPECIFIC COVALENT CHEMICAL LIGATION TO MONOCLONAL AND POLYCLONAL IMMUNOGLOBULIN

CROSS-REFERENCES TO RELATED APPLICATIONS

This application is the U.S. National Stage Entry under § 371 of International Application No. PCT/US2016/026816, filed Apr. 8, 2016, which claims priority to U.S. Provisional Application No. 62/144,710, filed Apr. 8, 2015, each of which are hereby incorporated in the entirety for all purposes.

BACKGROUND OF THE INVENTION

Non-specific ligation methods have been traditionally used to chemically modify immunoglobulins. Site-specific ligation of compounds (detectable labels, toxins, or ligands) to antibodies has become increasingly important in the fields of therapeutic antibody-drug conjugates and bispecific antibodies.

BRIEF SUMMARY OF THE INVENTION

In a first embodiment, the present invention provides a compound comprising: i) a targeting moiety that specifically binds a nucleotide binding pocket of an antibody; ii) a cross-linking agent; iii) an active agent or a conjugating agent; and iv) a linker, wherein the linker covalently links: a) the targeting moiety, b) the cross-linking agent, and c) the active agent or conjugating agent.

In a second embodiment, the present invention provides a method for covalently conjugating an antibody to a molecular payload, wherein the molecular payload comprises any of the compounds described herein, the method comprising: a) forming a reaction mixture comprising the antibody and the molecular payload under conditions suitable to form a non-covalent binding interaction between a nucleotide binding pocket of the antibody and a targeting moiety of the molecular payload, wherein the reaction mixture is an aqueous solution having a pH of less than about 7.5; and b) raising the pH of the reaction mixture above about 8.0, under conditions suitable to form a covalent bond between the antibody and the cross-linking agent.

DEFINITIONS

As used herein, the following terms have the meanings ascribed to them unless specified otherwise.

It is to be understood that this invention is not limited to the particular methodology, protocols, and reagents described, as such may vary. It is also to be understood that the terminology used herein is for the purpose of describing particular embodiments only, and is not intended to limit the scope of the present invention, which will be limited only by the appended claims.

As used herein the singular forms "a," "and," and "the" include plural referents unless the context clearly dictates otherwise. Thus, for example, reference to "a compound" includes a plurality of such compounds and reference to "the antibody" includes reference to one or more antibodies and equivalents thereof known to those skilled in the art, and so forth. All technical and scientific terms used herein have the same meaning as commonly understood to one of ordinary skill in the art to which this invention belongs unless clearly indicated otherwise.

An "antibody" refers to a polypeptide of the immunoglobulin family or a polypeptide comprising fragments of an immunoglobulin that is capable of noncovalently, reversibly, and in a specific manner binding a corresponding antigen. The antibodies referred to herein contain one or more nucleotide binding pockets as defined by Rajagopalan et al., 1999 or U.S. Pat. No. 5,693,764. An exemplary antibody structural unit comprises a tetramer. Each tetramer is composed of two identical pairs of polypeptide chains, each pair having one light (about 25 kD) and one heavy chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used herein, an "antibody" encompasses all variations of antibody and fragments thereof that possess a particular binding specificity. Thus, the term "antibody" includes full length antibodies, chimeric antibodies, and humanized antibodies, and multimeric versions of these fragments (e.g., multispecific (including bispecific) antibodies, multivalent antibodies, tetramers) with the same binding specificity. The term "antibody" also includes fragments, relative to a full-length antibody, that possess a particular binding specification. An "antibody fragment" as used in here encompasses all variations of antibody fragments that possess a particular binding specifically. Thus, this term includes are single chain antibodies (ScFv), Fab, Fab', and multimeric versions of these fragments (e.g., F(ab')$_2$,) with the same binding specificity. While various antibody fragments, e.g., a Fab, may be defined in terms of the digestion of an intact antibody, one of skill will appreciate that such fragments may be synthesized de novo typically by using recombinant DNA methodology.

The antibody can be a monoclonal antibody, Alternatively, the antibody can be a polyclonal antibody or a mixture of structurally different monoclonal antibodies. In some cases, the antibody is an antibody that binds an antigen associated with a disease or condition. For example, the antibody can be an anti-tumor-associated-antigen antibody, In some cases, the antibody is an antibody that binds an immune cell (e.g., B cell, macrophage, dendritic cell, natural killer cell, natural killer T cell, helper T cell, or cytotoxic T cell). In some cases, the antibody is a checkpoint inhibitor. In some cases, the checkpoint inhibitor binds PD-1, PD-L1, or CTLA-4.

As used herein, the term "targeting moiety that specifically binds a nucleotide binding pocket of an antibody" refers to a moiety that forms a specific non-covalent interaction between the nucleotide binding pocket of an antibody—as defined by Rajagopalan et al., 1996 or U.S. Pat. No. 5,693,764 and the targeting moiety. Generally, the non-covalent interaction between the targeting moiety and the nucleotide binding pocket has dissociation constant ($K_d$) of better than (i.e., less than) about 8 μM., better than about 5 μM, better than about 1 μM, or about 1 μM. Such targeting moieties include purities, purine analogues, purine nucleotides, or purine nucleotide analogues. Exemplary targeting moieties include, but are not limited to, indole-3-butyric acid, methyl-indole-3-carboxaldehyde, fluorotryptamine, fluoroindole-3-carboxaldehyde, or methylindole-3-carboxyaldehyde.

As used herein, the term "cross-linking agent" refers to an agent that is capable of forming a covalent bond with a protein. In some cases, the cross-linking agent forms a covalent bond with an amine (e.g., a primary amine, such as the epsilon amine of a lysine side chain) of the protein (e.g., antibody). In some cases, the cross-linking agent forms a covalent bond with a guanidinium group (e.g., a guanidinium group of an arginine) of a protein (e.g., antibody). In some cases, the cross-linking agent forms a covalent bond with a sulfhydryl group of the protein (e.g., a sulfhydryl group of a cysteine side chain of an antibody).

In some cases, the cross-linking agent is a cryptic cross-linking agent that is capable of contacting a protein in a reaction mixture in a non-reactive (or crytpic) form. The cryptic cross-linking agent can then be triggered to form a covalent bond with the protein by changing the reaction mixture conditions. In some cases, the reaction mixture conditions are changed to cross-link the cross-linking agent and the protein by introduction of visible or ultraviolet light. In some cases, the reaction mixture conditions are changed to cross-link the cross-linking agent and the protein by raising the pH of the reaction mixture. In some cases, the reaction mixture conditions are changed to cross-link the cross-linking agent and the protein by introducing a catalyst to the reaction mixture. Exemplary cross-linking agents include, but are not limited to, photo-cross-linking agents, cross-linking agents comprising an acryloyl moiety, cross-linking agents comprising a maleimide moiety, cross-linking agents comprising a 1,5-difluoro-2,4-dinitrobenzene (DNDFB) moiety, or cross-linking agents derived from a 1,5-difluoro-2,4-dinitrobenzene (DNDFB) moiety, such as 5-fluoro-2,4-dinitrobenzene.

As used herein, the term "active agent" refers to an agent that can be used as a detectable label or a biologically active agent. Detectable labels can include one or more of the following: a label, a dye, a radionuclide, an affinity label, a ligand, a reactive compound, a resin, a second protein or polypeptide or polypeptide analog, a polynucleotide, a metal chelator, or a small molecule (e.g., a drug). In some cases the active agent can be a ligand for a biologically active agent.

A biologically active agent can include any cytotoxic, cytostatic or immunomodulatory drug. The biologically active agent can be a ligand to a cell. For example, the biologically active agent can be a ligand with affinity to an immune cell (e.g., B cell, macrophage, dendritic cell, natural killer cell, natural killer T cell, helper T cell, or cytotoxic T cell) or a tumor cell. Alternatively, the biologically active agent can be a ligand with affinity to a microbe.

As used herein, the term "linker" refers to a chemical moiety that covalently links the targeting moiety, the cross-linking agent, and the active agent or conjugating agent. In some cases, the linker has affinity to the antibody. For example, in some cases, the linker can be, or contain, an affinity element that increases the affinity (e.g., as demonstrated by a lower $K_d$) of the molecular payload to the antibody beyond that provided by the targeting moiety. Exemplary linkers include linkers that contain an ethylene glycol dimer or a PEG moiety. Exemplary linkers include linkers that contain an amino acid or an amino acid polymer (e.g., linkers that contain a polypeptide). In some cases, the amino acid or amino acid polymer is an affinity element. In some cases, the combination of the linker (e.g., a linker that contains an amino acid or an amino acid polymer) and the targeting moiety has a higher affinity (e.g., lower $K_d$) or greater binding specificity (e.g., lower background binding) than the targeting moiety alone. Thus, for example, the targeting moiety and linker can be used in combination to obtain improved cross-linking of an active agent or conjugating agent to a target protein e.g., antibody).

As used herein, the term "conjugating agent" refers to an agent that is covalently linked to a linker and contains a reactive moiety that can be used to covalently link the linker to an active agent. Exemplary conjugating agents contain 1,2-dihydroxybenzene. The 1,2-dihydroxybenzene can be used to covalently link an active agent containing a boronic acid. Other exemplary conjugating agents contain an alkyne or azide moiety. The alkyne or azide moiety can be used to covalently link an active agent containing a complementary alkyne or azide moiety to the conjugating agent via azide alkyne Huisgen cycloaddition or Copper (I)-catalyzed azide-alkyne cycloaddition. For example, if the conjugating agent contains an azide group, the active agent contains an alkyne. Conversely, if the conjugating agent contains an alkyne, the active agent contains an azide group.

BRIEF DESCRIPTION OF THE DRAWINGS

FIG. 9. (A-C) Cells (A: SKBR3; B:MCF7; C:MDA-MB-468) were incubated with 40 ng/ml of Trast or Trast-DS. 40 ng/ml trastuzumab or trast-DS were applied to cells prior to secondary antibody labeling, Cy3-labeled anti-human IgG Fc secondary antibody. The fluorescent intensity of the secondary antibody was recorded through FACs on each cell lines. The binding of Trast-DS to the NBP did not affect binding affinity of trastuzumab to SKBR3 or MCF7 cells. As expected, no binding of trastuzumab or trast-DS was seen in MDA-MB-468 cells, (D-E) Similar FACS analysis was performed on TrastDS-MMAE conjugates. In SKBR and MCF7 cells, the immunotoxin conjugates did not affect binding affinity of trastuzumab to the Her2(+) cells. No binding of trastuzumab or trastDS-MMAE, was seen in Her2(−) cells, MDA-MB-468 cells.

FIG. 20. (TOP) Depicts a compound described herein containing a maleimide cross-linking agent, an indole targeting moiety, a linker containing a lysine-aspartate-serine amino acid sequence, and a dihyroxyphenylalanine active agent (MDS-1DOPA). (BOTTOM) Depicts mass spectrometry data confirming synthesis of the compound depicted above.

FIG. 22. (TOP) Depicts a compound described herein containing a maleimide cross-linking agent, an indole targeting moiety, a linker containing a lysine-aspartate-serine amino acid sequence, and an active agent containing two dihyroxyphenylalanine moieties (MDS-2DOPA). (BOTTOM) Depicts mass spectrometry data confirming synthesis of the compound depicted above.

FIG. 29. Depicts binding of the bi-functional conjugate characterized in FIG. 28 to PD-1 and $\alpha_3\beta_1$-integrin.

FIG. 32. Depicts (TOP) Depicts a compound described herein containing a maleimide cross-linking agent, an indole targeting moiety, a linker containing a lysine-aspartate-serine amino acid sequence, and an active agent containing four dihyroxyphenylalanine moieties (MDS-4DOPA). (BOTTOM) Depicts mass spectrometry data confirming synthesis of the compound depicted above.

DETAILED DESCRIPTION

I. Introduction

Figure 1:
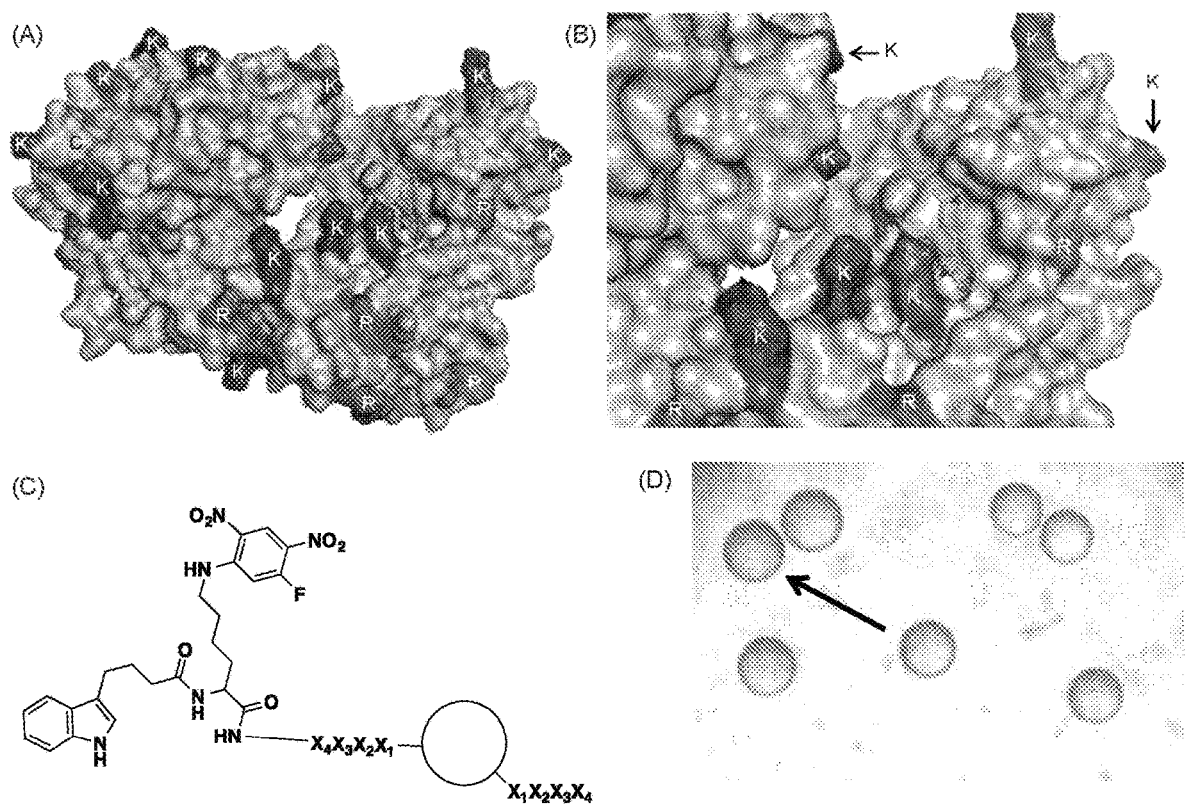
FIG. 1. (A, B) Depicted here is one of the F(ab) arms used in the Autodock studies. indole-3-butyric acid can be seen nestled within the nucleotide binding pocket (NBP). Cross-linking agent can be reacted with proximal lysines, cysteines, or arginines in or near the NBP, as indicated. (C) Based upon the top clusters generated from Autodock, several libraries were designed. X1X2X3X4 library with DNFB is shown. (D) Sample image of screening. Arrow indicates labeled bead.

Described herein are methods and compositions for utilizing the nucleotide-binding pocket in antibody F(ab) arms to target a compound for covalent attachment to the antibody. As described herein, nucleotide-based cross-linking agent-derivatized One Bead One Compound (OBOC) peptide libraries are developed for the identification of linkers that increase binding affinity of the cross-linking agent to the antibody and can be used as site-specific derivatization agents against both monoclonal and polyclonal antibodies. Immunoconjugates resulting from such linkers can be used as diagnostic agents and therapeutics against cancer or infectious agents.

Targeted therapy using monoclonal antibodies (mAbs) has revolutionized the treatment of cancer by recognizing antigens expressed on cell surfaces[1,2]. The addition of cytotoxic drugs to these mAbs, creating antibody-drug conjugates (ADC) was a natural extension of this approach, and has achieved varying success in the clinic. These antibody drug conjugates combine the targeted specificity of mAbs with the enhanced tumor-killing power of toxic effector molecules permitting the sensitive discrimination between target and normal tissue, resulting in fewer toxic side effects than most conventional chemotherapeutic drugs[3]. Recently, trastuzumab emtansine (Kadcyla; Genentech/Roche), an anti-Her2 maytansine conjugate demonstrated an improved survival compared to standard treatment[4]. Similarly, Brentuximab Vedotin (Adcetris; Seattle Genetics) received accelerated approval for the treatment of relapsed Hodgkin lymphoma or relapse systemic anaplastic large cell lymphoma through the use of a CD30 directed antibody drug conjugated with a microtubule-disrupting agent monoomethyl auristatin E (MMAE)[5]. The first clinically approved ADC, gemtuzumab ozogamicin (Mylotarg; Wyeth/Pfizer) was removed from the market because of toxicity and lack of efficacy in larger clinical trials[6]. Although these approvals show great potential of ADCs to impact major unmet needs in oncology, the withdrawal of Mylotarg shows that further work is necessary to optimize this new class of drugs[7].

The cytotoxic drugs are generally conjugated to antibodies through nonspecific methods, including targeting (1) primary airlines from lysine or (2) free sulfhydryls from cysteines by reduction of the hinge and inter-strand disulfide bonds[8]. These modifications, however, creates heterogeneous products because of the reoccurrence of the same functional groups. These complex mixtures lead to variable in vivo pharmacokinetics, efficacy, and safety profiles[8]. The high abundance of lysine in each immunoglobulin molecule, for example, makes it difficult to control the stoichiometry and specificity of the chemical conjugates. Although there are fewer cysteines on an antibody, modification of the cysteines may alter the stability and function of the antibody[9]. Therefore, to create a homogenous product, extensive purification processes are needed. Many investigators have moved towards the development of site-specific modifications to create ADCs, providing complete control over the attachment thereby decreasing heterogeneity in the final clinical products.

Current site-specific conjugation methods include both antibody engineering and chemical methods. Several research groups have engineered a cysteine residue on the surface of the antibody to introduce sulfhydryl groups for subsequent conjugation to a linker payload[2,10]. These methods have successfully created homogenous conjugates. However, the engineering of these antibodies require extensive optimization, therefore lengthening the time for these molecules to reach the clinic. A number of chemical methods have emerged by modifying N-terminal residues[11,12] targeting tyrosine residues[13,14], or adding recognition tags for enzymatic modification[15-17]. While these methods can site-specifically conjugate a payload to antibodies, many of these processes require the use of organic solvents which are often times too harsh to maintain folded protein structures[18] or require very extensive conjugation times which may affect protein stability. Conjugation to the N-terminus, for example, can also be problematic as the conjugation of a cytotoxic payload or a ligand may affect epitope binding which is typically mediated by regions at or near the N-terminus.

As a simple alternative, site-specific conjugation to clinically available antibodies can be done through the use of a ligand that binds directly to the Fab arm. Here, we propose to use of a novel site-specific affinity element to chemically modify antibodies with a wide array of different functional groups including peptides, detectable labels, small molecules, cytotoxic agents, etc. This blending of features of site-specific conjugated functional groups and mAbs, without antibody engineering, is economically attractive because it can utilize many existing clinically available antibodies, reducing production costs and shortening preclinical-to-clinical translation times[19]. Rajagopalan et al.[20] have identified a nucleotide-binding pocket (NBP), which exists in all immunoglobulin Fab arms. This highly conserved pocket is located between the variable light (VL) and variable heavy (VH) domain of all antibody isotypes[20-22]. Through an in silica docking study, Handlogten et al.[22] identified indole-3-butryic acid as a highly specific compound that binds to the NBP with Kds ranging between 1 μM to 8 μM, with binding affinity dependent on the antibody[20,22]. Alves et al[23] has described a UV photocrosslinking method relying on the indole group to crosslink to specific residues within the NBP of IgG. This method requires the use of UV excitation to develop an indole radical used for crosslinking. This requirement for UV excitation increases the risk of impairing Fc recognition and creates a loss in the antibody's ability to recognize its antigen. Together, there is an increased need to discover enhanced small molecules that can take advantage of this nucleotide binding pocket for site specific ligation.

We have taken advantage of the site specificity provided by indole-3-butryic acid and developed focused one-bead-one-compound (OBOC) combinatorial peptide libraries capped by indole-3-butryic acid to discover an affinity element capable of site-specific ligation to the nucleotide-binding site of immunoglobulin via proximity-ligation. For irreversible ligation to free amines and thiols at the nucleotide-binding site, we placed a 1,5-difluoro-2,4-dinitrobenzene (DNDFB) moiety[24] or a maleimide moiety adjacent to the indole group of the OBOC library. This crosslinking agent (e.g., DNDFB or maleimide), in addition to our targeting ligand (e.g., indole and peptide containing linker), makes it a superior conjugate because of the mild conditions required to covalently crosslink to the antibody. From this library we have discovered several linkers that allow site-specific introduction of orthogonal functional groups that can be readily used for subsequent conjugation of a cytotoxic payload, detectable label, or ligand for generating a bispecific antibody. For example, this linker can be used for the ligation of toxin such as monomethyl auristatin E (MMAE) to make antibody-toxin conjugates for cancer therapy. This can be done through the use of existing clinically available mAbs such as Herceptin, Avastin, and Rituxan.

Figure 18:
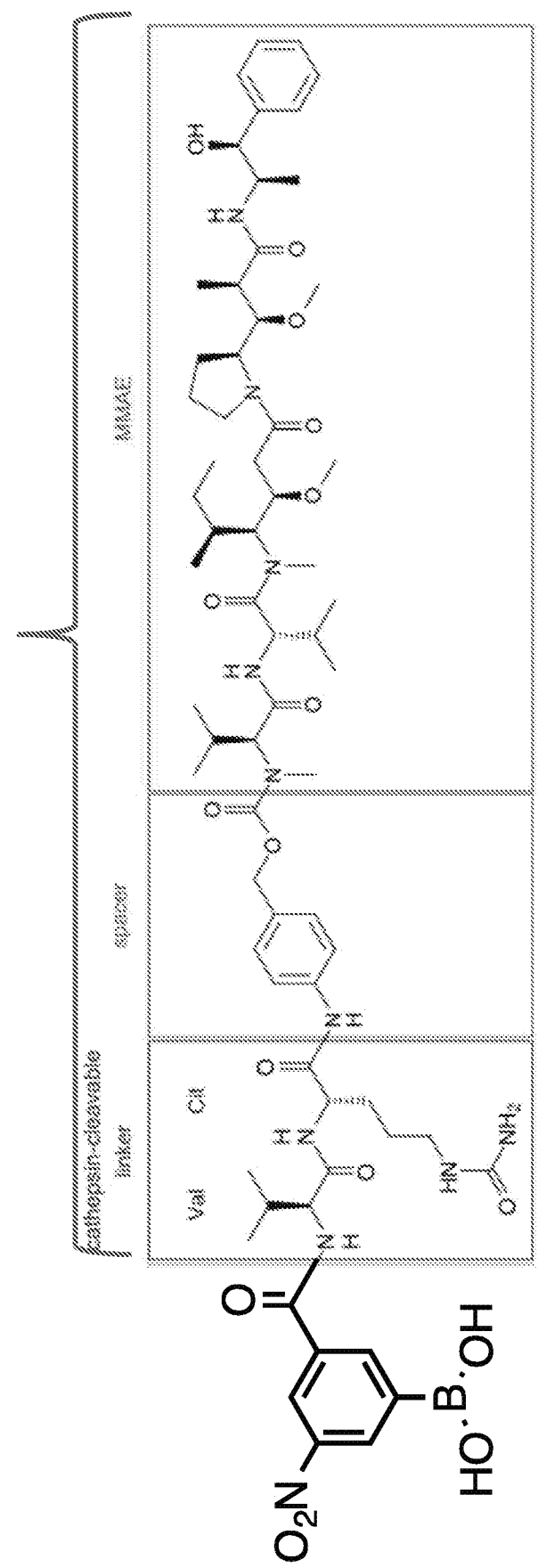
FIG. 18. Depicts a boronic acid monomethyl auristatin E (MMAE) biologically active agent.

In some cases, the conjugate can be used for site-specific introduction of a functional that can be used to form a further covalent bond to an active agent (e.g., biologically active agent). For example, the conjugate can introduce one or more (e.g., 2, 3, 4. 5, 6, or more) 1,2-dihydroxybenzne groups (e.g., in the form of dihydroxyphenylalanine). These dihydroxybenzne groups can each in turn be used to conjugate a boronic acid containing group and form a boronic ester under mild conditions. In some cases, the boronic acid containing group further contains a cytotoxic payload such as the MMAE derivative depicted in FIG. 18. As another example, the conjugate can introduce one or more (e.g., 2, 3, 4, 5, 6, or more) azide or alkyne functional groups.

In addition, one may site-specifically introduce disease-specific targeting ligands onto readily available monoclonal or polyclonal human intravenous immunogobulins (IVIGs) without the need to reengineer an antibody, which can take months to years. This latter application is particularly useful for, e.g., rapid deployment of neutralizing antibodies against emerging pathogens in epidemics and pandemics, such as the recent Ebola outbreak. Alternatively, a monoclonal antibody conjugated to a disease-specific targeting ligand can be used for bringing effector and target cells into proximity to enhance the activity of effector cell induced cytotoxicity. For example, a checkpoint inhibitory antibody (e.g., anti-PD-1, anti-PD-L1, anti-CTLA4, etc.) can be conjugated to a disease-specific targeting ligand. Checkpoint inhibitory antibodies that bind an effector immune cell (e.g., T cell) antigen (e.g., PD-1) can be conjugated to a target cell specific ligand to increase effector cell cytotoxic activity against the target cell. In some cases, the target cell specific ligand is or contains an LXY30 peptide. Similarly, checkpoint inhibitory antibodies that bind a target cell antigen (e.g., PD-L1) can be conjugated to an effector immune cell specific ligand to increase effector cell cytotoxic activity against the target cell. The target cell can be a microbe, or a tumor cell. In some cases, the target cell is a tumor cell.

II. Compositions

Described herein is a compound comprising i) a targeting moiety that specifically binds a nucleotide binding pocket of an antibody; ii) a cross-linking agent; iii) an active agent or a conjugating agent; and iv) a linker, wherein the linker covalently links: a) the targeting moiety, b) the cross-linking agent, and c) the active agent or conjugating agent. In some cases, the cross-linking agent is an acryloyl functional group. In some cases, the cross-linking agent is a photo-crosslinking group. In some cases, the cross-linking agent is a cross-linking agent that can be activated to cross-link to (i.e., form a covalent bond to) a protein (e.g., antibody) by raising the pH of a reaction mixture in which the cross-linking agent is present to at least about 8.0 or 8.5. In some cases, the cross-linking agent is 5-fluoro-2,4-dinitrobenzene (DNFB). In some cases, the cross-linking agent is maleimide.

The linker can be any compound capable of linking a targeting moiety, a cross-linking agent, and an active agent or conjugating agent. In some cases, the linker contains one or two ethylene glycol moieties. In some cases, the linker contains a polyethylene glycol (PEG) polymer. In some cases, the linker contains an ethylene glycol dimer or a PEG polymer. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to an amino acid by the formula: XO—$(CH_2CH_2O)_{=n}$—$CH_2CH_2$—Y where n is 3 to 10,000 or more and X is H or a terminal modification, including but not limited to, a $C_{1-4}$ alkyl. In some cases, a PEG used in the invention terminates on one end with hydroxy or methoxy, i.e., X is H or $CH_3$ ("methoxy PEG").

In some cases, the linker contains an amino acid sequence. The amino acid sequence can contain negatively charged amino acids. In some cases, the negatively charged amino acids are aspartate, glutamate, or a combination thereof. In some cases, the linker contains an amino acid sequence and an ethylene glycol dimer or PEG polymer. In some cases, the linker contains a lysine-aspartate-serine amino acid sequence and an ethylene glycol dimer. In some cases, the linker contains an ethylene glycol dimer and an amino acid sequence selected from the group consisting of: Ile; Leu; Ser; Asp; His; Phe; Glu; Asn; Asp-Ser; Phe-Bpa; Asp-Leu; Asp-Gly; Trp-Glu; Bpa-Gln; Asp-Thr; Trp-Phe-Gln; Phe-Asp-His; Asp-Trp-Nva; Glu-Asp-Pro; Trp-Phe(2Cl)-Thr-Thr; Thr-HoCit-His-His; Phe(2Cl)-Thr-Phe(2Cl)-Gln; Glu-Leu-Gln-Nal2; Glu-HoPhe-Gln-His; Glu-Ala-Asn-Glu; and Asp-Gly-Phe(2Cl)-Thr.

In some cases, the linker can contain an affinity element that increases the specificity or affinity of the targeting moiety to which it is linked to the nucleotide binding pocket of an antibody. In some cases, the affinity element is an amino acid sequence. For example, the affinity element can be an amino acid sequence that contains 1, 2, 3, 4, 5, 6, 7, 8, 9, 10, or more negatively charged amino acids. As another example, the affinity element can be a water soluble or hydrophilic amino acid sequence. For instance, the affinity element can contain 1, 2, 3, 4, 5, 6, 7, 8, 9, 10, or more polar amino acids. In some cases, the affinity element is a di- or tripeptide. In some cases, the affinity element contains a lysine, an aspartate, and a serine. In some cases, the affinity element contains a lysine-aspartate-serine amino acid sequence. In some cases, the affinity element contains an aspartate and a serine. In some cases, the affinity element contains an aspartate-serine amino acid sequence.

The compound can have the following formula:

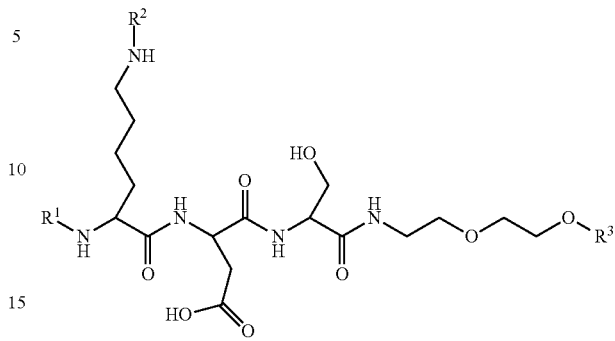

where $R^1$ contains the targeting moiety that specifically binds to the nucleotide binding pocket of an antibody; $R^2$ contains the cross-linking agent; and $R^3$ contains the active agent or conjugating agent.

In some embodiments, the targeting moiety that specifically binds the nucleotide binding pocket of an antibody comprises a purine nucleotide or a purine nucleotide analogue. In some cases, the purine nucleotide or purine nucleotide analogue contains an indole. In some cases, the purine nucleotide or purine nucleotide analogue is indole-3-butyrate. Exemplary targeting moieties can further include sinefungin, methyl-indole-3-carboxaldehyde, fluorotryptamine, fluoroindole-3-carboxaldehyde, or methylindole-3-carboxaldehyde.

In some embodiments, the compound has the following formula:

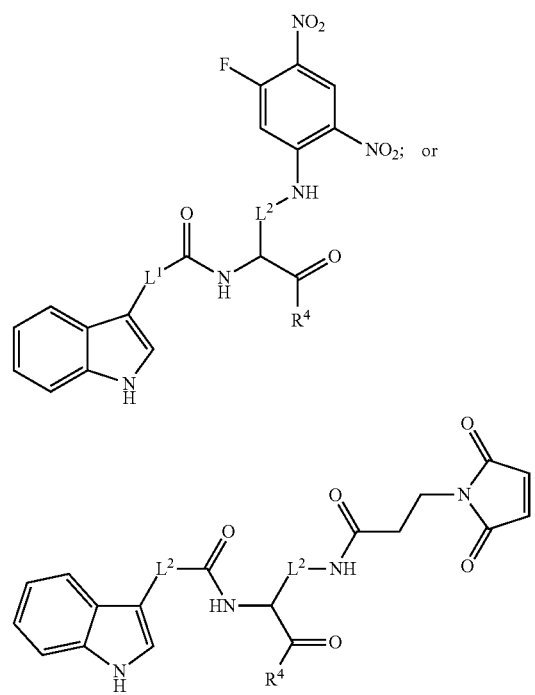

wherein $L^1$ and $L^2$ are independently a $C_1$-$C_{10}$ alkylene, and $R^4$ is represented by the following formula:

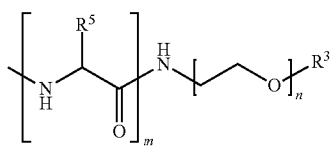

where $R^5$ is an amino acid side chain, m and n are independently from 1 to 10, and $R^3$ contains the active agent or conjugating agent.

In some cases, the amino acid side chains of $R^5$ are independently selected to include one or more negatively charged amino acids (e.g., aspartate or glutamate) or one or more polar amino acids (e.g., serine, threonine, histidine, glutamine, asparagine, tyrosine, cysteine, methionine, or tryptophan). In some cases, the amino acid side chains are independently selected to include an affinity element that increases the affinity of a targeting moiety to the nucleotide binding pocket of an antibody. Exemplary affinity elements include, but are not limited to, a di- or tripeptide, such as a di- or tripeptide that contains one or more negatively charged or one or more polar amino acids, or a combination thereof. Exemplary affinity elements can include affinity elements that contain lysine, aspartate, and serine. Exemplary affinity elements can include affinity elements that contain a lysine-aspartate-serine amino acid sequence. Exemplary affinity elements can include affinity elements that contain aspartate and serine. Exemplary affinity elements can include affinity elements that contain an aspartate-serine amino acid sequence.

In some embodiments, the compound has the following formula:

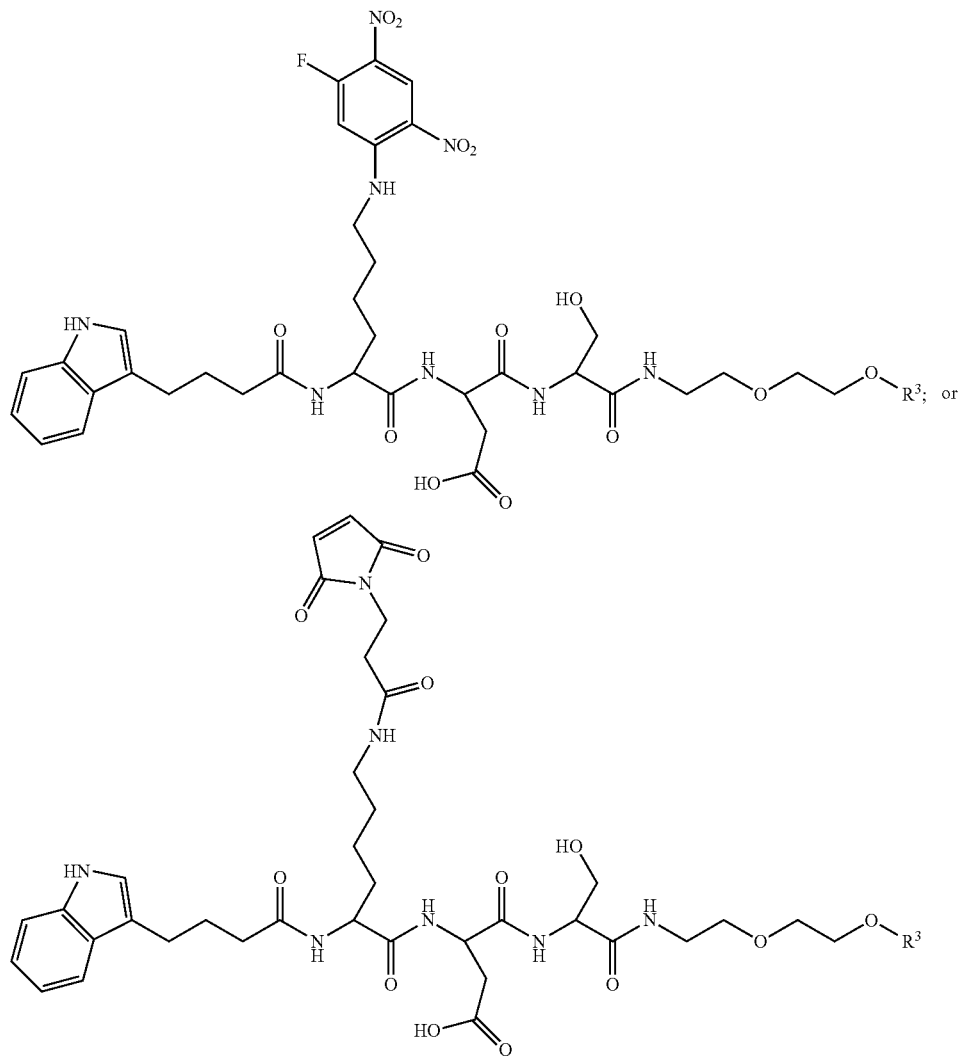

; or where $R^3$ contains the active agent or conjugating agent.

In some embodiments, the active agent contains a detectable label. The detectable label can be a label, a dye, a radionuclide, an affinity label, a photoaffinity label, a reactive compound, a resin, or a second protein or polypeptide or polypeptide analog. The second protein can or polypeptide can be an antibody or antibody fragment, an enzyme (e.g., horse radish peroxidase, alkaline phosphatase, etc.), or a protein ligand. The detectable label can be a metal chelator (e.g., 1,4,7,10-tetraazacyclododecane-1,4,7,10-tetraacetic acid (DMA)), a polynucleotide, a DNA, an RNA, a nanoparticle, a spin label, a fluorophore, a metal-containing moiety, a group that covalently or noncovalently interacts with other molecules, a photocaged moiety, a photoisomerizable moiety, biotin, a derivative of biotin, a biotin analogue, avidin, streptavidin, a moiety incorporating a heavy atom, a chemically cleavable group, a photocleavable group, a redox-active agent, a biophysical probe, a phosphorescent group, a chemiluminescent group, an electron dense group, a magnetic group, an intercalating group, a chromophore, an energy transfer agent, or any combination of the foregoing. In some cases, the detectable label is a biotin molecule.

In some cases, the active agent contains a biologically active agent. The biologically active agent can include any cytotoxic, cytostatic or immunomodulatory drug. The biologically active agent can be a ligand to a cell. For example, the biologically active agent can be a ligand with affinity to an immune cell (e.g., natural killer cell, natural killer T cell, or cytotoxic T cell). Alternatively, the biologically active agent can be a ligand with affinity to a microbe.

In some cases, the biologically active agent is a cytotoxic or immunomodulatory agent. In some cases, the active agent is a chemotherapeutic agent. Useful classes of chemotherapeutic, cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids (e.g., vincristine, vinblastine, vindesine, and vinorelbine), radionuclides (e.g., Yt-99), or the like. In sonic cases, the active agent contains a cytotoxic agent. In some cases, the cytotoxic agent is monomethyl auristatin E. In some cases, the cytotoxic agent is vincristine.

In some embodiments, the compound has the following formula:

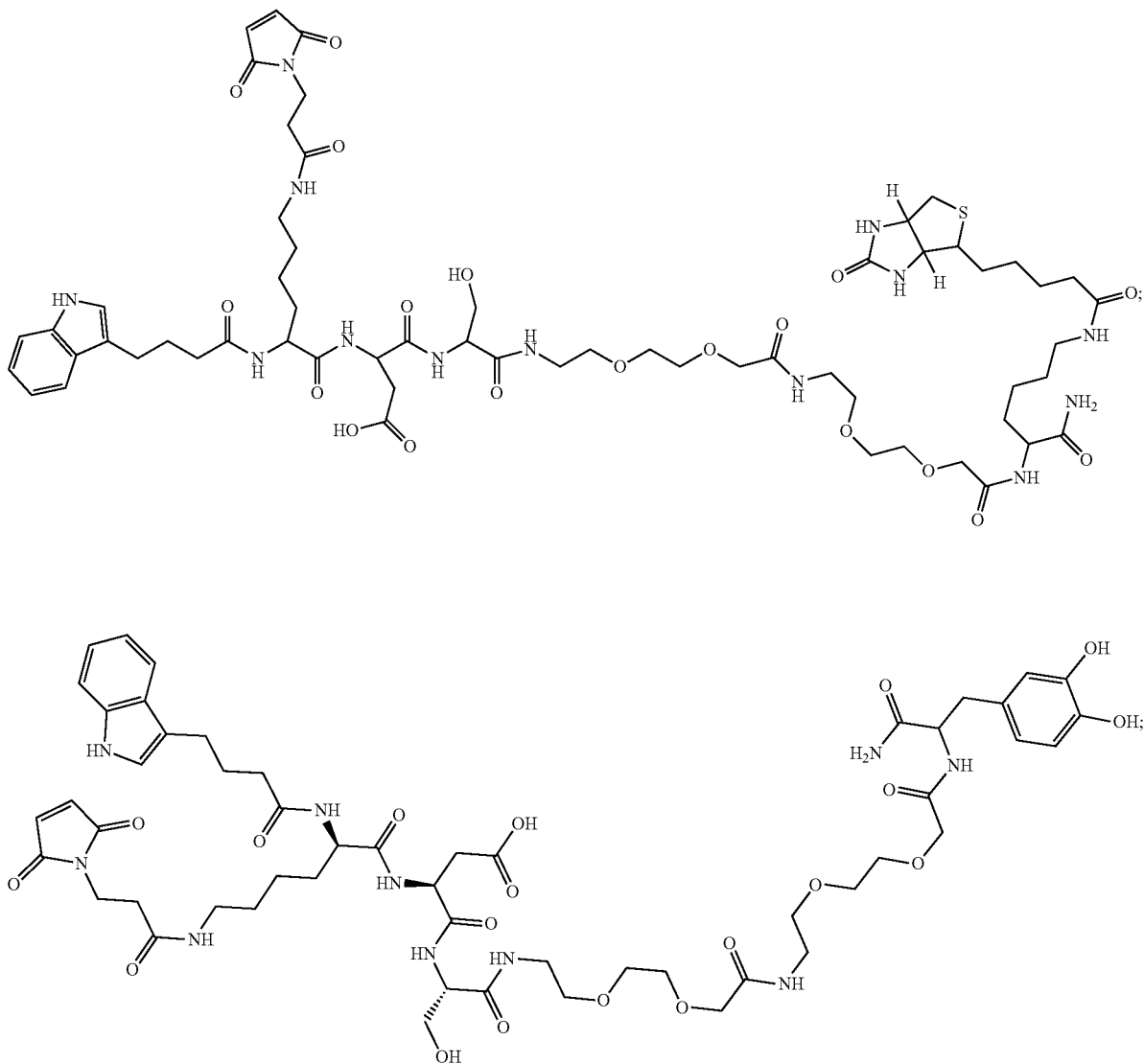

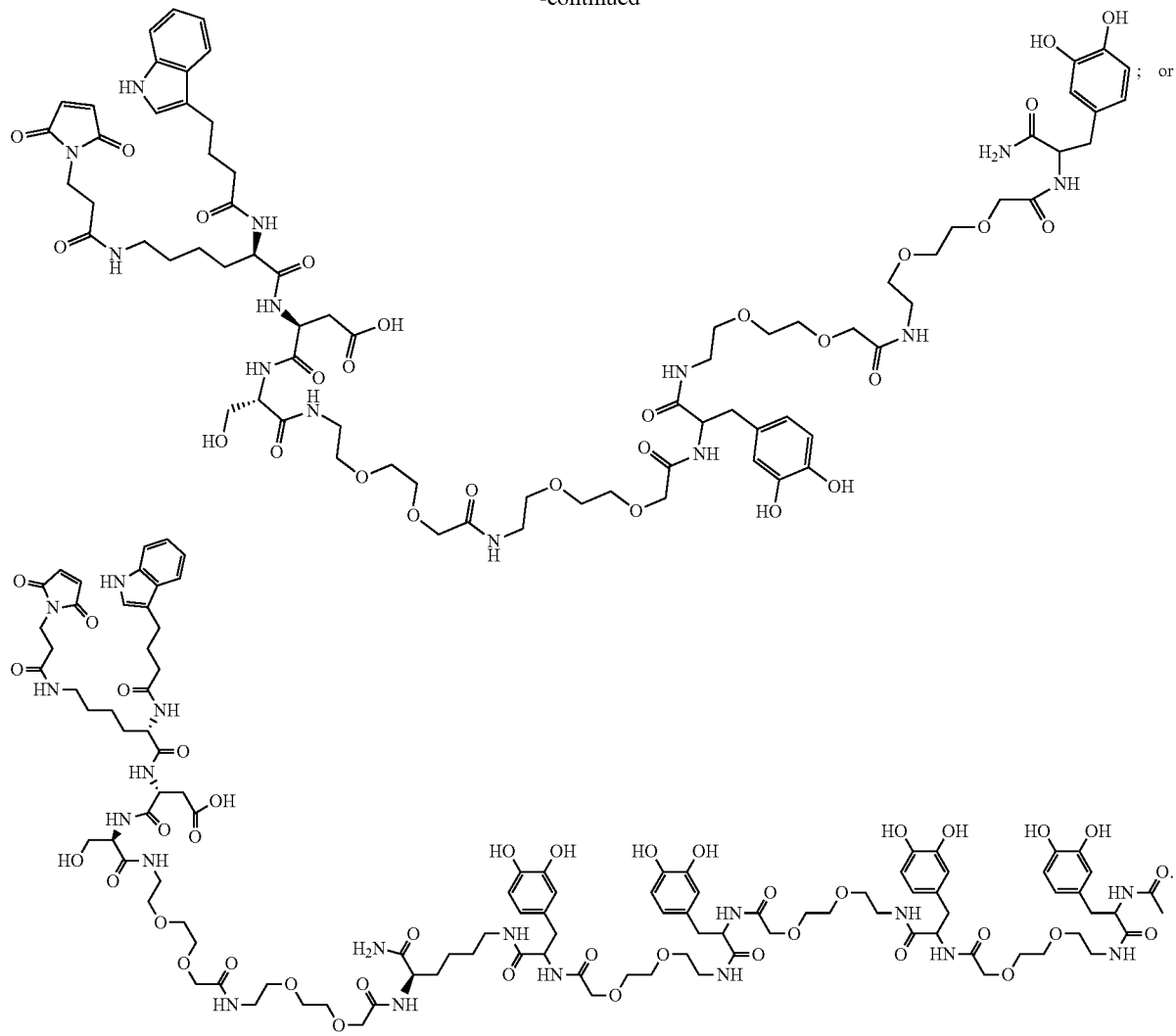
In some embodiments, the compound contains the following formula:
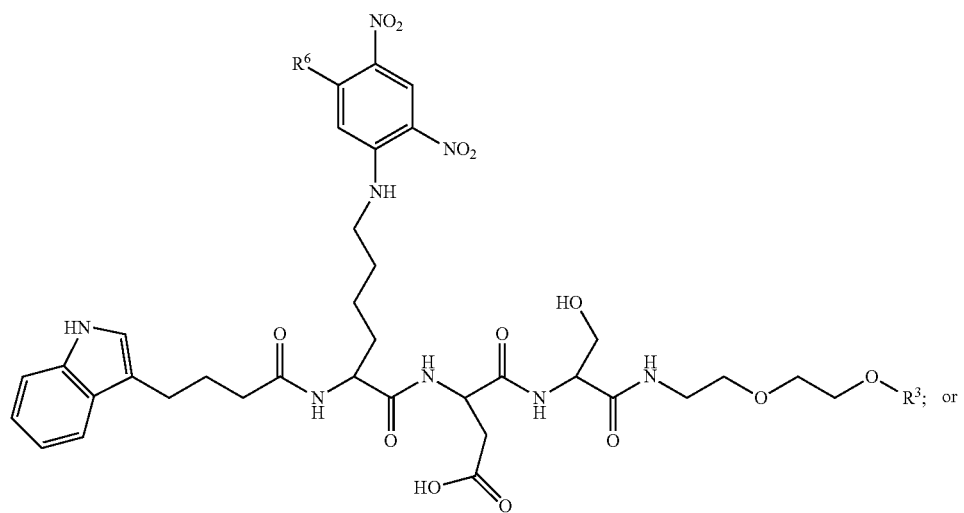

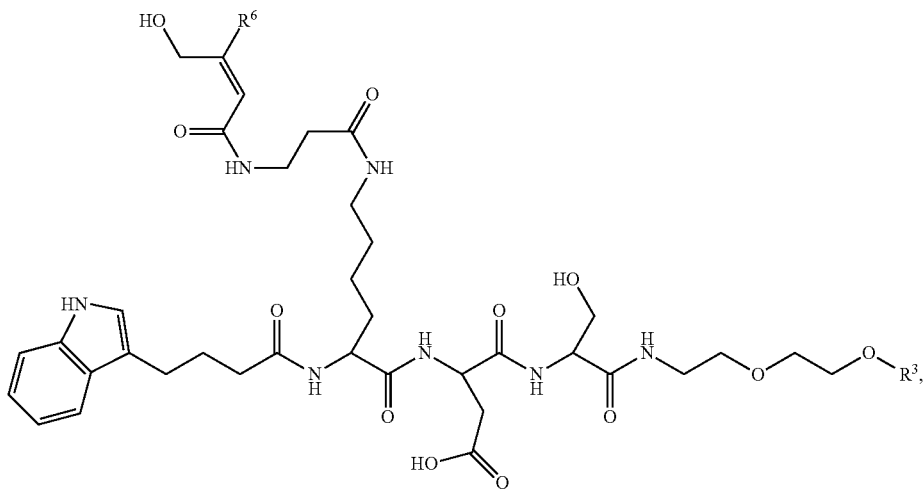

wherein $R^6$ is an antibody and $R^3$ comprises an active agent or conjugating agent. The antibody can be any antibody known in the art, so long as it contains one or more nucleotide binding pockets. Nucleotide binding pockets can be located between the variable light and variable heavy chain domains of all antibody isotypes. Thus, in some cases, the nucleotide binding pocket contains a variable light chain domain and variable heavy chain domain. In some cases, the nucleotide binding pocket includes the CDR1 domain and at least a portion of the FR2 region of a variable light chain. In some cases, the nucleotide binding pocket includes the CDR3 domain and at least a portion of the FR4 region of the variable heavy chain. In some cases, the nucleotide binding pocket includes residues H100, H101, H103 L44, L36, or a combination thereof. In some cases, H100 is Glu. In some cases, H101 is Asp. In some cases, H103 is Trp. In some cases, L44 is Pro. In some cases, L36 is Tyr. In some cases, the antibody is a. polyclonal antibody. For example, the antibody can be immunoglobulin harvested from a donor. In some cases, the antibody is immunoglobulin harvested from a donor that is conjugated to a molecular payload compound described herein using a method described herein and administered to a subject (e.g., by intravenous administration). In some cases, the polyclonal antibody is Flebogamma, Gamunex, Privigen or Gammagard.

In some embodiments, the conjugating agent contains an azide or alkyne. The use of a conjugating agent containing an azide or alkyne group can enable facile linkage to an active agent (e.g., detectable label or biologically active agent) via cycloaddition. For example copper catalyzed cycloaddition. Thus, when the conjugating agent contains an azide, an active agent containing an alkyne can be linked to the conjugating agent. Alternatively, when the conjugating agent contains an alkyne, an active agent containing an azide can be linked to the conjugating agent.

III. Methods

Described herein is a method for covalently conjugating one or more of the foregoing compounds to an antibody. In some embodiments, the method is for covalently conjugating an antibody to a molecular payload, where the molecular payload is comprised of any one of the foregoing compounds described herein that contains a cross-linking agent. In some cases, the method includes: a) forming a reaction mixture containing the antibody and the molecular payload under conditions suitable to form a non-covalent binding interaction between a nucleotide binding pocket of the antibody and a targeting moiety of the molecular payload; and b) triggering a cross-linking event between the antibody and the cross-linking agent of the molecular payload. The cross-linking event can be triggered by one or more of the following: raising the pH, lowering the pH, introducing an oxidant, introducing a reductant, irradiating the reaction mixture (e.g., with ultraviolet or visible light, or a combination thereof), or introducing a catalyst into the reaction mixture.

In some cases, the method can include: a) forming a reaction mixture containing the antibody and the molecular payload under conditions suitable to form a non-covalent binding interaction between a nucleotide binding pocket of the antibody and a targeting moiety of the molecular payload, wherein the reaction mixture is an aqueous solution having a pH of less than about 7.5; and b) raising the pH of the reaction mixture above about 8.0, under conditions suitable to form a covalent bond between the antibody and the cross-linking agent. The pH of the reaction solution in a) can be about 4, 4.5, 5, 5.5, 6, 6.5, 7, 7.5, or 8.0. The raising the pH of b) can be raising the pH of the reaction mixture above about 8.0, 8.5, 9.0, 9.5, 10.0, or more.

The pH can be raised by a variety of methods. In some cases, a base is added to the reaction mixture. In some cases, a basic solution is added to the reaction mixture. In some cases, a basic solution containing a primary amine is added to the reaction mixture. The use of a basic solution containing a primary amine can serve to raise the pH and thus trigger cross-linking and quench the cross-linking agents of any molecular payload that is not in a non-covalent interaction with the nucleotide binding pocket via the targeting moiety. Exemplary bases or basic solutions include, but are not limited to sodium bicarbonate, NaOH, NH$_4$OH, 0.1 N NaOH, 0.1 M sodium bicarbonate (e.g., pH 8, 8.5, 9, 9.5, 10, 10.5, or higher), 0.1 N NH$_4$OH, or 7 N NH$_4$OH. In some cases, the basic solution contains 0.1 M sodium bicarbonate pH 8.5, 0.1 N NaOH or 0.1 N NH$_4$OH.

In some cases, the cross-linking forms a covalent bond between the cross-linking agent and a primary amine, a sulfhydryl, or a guanidinium group of the antibody. In some cases, the primary amine, sulfhydryl, or guanidinium group is within 8 Å of the nucleotide binding pocket. In some cases, the primary amine, sulfhydryl, or guanidinium group is within 6 Å of the nucleotide binding pocket of the antibody. In some cases, the primary amine, sulfhydryl, or guanidinium group is within 4 Å of the nucleotide binding pocket. In some cases, the primary amine, sulfhydryl, or guanidinium group is within an amino acid reside that forms the nucleotide binding pocket. Generally, the maximum distance between the nucleotide binding pocket and the antibody amino acid functional group that cross-links with the cross-linking agent is controlled by the distance between the targeting moiety and the cross-linking agent. In an exemplary embodiment, the targeting moiety and the cross-linking agent are linked by a lysine, and the distance between the targeting moiety and the cross-linking agent is less than about 8 Å, 6 Å, or 4 Å.

In some cases, the cross-linking forms a covalent bond between the cross-linking agent and a primary amine of the antibody. In some cases, the cross-linking forms a covalent bond between the cross-linking agent and an epsilon amine of a lysine side chain of the antibody. In some cases, the cross-linking forms a covalent bond between the cross-linking agent and an epsilon amine of a lysine side chain of the antibody that is within less than about 8 Å, 6 Å, or 4 Å of the nucleotide binding pocket of the antibody.

In some embodiments, the method includes incubating the reaction mixture containing the antibody and the molecular payload for at least about 0.25 h. The incubating can allow the non-covalent interaction between the targeting moiety of the molecular payload and the nucleotide binding pocket of the antibody to occur, at least partially occur, or to reach equilibrium. In some cases, the incubating the reaction mixture containing the antibody and the molecular payload is performed for 0.25, 0.5, 0.75, 1, 2, 3, 4, 5, 6, 7, 8, 12, 18, 24 h, or more.

In some embodiments, the conditions suitable to form the non-covalent binding interaction between the nucleotide binding pocket of the antibody and the targeting moiety of the molecular payload include a reaction mixture temperature of about 20° C. In some cases, the reaction mixture temperature during the non-covalent binding is from about 4° C. to about 45° C. In some cases, the reaction mixture temperature during the non-covalent binding is from about 4° C. to about 37° C. In some cases, the reaction mixture temperature during the non-covalent binding is from about 4° C. to about 30° C. In some cases, the reaction mixture temperature during the non-covalent binding is from about 4° C. to about 25° C. In some cases, the reaction mixture temperature during the non-covalent binding is about 4, 6, 8, 10, 12, 14, 18, 20, 25, 30, 35, 37, 40, or about 45° C.

In some embodiments, the reaction mixture of a) contains phosphate buffered saline. In some cases, the reaction mixture of a) comprises phosphate buffered saline at a pH of about 7.0 (PBS 7.0) or phosphate buffered saline at a pH of about 7.5 (PBS 7.5). In some cases, the phosphate buffered saline contains sodium and potassium ions. In some cases, the phosphate buffered saline contains sodium ions. In some cases, the phosphate buffered saline contains calcium ions. In some cases, the phosphate buffered saline contains magnesium ions. In some cases, the phosphate buffered saline is calcium free. In some cases, the phosphate buffered saline is magnesium free. In some cases, the phosphate buffered saline is calcium and magnesium free. An exemplary phosphate buffered saline is prepared by introducing into water 137 mM NaCl, 2.7 mM KCl, 10 mM Na$_2$HPO$_4$, and 1.8 mM KH$_2$PO$_4$, and adjusting the pH to 7.0, 7.4, or 7.5. In some cases, the pH is adjusted with HCl. In some cases, the pH is adjusted with NaOH.

In some cases, the reaction mixture of a) contains a molar excess of molecular payload relative to nucleotide binding pockets. In some cases, the reaction mixture of a) contains a molar excess of molecular payload relative to nucleotide binding pockets and the method further includes removing unbound molecular payload from the reaction mixture after forming the non-covalent interaction between the targeting moiety and the nucleotide binding pockets and before cross-linking.

In some cases, the reaction mixture of a) contains a molar excess of molecular payload relative to nucleotide binding pockets and the method further includes removing unbound molecular payload from the reaction mixture after a) and before b). The unbound molecular payload can be removed from the reaction mixture by dialysis or size exclusion chromatography. In some cases, the size exclusion chromatography includes applying the reaction mixture to a desalting column and collecting the flow through fraction. In some cases, the size-exclusion chromatography includes high performance liquid chromatography (HPLC) or fast protein liquid chromatography (FPLC). For example, a gel filtration column can be used with an HPLC or FPLC system to separate bound and unbound molecular payload prior to the cross-linking step. In sonic cases, unbound molecular payload and/or unconjugated antibody, can be removed additionally, or alternatively, after the cross-linking step, e.g., by dialysis or size-exclusion chromatography.

In some cases, the molecular payload contains a conjugating agent that includes an azide or alkyne, and after forming the covalent bond between the antibody and the cross-linking agent, the method further comprises conjugating an active agent to the azide or alkyne via azide alkyne Huisgen cycloaddition or Copper (I)-catalyzed azide-alkyne cycloaddition. In some cases, the molecular payload contains a conjugating agent that includes a boronic acid conjugating group (e.g., 1,2-dihydroxybenzene such as dihyroxyphenylalanine). The method further comprises conjugating an active agent to the boronic acid conjugating group via boronic ester synthesis.

In some embodiments, the method includes a) forming the reaction mixture comprising PBS 7.0 or PBS 7.5, the antibody, and a 5-fold molar excess of the following molecular payload relative to nucleotide binding pockets of the antibody,

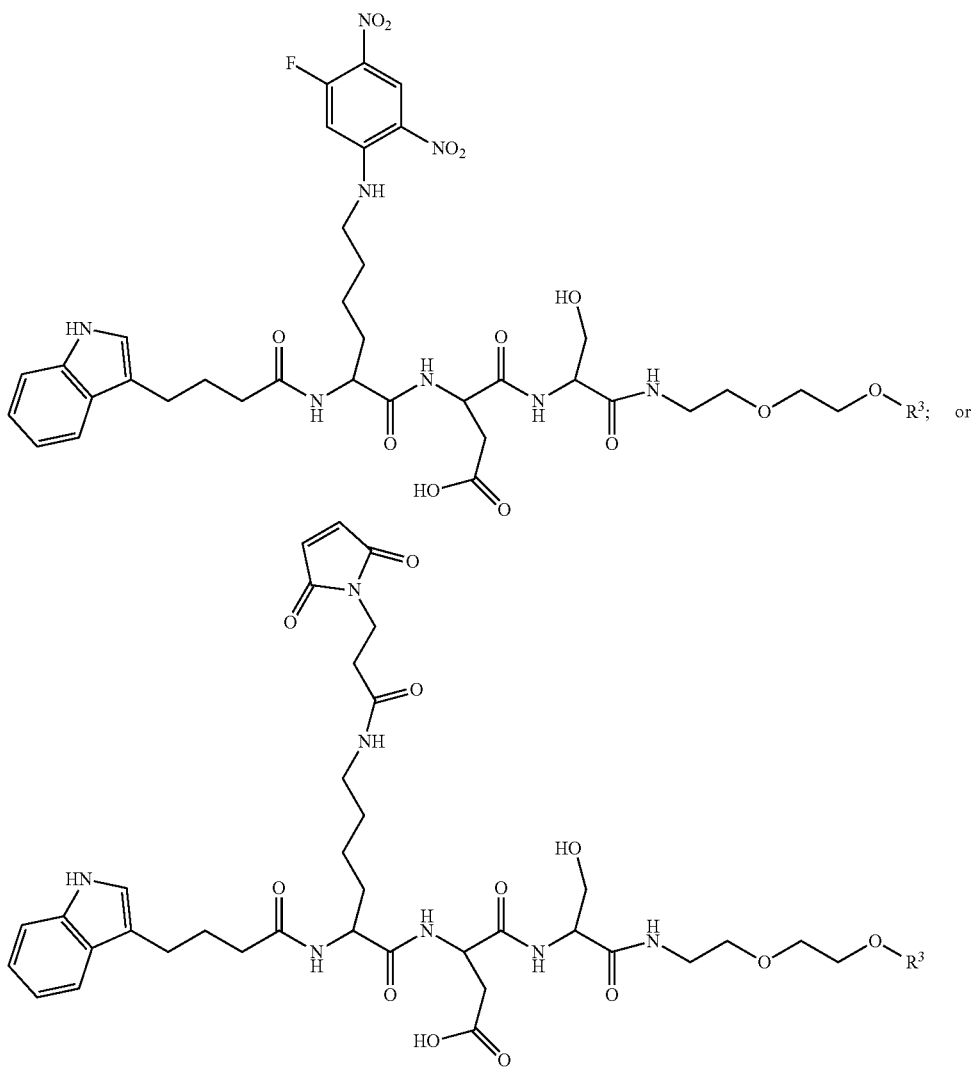

b) incubating the reaction mixture of a) for at least about 0.25 h at a temperature of from about 4° C. to about 37° C.; c) removing unbound molecular payload by dialysis or size exclusion chromatography; d) raising the pH of the reaction mixture to about 8.5, under conditions suitable to form a covalent bond between the antibody and the molecular payload by adding a basic solution containing 0.1 M sodium bicarbonate pH 8.5, 0.1 N NaOH or 0.1 N NH$_4$OH; and e) incubating the reaction mixture of d) for at least about 0.25 h at a temperature of from about 4° C. to about 37° C. In some cases, the molar excess of molecular payload to nucleotide binding pockets of the antibody is, or is about, 1.1-fold, 2-fold, 2.5-fold, 3-fold, 4-fold, 5-fold, or more.

In some cases, the R$^3$ of the molecular payload contains a conjugating agent that contains an alkyne or azide and the method further includes: f) introducing into the reaction mixture a copper (I) catalyst and an active agent comprising an azide or alkyne that is reactive to the alkyne or azide of the conjugating agent, thereby conjugating the active agent to the conjugating agent. In some cases, the R$^3$ of the molecular payload contains a conjugating agent that contains a 1,2-dihydroxybenzene moiety, and the method further includes: f) introducing into the reaction mixture an active agent comprising a boronic acid that is reactive to the 1,2-dihydroxybenzene moiety of the conjugating agent, thereby conjugating the active agent to the conjugating agent.

EXAMPLES

The following examples are offered to illustrate, but not to limit the claimed invention.

Example 1

Experimental Methods
General Procedures
The chemicals and solvents used were of analytical grade and were received from commercial sources. Fmoc-protected amino acids were purchased from Advanced ChemTech (Louisville, Ky.), EMD Chemicals Inc. (Gibbstown, N.J.), and Chem-Impex International, Inc. (Wood Dale, Ill.). TentaGel S NH$_2$ (90 μm, 0.27 mmol/g) was purchased from Rapp Polymere Gmbh (Tubingen, Germany). Indole-3-butyric acid and 1,5-difluoro-2,4-dinitrobenzene were from Sigma Aldrich (St. Louis, Mo.).

Library Design and Synthesis

To aid in the design of the library, computer-modeling studies were done. We started by performing molecular docking studies using Autodock v4.2[19] to understand the binding of indole-3-butyric acid to trastuzumab. The three-dimensional structure of human trastuzumab available in PDB (ID: 1N8Z) was used for all docking studies. From the low energy binding conformations calculated by the indole-trastuzumab docking, the spatial and charge properties were identified. This knowledge was used to design several virtual test ligands of varying lengths and charge properties. These ligands were docked with trastuzumab using Autodock v4.2[19]. Trastuzumab and ligand structures were prepared for docking using Autodock Tools[19] package. Partial atomic charges were assigned to the ligands using the Gasteiger-Marsili method, and after merging of non-polar hydrogens; rotatable bonds were assigned using Autodock Tools. Water molecules were removed from the trastuzumab structure; the missing hydrogen atoms and Kollman partial charges were added. Further, non-polar hydrogen atoms were merged to their corresponding carbons. A grid size of 60×60×60 with grid spacing of 0.375 Å for smaller ligands was used, and for larger ligands the grid size was increased proportionally to fit the whole ligand molecule. We used the Lamarckian Genetic Algorithm (Pseudo Solis-Wets Algorithm[20]) to perform 256 independent docking runs with default parameters in Autodock. Cluster analysis was performed on docked results using RMS tolerance of 2 Å. The results were analyzed to compare the lowest energy binding energy conformations.

Further, to test for the binding specificity profile, blind docking runs were performed using these test ligands, and trastuzumab as the target protein. The SwissDock webservice[21] was used to conduct these blind dockings. Energy optimized structure of the ligands was calculated using Merck Molecular Force Field (MMFF)[22] as implemented in Marvin Suite v 5.11. Among the clusters generated by SwissDock, top clusters were analyzed and compared to check for convergence on the binding site. These top clusters were then used to design several one-bead-one-compound (OBOC) combinatorial libraries to identify an optimal crosslinking compound to the NBP.

Library Screen/Confirmation Screen

Approximately 100,000 library beads were immobilized onto 30 mm polystyrene dishes by using a series of 90% DMF washes. Beads were then washed and swelled in PBS. Nonspecific binding was inhibited with blocking buffer (0.1% BSA, 0.1% Tween, and 0.05% sodium azide) for one hour in room temperature. After several PBS washes, 1 ng/ml trastuzumab (Genentech, South San Francisco, Calif.) in PBS (pH 7.0) was added and was placed in a rotating incubator at 37° C. for 1 hour. Here, we used trastuzumab as the model monoclonal antibody. Excess antibody was removed, and beads were gently washed with PBS. To facilitate crosslinking of DNDFB to the antibody of the peptide library, we raised the pH to 8.5 for one hour. After crosslinking, beads were washed sequentially with PBS, 1.00 mM pH 3 glycine, and then pH 8 TBS. Anti-human IgG-alkaline phosphatase conjugate was then added at 1:1000 dilution. After washing, beads were then developed using BCIP (5-bromo-4-chloro-3'-indolyphosphate p-toluidine salt) solution. (NBT (nitro-blue tetrazolium chloride) was not used due to high background staining with TentaGel library beads.) Using a dissecting microscope, plates were imaged and positive beads were isolated. The isolated beads were then treated with 8M guanidine/HCl to remove all non-covalently linked proteins. The beads were further washed with PBS and water. Beads were decoded using Edman degradation chemistry (ABI Precise 494 Protein Sequencer).

In the confirmation studies, hits were synthesized on TentaGel. Staining steps were the same except 1:30 anti-human IgG conjugated to Cy3 was used to allow for fluorescence quantification. Beads were imaged with Olympus IX2-IX2-UCB (Center Valley, Pa.) under 4× objective. Cy3 excitation and emission settings were used. Bead intensity was measured and quantified using Image J.

Western Blot

50 µM DS peptide was incubated with 10 µM trastuzumab at 37° C. for 1 hr in a shaking incubator. Samples were then dialyzed to remove unbound peptides, with frequent water changes. Crosslinking occurred by increasing the sample to pH 8.5 and incubated for 1 hr at room temperature. 50 ng of each sample was loaded onto 10% SDS-PAGE gel with Laemelli loading buffer containing β-mercaptoethanol. Denatured, reduced samples were run @140 V. Proteins were then transferred to PVDF membrane at 100 V. Membranes were washed with TBST and were blocked with blocking buffer for 1 hr in room temperature. After a series of PBS washes, 1:500 streptavidin-alkaline phosphatase was added to the membrane and incubated for 1 hr. Blots were developed using BCIP/NBT (Promega, Madison, Wis.). Similar western blots were done using bevacizumab (Genentech/Roche, South San Francisco, Calif.), rituximab (Biogen IDEC, Cambridge, Mass.), cetuximab (Bristol-Myers Squibb, New York, N.Y.), and intravenous immunoglobulin (BDI Pharma, Columbia, S.C.).

Papain Digestion

The biotinlyated DS affinity element was conjugated with several FDA-approval therapeutic antibodies, including trastuzumab, IVIG, rituximab, and cetuximab. The affinity element and the antibody were incubated at 37° C. for an hour followed by room temperature incubation with 1.4 µL 7N ammonia hydroxide for 1 hour. These biotinylated immunoconjugates were then digested with papain to generate Fab and Fc fragments. Fragments were then separated on a 4% to 12% Tris-glycine gel (Life Technologies, Inc., Gaithersburg, Md.) and transferred to PVDF membranes. Blots were probed with streptavidin-Horseradish Peroxidase (HRP) (BioRad, Hercules, Calif.), which would have a strong binding affinity with biotinlyated affinity element. Blotting was carried out in 10% non-fat milk solution. Fragments were visualized using enhanced chemiluminescence reagents (GE health Care, Buckinghamshire, UK). Commassie Brilliant Blue G-250 (Thermo, UK) staining was performed at the same time on a separated gel with the same samples.

HABA-Avidin Quantification

Biotinylated antibody conjugates were prepared as described in previous sections. The absorbance of HABA/Avidin premix solution (pierce) was measured at 500 nm. The biotinylated proteins were mixed with HABA/Avidin premix solution for 30 minutes at room temperature. Absorbance measurements were measured again at the same wavelength. Calculations of moles of biotin per mole of protein used the following formula:

$$A\lambda = \varepsilon \lambda bC, \text{ (Beer's Law)}$$

where A is the absorbance of the sample at a particular wavelength (λ). The wavelength for the HABA assay is 500 nm. ε is the absorptivity or extinction coefficient at the wavelength (λ). For HABA/avidin samples at 500 nm, B is the cell path length of the microplate reader (Molecular Devices, Sunnyvale, Calif.) expressed in centimeters. C is the concentration of the sample expressed in molarity. Moles of biotin per mole of protein is calculated by: mmol biotin from the sample/mmol protein in original sample.

Size-Exclusion HPLC

Samples were prepared as mentioned for western analysis. Trastuzumab-biotinylated peptide conjugates were then incubated with neutravidin at different molar ratios (4:1, 10:1, 30:1 trastuzumab conjugate:neutravidin) for 1 hr. Samples were then run on Waters size exclusion HPLC (Milford, Mass.), with Superdex200 (10/300) column from GE Healthcare (Pittsburgh, Pa.). Area under the curve (AUC) was then measured to quantify the amount of successful conjugation. Peaks were compared to a known control sample.

Cell Culture

Jurkat human T-lymphocyte, SKBR-3 MCF-7, and MDA-MB-468 human mammary gland/breast adenocarcinoma cells were purchased from American Type Culture Collection (ATCC; Manassas, Va.). SKBR-3 cells were cultured McCoy5A. Medium with 10% fetal bovine serum (FBS), 100 U/ml penicillin G, and 100 µg/ml streptomycin. Jurkat, MCF-7 and MDA-MB-468 cells were cultured in RPMI-1640 Medium with 10% FBS 100 U/ml penicillin, 100 µg/ml streptomycin. All cells were cultured at 37° C. using a humidified 5% $CO_2$ incubator.

Flow Cytometry $10 \times 10^5$ cells (SKBR-3, MCF7, and MDA-MB-468) were plated. Trastuzumab-peptide crosslinker was prepared as previously mentioned. Trastuzumab-peptide conjugate and/or biotinylated MMAE were then conjugated to avidin at 1:3, 2:2, and 3:1 molar ratio. Cells were dosed with 40 ng/mL modified or naked antibodies for 2 hours at 37° C. Cells were trypsinized, washed with PBS, and incubated with anti-human IgG Fc Cy3 secondary antibody (Thermo, Waltham, Mass.) for 1 hour on ice in the dark. Cells were then washed with cold PBS and resuspended for flow cytometry analysis using a FACScan system (Becton Dickinson, San Jose, Calif.).

Cells (breast carcinomas SKBR-3, trastuzumab insensitive breast cancer line MCF7 and antigen negative breast cancer cell line, MDA-MB-468 (100,000 cells per sample) were incubated at 37° C. with 40 ng/ml conventional or DS conjugated trastuzumab for 2 hrs in 2 mL total volume. After this incubation, cells were washed and then incubated with anti-human IgG Fc Cy3 secondary antibody (1 h on ice in dark). PBS+1% FBS+2 mM EDTA were used as dilution buffer for secondary antibody. Cells were then washed and analyzed by flow cytometry (Becton Dickinson, San Jose, Calif.).

$3 \times 10^4$ cells (SKBR-3 and Jurkat) were plated in a 48 well plate. Trastuzumab-peptide crosslinker was prepared as previously mentioned. Trastuzumab-peptide conjugate and/or biotinylated. LLP2A were then conjugated to SAPE at 4:1 molar ratio. The bispecific samples were conjugated at 3:1:1 molar ratio (trastuzumab-peptide:LLP2A:SAPE). Cells were dosed with (1) 750 nM Trastuzumab-peptide, (2) 250 nM LLP2A, or (3) 750 nM Trastuzumab-peptide/LLP2A conjugate for 1 hr. SKBR-3 cells were trypsinized; Jurkat cells were removed. All cells were washed with cold PBS and resuspended in PBS for flow cytometry analysis using the FACScan system (Becton Dickinson, San Jose, Calif.).

Cryo Electron Microscopy

The Trastuzumab-peptide crosslinker conjugate was prepared as previously mentioned. Prior to crosslinking, the sample was dialyzed to remove any unbound peptide. Antibody-peptide conjugates were mixed with streptavidin nanogold (Nanoprobes, Yaphank, N.Y.) at 3:1 ratio for 20 min. After optimizing sample concentration, 3 µl of aliquot of specimen was applied on carbon-coated copper grids that had been glow discharged and then stained with 2% uranyl acetate. The specimen was examined under a JEM-2100 transmission electron microscope (JOEL, Peabody, Mass.) and images were recorded on a TVIPS 4x4 CCD camera TemCam-F415, Gauting, Germany) with a step size of 1.2 Å at the specimen space.

Results and Discussion

The increasing interest in antibody drug conjugates and bispecific antibodies presents great need for site specific linkers to control conjugation to antibodies. Here, we present a small molecule peptide crosslinker that has the ability to covalently conjugate to an amino acid within or near the nucleotide binding pocket located in the Fab portion of monoclonal and polyclonal antibodies (IgG, IgE, etc.). This simple conjugate allows for the addition of ligand or a toxic payload to be easily adapted for the emergence of antibody drug conjugates or bispecific antibodies.

Design and Screening of a Peptide Library

The design of a site-specific conjugation peptide is based on targeting the nucleotide-binding pocket (NBP) in IgG antibodies. In our studies, trastuzumab was used as the model monoclonal antibody. Based upon previous molecular modeling data[22] and the Fab domain crystal structure of trastuzumab[30], we located the NBP with H101, H103 and L36 as the amino acids interacting with indole-3-butyric acid. In this NBP, numerous lysine residues were found surrounding the indole-3-butyrate binding site (FIGS. 1a, b). Based upon this structural characteristic, a small library of compounds was examined (Table 1, FIG. 12) by comparing the docking conformations and energies to the NBP. Taking advantage of the lysine residues located within this NBP, we expected to have enhanced affinity of indole-3-butyrate to the NBP by including negatively charged amino acids in the library (Table 2). The energy characterizations obtained from Autodock[25] indicated that the crosslinker located on the lysine directly next to indole-3-butyric acid was preferred over other conformations (Table 1). Compounds with amino acids between the indole-3-butyrate and Lys(crosslinker) had less optimal mean cluster binding energies. Results of this in silico screen predicted that indole-3-butyrate-Lys(acrylic acid)-Glu would bind with the highest affinity to the NBP. Using this knowledge, we designed eight OBOC libraries to screen for compounds with enhanced affinity and crosslinking ability to the NBP.

TABLE 1

Figure 12:
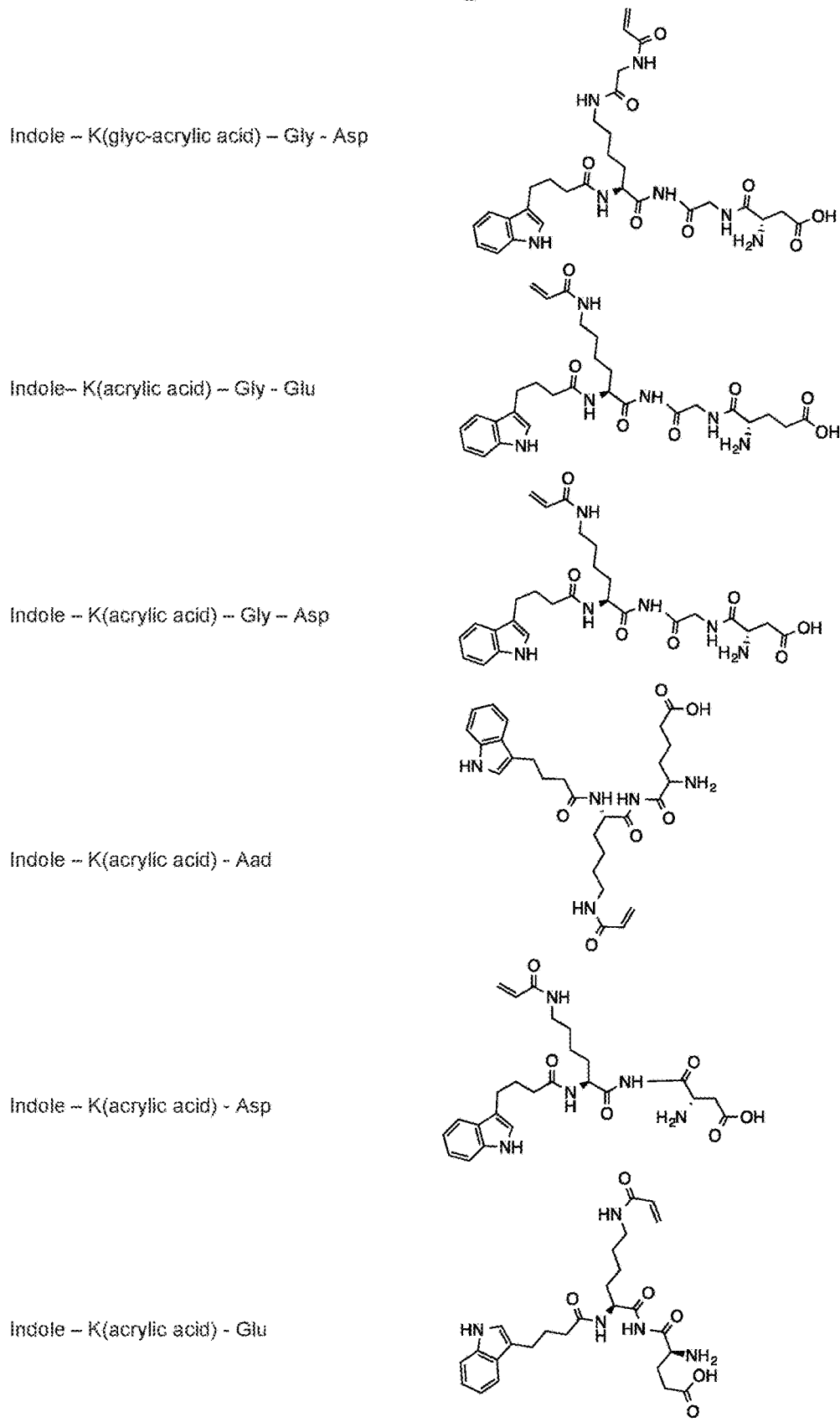
FIG. 12. Test compounds used for computational modeling.

Energy calculations derived from computer modeling of test compounds used in Autodock. Lowest energy indicates the predicted binding energy by Autodock. All crosslinkers are located in ε-amine of lysine unless otherwise denoted. Structures of test compounds are depicted in FIG. 12

| Targeting compound | $X_1$ | $X_2$ | $X_3$ | Lowest Binding Energy (kcal/mol) | Mean Cluster Binding Energy (kcal/mol) |
|---|---|---|---|---|---|
| Indole | K(xlinker) | | | −6.69 | −5.28 |
| Indole | K(xlinker (α-amine)) | | | −6.97 | −5.82 |
| Indole | P | K(xlinker) | | −5.14 | 0.48 |
| Indole | G | K(xlinker) | | −5.47 | −1.99 |
| Indole | P | G | K(xlinker) | −3.18 | 5.37 |
| Indole | K(xlinker) | D | | −5.8 | −4.86 |
| Indole | K(G-xlinker) | G | D | −5.34 | −1.78 |
| Indole | K(x-linker) | E | | −6.68 | −5.78 |

TABLE 1-continued

Energy calculations derived from computer modeling of test
compounds used in Autodock. Lowest energy indicates the
predicted binding energy by Autodock. All crosslinkers are
located in ε-amine of lysine unless otherwise denoted.
Structures of test compounds are depicted in FIG. 12

| Targeting compound | $X_1$ | $X_2$ | $X_3$ | Lowest Binding Energy (kcal/mol) | Mean Cluster Binding Energy (kcal/mol) |
|---|---|---|---|---|---|
| Indole | K(xlinker) | Aad | | −5.49 | −2.81 |
| Indole | K(xlinker) | G | D | −5.79 | −2.42 |
| Indole | K(xlinker) | G | E | −5.11 | −3.61 |

TABLE 2

Amino acids used in the library

| Ala | Phe | Aic | Nva |
| Asn | Pro | Ana (Nov-1) | Orn HCl |
| Asp | Ser | Bpa | Phe(3-Cl) |
| Gln | Thr | Cha | Phe(4-Me) |
| Glu | Trp | Chg | Phe(diCl) |
| Gly | Tyr | Dpr | Phg |
| His | Val | HoCit | Tyr(diI) |
| Ile | 4-Apc | HoPhe | |
| Leu | Acpc | Nal-2 | |
| Met | Alb | Nle | |

Figure 13:
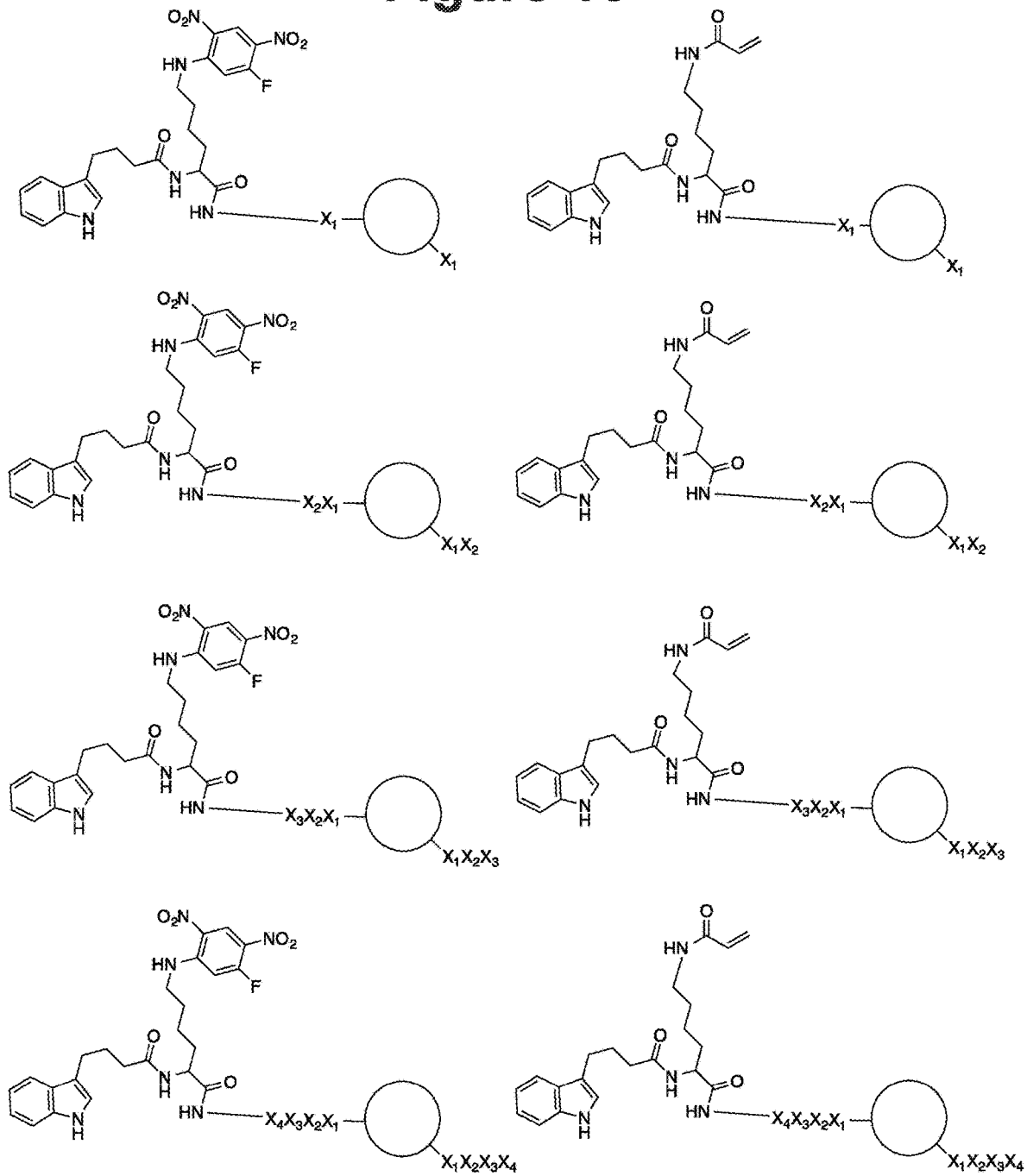
FIG. 13. Libraries synthesized for combinatorial screens.
Figure 14:
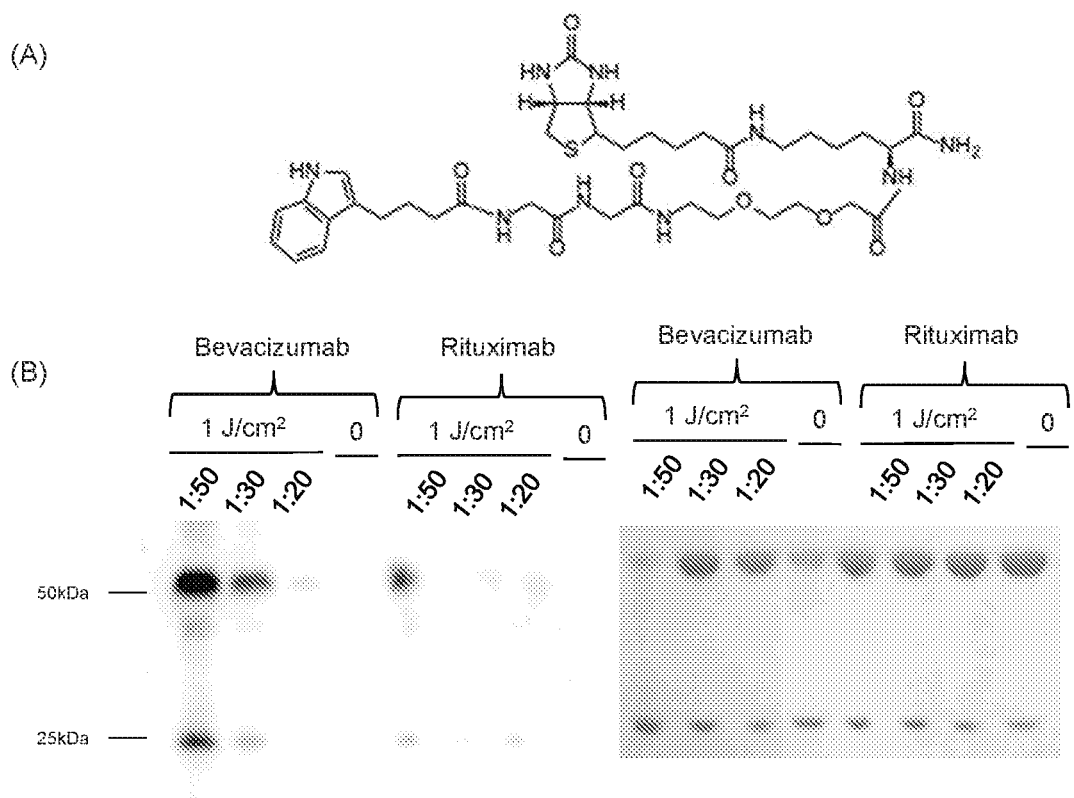
FIG. 14. The crosslinking ability of an indole based photocrosslinker (A) without any additional cross-linking agent or affinity element was analyzed using clinically approved antibodies (rituximab and bevacizumab). This compound was conjugated to antibodies through UV light to initiate the photocrosslinking process. (B) The conjugation was observed only under 1:50 ratio between ligand and antibody at the highest energy level (1 J/cm$^2$) among all the antibodies.
Figure 15:
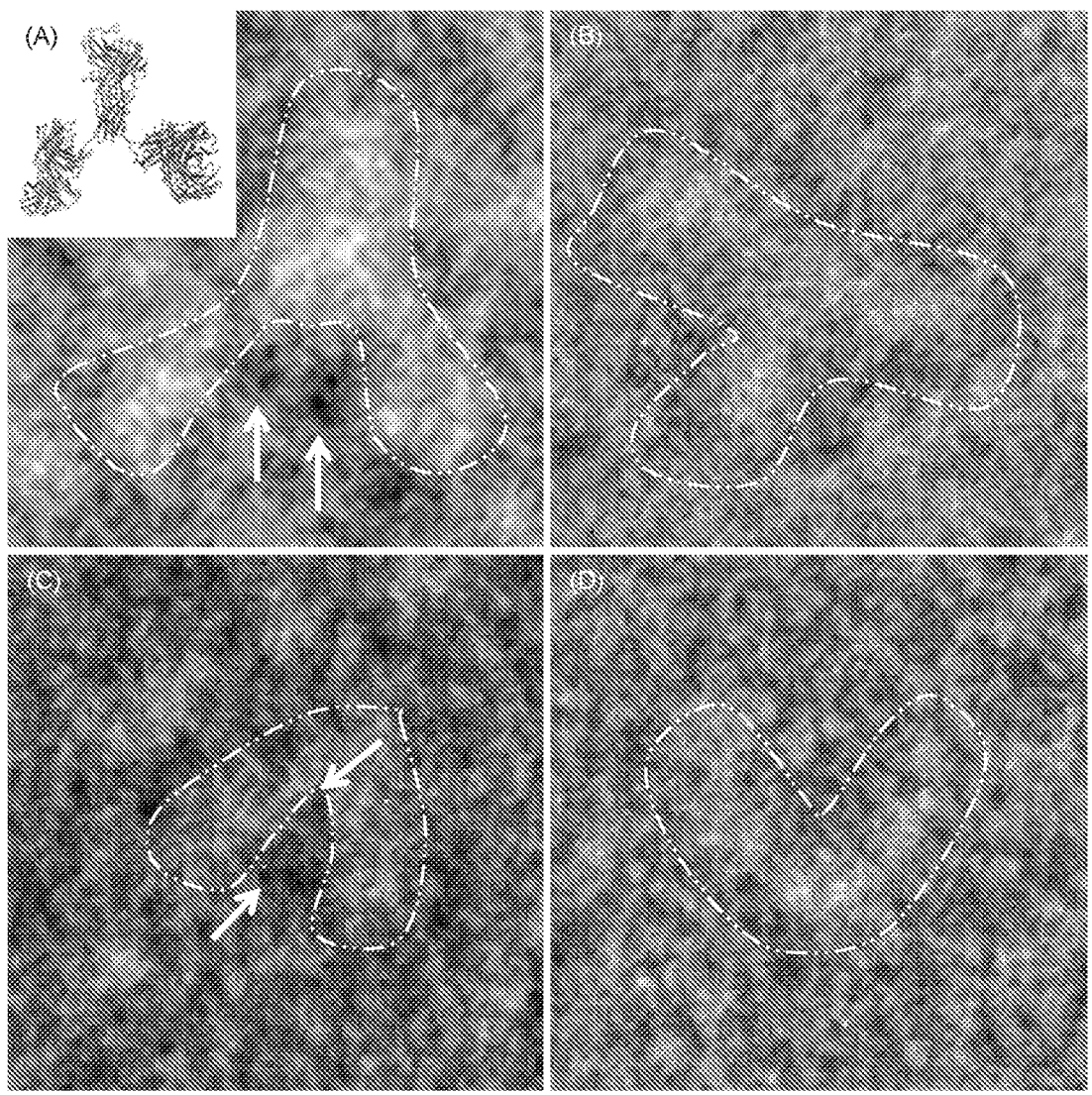
FIG. 15. CryoEM images to depict site specific ligation to NBP. The dotted lines outlines the antibody. (A) represents trastuzumab labeled with nanogold, indicated by arrows. Inset represents the IgG structure (pdb code 3CM9.pdb). The gold particle is about 2-3 pixel in size. The IgG molecule appeared as three-domain structure with gold particle residing on top of the domain joint. Each domain is about 60 Å in length suggesting that the IgG molecule (65 Å) is in a slightly tilted orientation. Two nanogold particles are seen on each of the F(ab) arms. (B) represents an IgG antibody without any labeling. (C) TrastDS conjugate was digested with pepsin to obtain f(ab)2 fragments and labeled with nanogold. (D) represents an unlabeled fragment.
Figure 16:
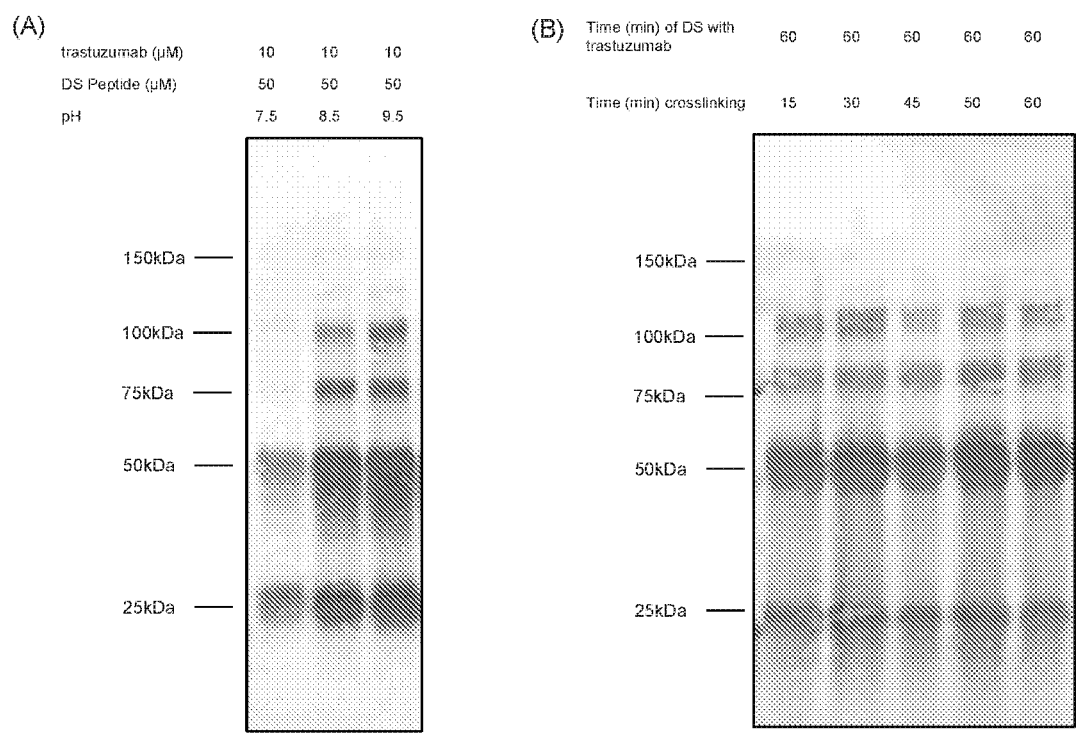
FIG. 16. (A) Differences in conjugation were seen when pH was increased, with no differences in product seen at pH 8.5 or 9.5. (B) 10 µM DS peptide was incubated with 50 µM trastuzumab for 1 hour at 37° C. Different crosslinking times were tested.

Libraries based on the results of the in silico screens were synthesized on TentaGel beads using a split-mix technique[31]. $KX_1$, $KX_1X_2$, $KX_1X_2X_3$, and $KX_1X_2X_3X_4$ libraries N-capped by "indole-butyrate-Lys(crosslinker)" were synthesized with the combination of unnatural and L-amino acids (FIGS. 1c, 13, Table 2). The variable portions of the libraries were synthesized using the split mix technique. Indole-3-butyric acid and 1,5-difluoro-2,4-dinitrobenzene (DNDFB) were then coupled to the lysine side chain. We first tried acrylic acid and cyanuric chloride as the covalent crosslinker; however, these crosslinkers resulted in very high background, which made screening difficult (data not shown). In lieu of these more traditionally used crosslinkers, Marquez[24] showed that DNDFB is a mild electrophile that can be used to cross-link naturally occurring proteins via primary amines. With the displacement of the first fluorine with the compound to generate DNFB, the reactivity of the remaining fluorine is significantly lowered allowing for its efficient use in biological applications[24]. Covalent crosslinking of DNDFB or DNFB to a primary amine is very efficient under slightly basic conditions, making this crosslinker very easy to use and can be broadly used in various therapeutic immunoglobulin conjugates.

Figure 3:
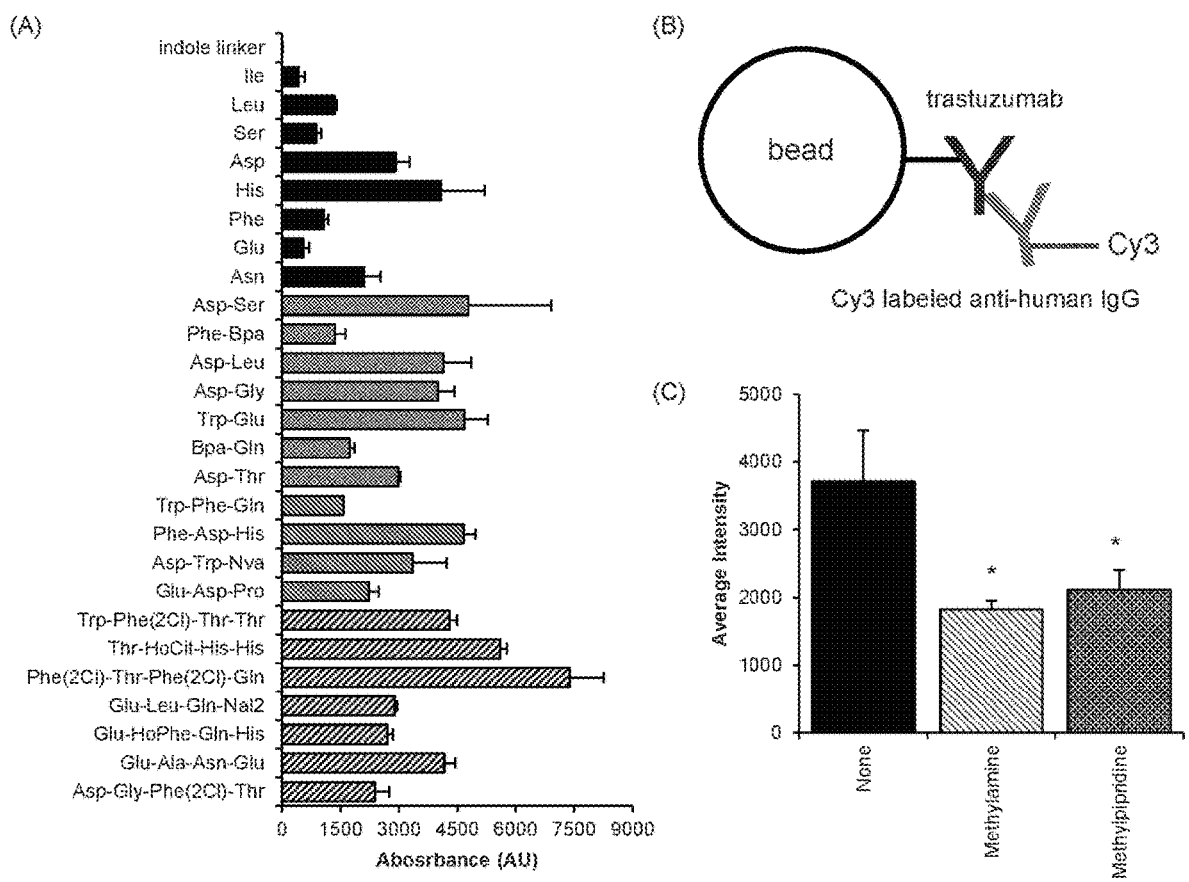
FIG. 3. (A) All of the hits identified in the library screen were resynthesized on TentaGel. Trastuzumab was added to the beads, washed, and allowed to crosslink by increasing the pH to pH 8.5. Nonbinding antibodies were washed away with acidic glycine buffer (pH 3.0). Anti-human Cy3 IgG was added to the beads to bind to trastuzumab. Beads were then imaged and quantified using Image J. Average intensity of beads were taken. (B) Describes the overall concept of the bead staining. (C) The DNFB on Asp-Ser beads were reacted with methylamine or methylpypridine prior to staining with antibodies. The 50% decrease in fluorescent intensity indicates the decreased ability for the quenched crosslinker to react with trastuzumab. * $P<0.05$.

In order to identify beads that covalently crosslink trastuzumab, we have modified our previously reported enzyme-linked colorimetric screening method[32]. After incubating trastuzumab with the DNDFB modified bead library at pH 8, we treated the beads with acidic glycine (pH 3.0) buffer to ensure that only covalently linked trastuzumab will remain on the bead. The covalently linked antibody was then detected with anti-human antibody-alkaline phosphatase conjugate followed by the BCIP substrate, Peptide-beads turned green and were physically isolated for microsequencing (FIGS. 1d, 3). All of the DNDFB modified libraries were screened multiple times, ensuring that ~90% of the members in all forms of the libraries were screened.

Several trends were observed from the positive hits (FIG. 3a). Asp and Phe (including its unnatural amino acid derivatives) appears frequently in all forms of the library. In the peptides without Asp, other negatively charged amino acids are found. Multiple Lys residues in the NBP favor the identification of negatively charged amino acids. Although our computational analysis concluded that negatively charged amino acids was the best fit for the NBP, our library included all natural amino acids. Despite this, most of the hits identified consisted of negatively charged amino acids, confirming our original hypothesis.

The positive sequences were resynthesized in solid state on TentaGel beads to compare the crosslinking abilities between all of the positive hits (FIG. 3a,b). Similar incubation times and washes were performed as the screening process. After the acidic glycine wash, anti-human IgG conjugated to Cy3 was used to detect the crosslinked trastuzumab. From this assay, several indole-butyrate-Lys (DNFB)-derivatized dipeptides with Asp, Glu, and Phe (2Cl)-Thr-Phe(2Cl)-Gln were found to have superior crosslinking abilities compared to other hits and our negative control (indole-K(DNFB) without peptide). These results were consistent with the results found in the computer-modeling data.

In order to understand if the indole-butyrate-peptides were merely a strong binding agent to the NBP or if DNFB was utilized to covalently crosslink with free amines in the NBP, indole-butyrate-peptides were reacted with methylamine and methyl-piperidine. These highly basic compounds react with the free fluorine in DNFB making the peptide compound unreactive and unable to crosslink to the NBP of the immunoglobulin (FIG. 3c). Using similar crosslinking incubation times and staining procedures as the reconfirmation assay, the beads displayed decreased Cy3 intensity when the indole-butyrate-Lys(DNFB)-Asp-Ser linker (DS affinity element) reacted with the highly basic compounds, indicating the crosslinking ability of the DS peptide to IgG.

Peptide Crosslinker Characterization

Figure 2:
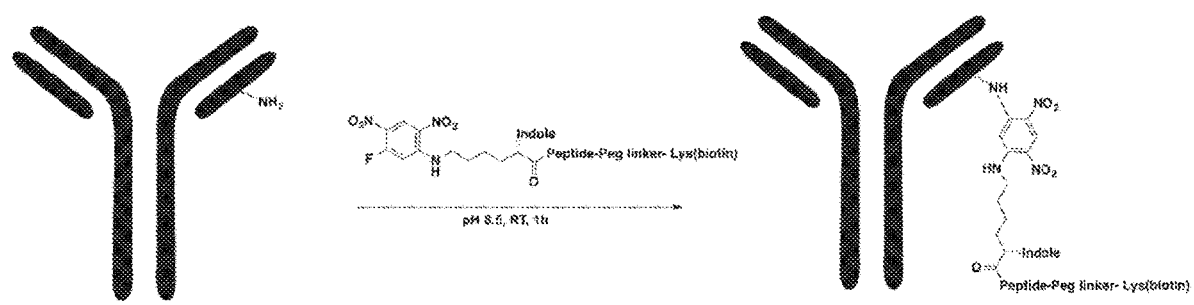
FIG. 2. Indole-3-butryic acid directs the peptide to the nucleotide binding pocket (NBP) where free amines reside. At slightly basic pH, DNFB reacts with the several free amines within this binding pocket which allows covalent ligation peptide to bind to the free amines located within the NBP.
Figure 4:
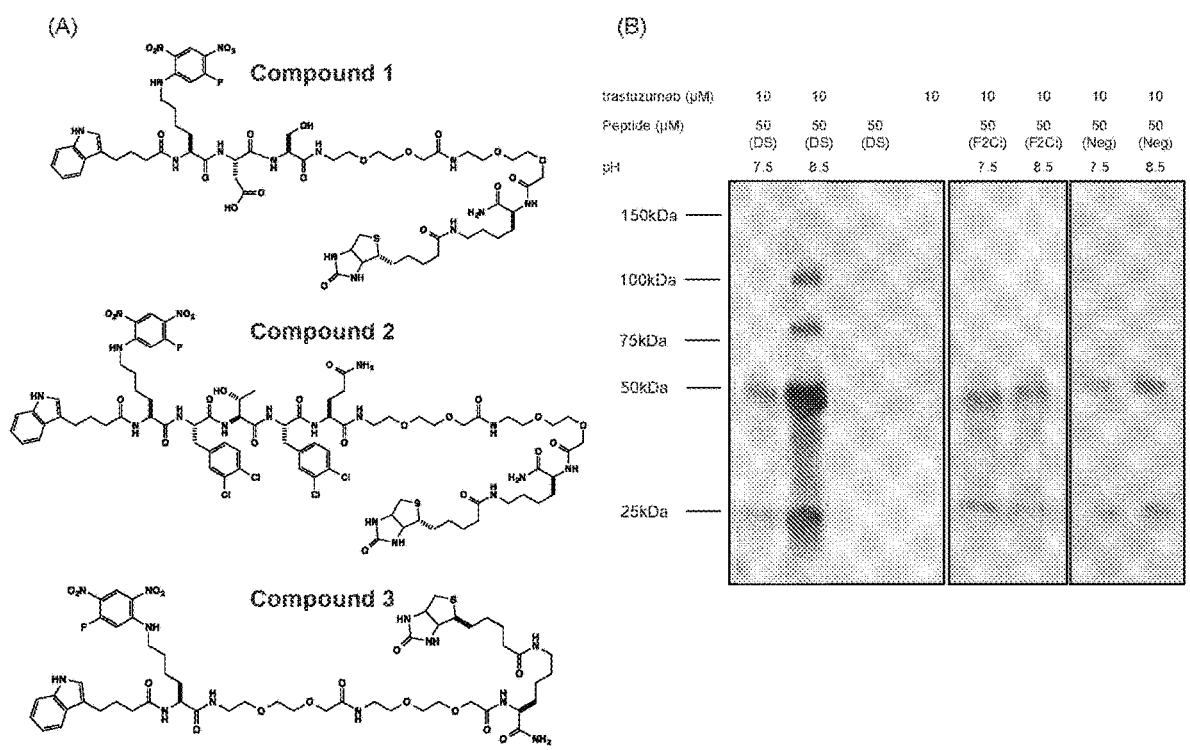
FIG. 4. (A) Structure of soluble peptides DS (1), Phe (2Cl)-T-Phe(2Cl)-Q (2, F(2Cl)), and Negative control (3) used in solution phase experiments. (B) Western blot analysis with solution phase peptides (DS—Lane 1 and 2, F(2Cl)—Lane 5 and 6, Neg—Lane 7 and 8). When pH was increased to 8.5, an increase in product for the DS sample was observed. Some product is still seen at pH 7.5 due to peptide specificity to the nucleotide binding pocket and mild reactivity at pH 7.5. No differences, however, were seen with Phe(2Cl). Same amount of product was observed in both pH 7,5 and 8.5. Free peptide and free trastuzumab, as predicted, was negatively stained.

To understand the site specificity of our peptide to the NBP, the top two hits (DS affinity element 1 and F(2Cl)-T-F(2Cl)-Q affinity element 2) from the reconfirmation studies were resynthesized in soluble biotinylated form (FIG. 4a). Here, the affinity element is a part of the indole-K(DNFB)-peptide-peg linker-K(biotin) molecule. A negative control peptide (compound 3) without the amino acids peptide sequence was also synthesized. PEG linkers were added between the indole-peptide and biotin to maintain peptide binding and crosslinking ability. The peptide-linker reaction chemistry is shown in FIG. 2. Reducing, denaturing conditions were employed for Western blot analysis to confirm the covalent reactions and to obtain distinguishable bands between unreacted IgG and the cross-linked IgG (FIG. 4b). After 1 hour incubation of 50 μM of peptide crosslinker with 10 μM trastuzumab at pH 7.5, crosslinking was then introduced by raising the pH to 8.5. Biotin-tagged peptide-antibody conjugates were detected at 25 kDa and 50 kDa for all 3 affinity elements, representing covalent ligation to both the heavy and light chains (FIG. 4b). This is expected as residues from both chains form the NBP. Controls (antibody alone and peptide alone) did not show any bands at any molecular weight. The promising hit F(2Cl)-T-F(2Cl)-Q affinity element (2) showed similar results as our negative control (3) (FIG. 4b), Where no differences were observed among the different pH. The faint bands at pH 7.5 indicate some reactivity of DNDFB at neutral pH. DS affinity element (1), however, showed a surprising and dramatic increase of product at pH 8.5. This addition of Asp and Ser is thus proven to dramatically increase the amount of peptides capable of binding to NBP. These results indicate that affinity element is a superior peptide linker that adds superior binding specificity to the targeting moiety and that the addition of DNFB as a cross-linking agent can allow for optimal conjugation to the NBP.

Figure 5:
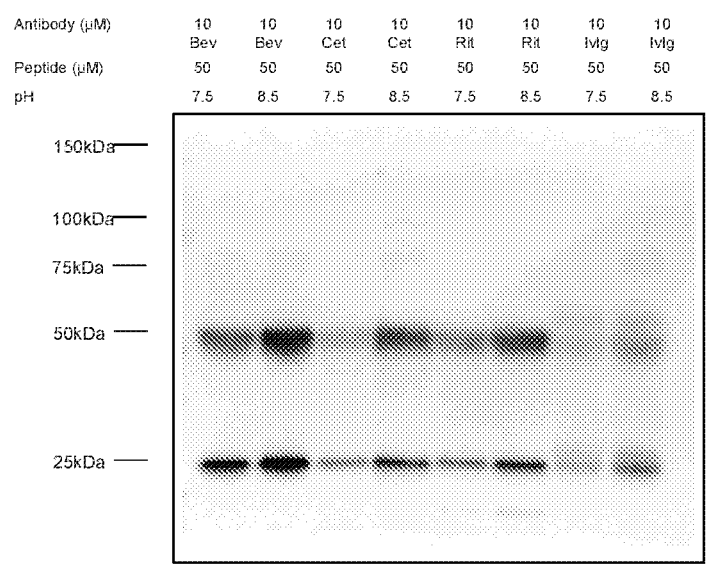
FIG. 5. Western blot analysis with DS was performed with bevacizumab (Bev). cetuximab (Cet), retuximab (Rit), and IVIG. When pH was increased to 8.5, we observed an increase in product for the DS sample. Some product is still seen at pH 7.5 due to peptide specificity to the nucleotide binding pocket and mild reactivity at pH 7.5.
Figure 6:
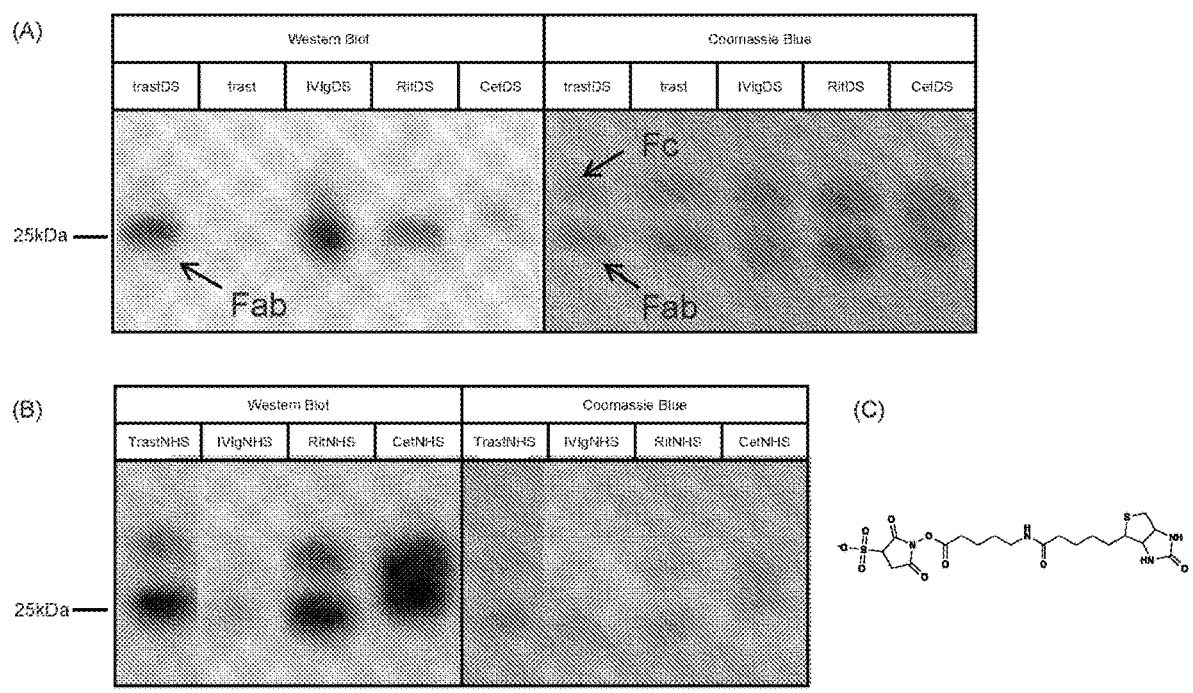
FIG. 6. (A) Papain digestion was performed on trastuzumab conjugated with DS, trastuzumab only, IVIG conjugated with DS, rituximab conjugated with DS, and cetuximab conjugated with DS. Samples were then reduced. In the western blot, only the Fab fragment was identified while both Fc and Fab fragments were seen in the coomassie blue gel. (B) The same experiment was done with sulfo-NHS-biotin where conjugation occurred with both Fab and Fc fragments. (C) Structure of sulfo-NHS-biotin.
Figure 7:
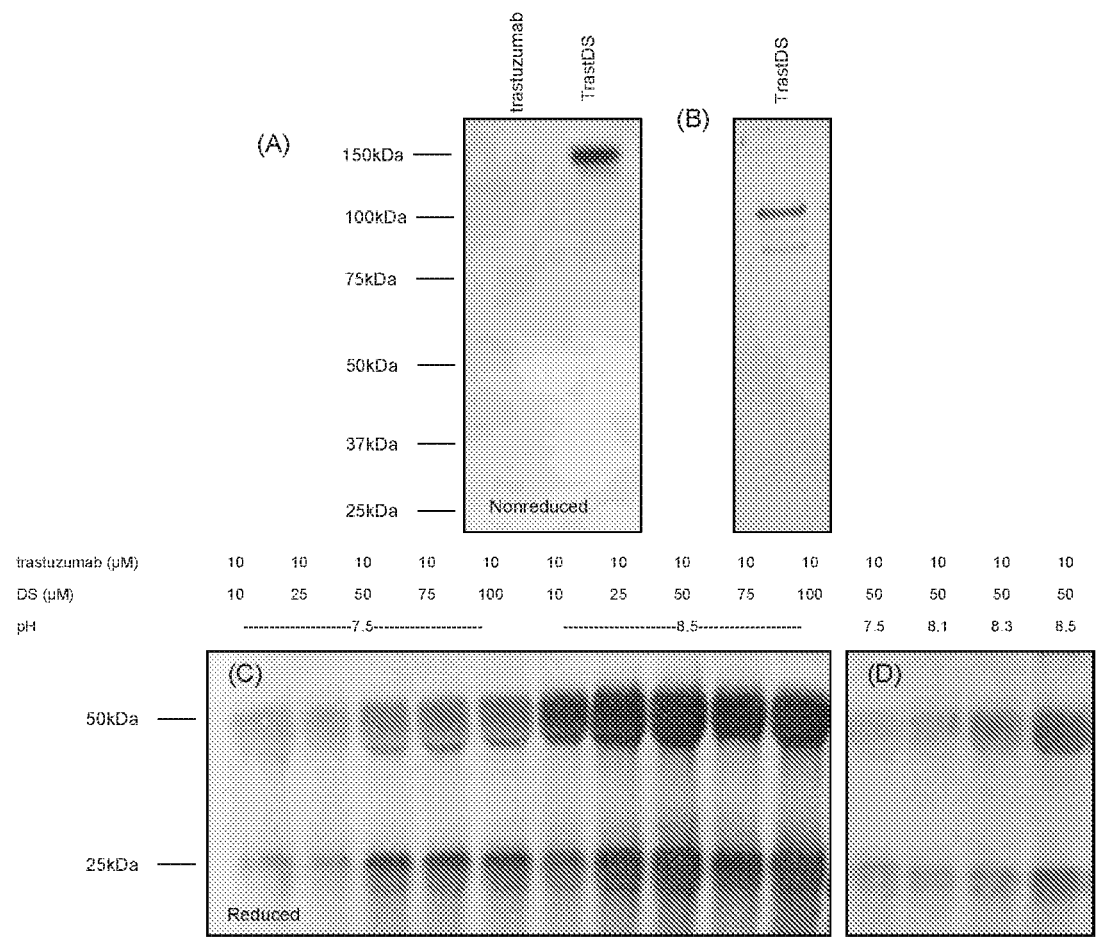
FIG. 7. (A) Western blot analysis of antibody peptide conjugate under nonreducing conditions. One band was found at 150 kDa indicating a homogenous product. (B) Antibody peptide conjugate was formed as previously mentioned. Conjugates were then digested with pepsin. It is noted that ligation occurred only at F(ab)2 fragment. (C) Western blot analysis of soluble DS peptide. At increasing molar ratio, increased product was observed at both pH 7.5 and pH 8.5. At ratios above 2.5:1 peptide: trastuzumab, no additional products were produced. (D) Differences in conjugation was seen when pH was increased, with most products identified at pH 8.5.
Figure 8:
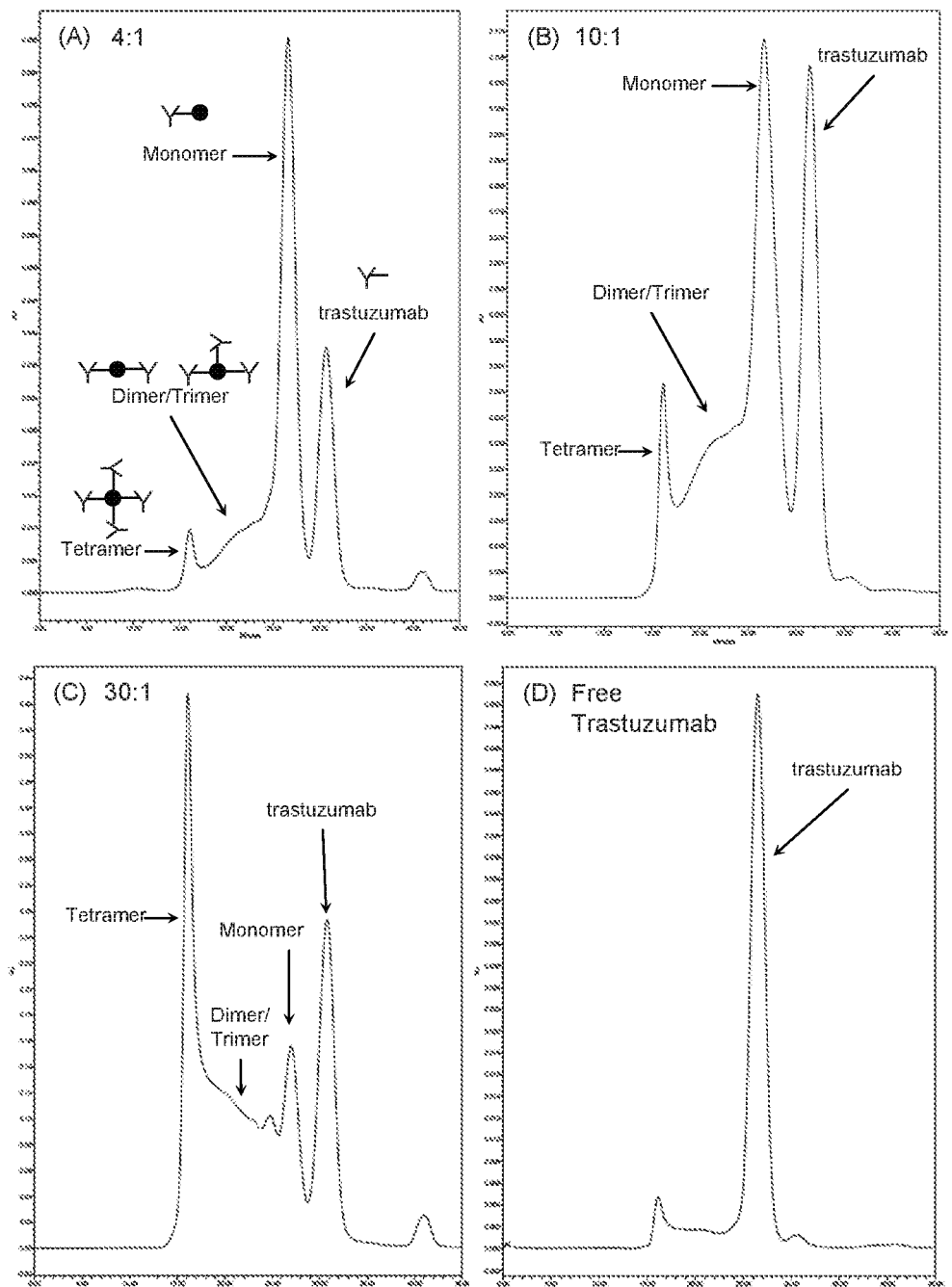
FIG. 8. Size exclusion HPLC was used to estimate the conjugation efficiency of DS peptide to trastuzumab. After conjugating DS to the antibody (trastDS), the sample was dialyzed to remove unbound peptide. TrastDS was then incubated with neutravidin at different ratios, 4:1 (A), 10:1 (B), and 30:1 (C) for 1 hour and analyzed on a gel filtration column, (D) represents trastuzumab with no neutravidin. The percentage of peptide that is able to conjugate to trastuzumab was determined by analyzing the area under the curve. Percent of peptide conjugated=area of neutravidin conjugates/total area. Neutravidin conjugates include monomer, dimer, trimer, and tetramer. It was estimated that 79% of the trastuzumab was contain the conjugated peptide.

The same western blot analysis was performed with bevacizumab, cetuximab, rituximab, and IVIG. Similar results were seen with these antibodies when affinity element 1 was added (FIG. 5) indicating the broad application of our peptide linker. However, decreased activity was seen with cetuximab when compared to bevacizumab, rituximab and WIG suggesting that DS affinity element is not optimal for the NBP in cetuximab. Alves[33,34] discovered a indole-3-butryic acid based linker that utilizes UV photocrosslinking to covalently conjugate to the NBP. Due to the lack of peptide sequence to improve specificity, this conjugate requires an increased ratio of linker to antibody for efficient crosslinking (FIG. 14).

Site Specificity Characterization

Classical peptide mapping techniques were first used to determine the linker conjugation site using trypsin and chymotrypsin for protein digestion of the separated heavy and light chain. Unlike other site specific conjugation linkers which modified one specific amino acid[35,36], our peptide linker has the ability to ligate to several free amines that are located within or near the NBP. Similar to results previously found by Wang[37], this was problematic for the identification of exact modifications sites since these peptides produced weak MS signals, which are not suitable for this type of analysis.

In order to determine site specificity of the novel ligation strategy, we conjugated the DS peptide-biotin to several immunoglobulins, including trastuzumab, IVIG, rituximab, and cetuximab. These immunoconjugates were digested with papain and then further reduced to generate Fab and Fc fragments, which could be resolved on SDS-PAGE. In all of the antibody conjugates, only the Fab portion (FIG. 6*a*), but not the Fe portion was biotinylated. This is expected since indole-6-butyric acid has binding specificity against the Fab fragment. In a control experiment, we used a sulfa-NHS-biotin, a nonspecific amine reactive reagent (FIG. 6*c*), to derivatize the same set of antibodies and found that both Fab and Fc fragments were labeled (FIG. 6*b*). Together, this data prove that our ligation strategy is general, site-specific, ligates to the Fab portion of the immunoglobulin only, and can be applied even to polyclonal IVIG. This indicates the broad application of the DS peptide where it can be applied to site-specifically ligate directly to the Fab in many clinical antibodies without the need to reengineer an antibody and without the use of harsh chemical agent, which is a significant improvement to current site-specific crosslinking technology.

Using cryo-electron microscopy, we further imaged our immunoconjugate (FIG. 15) by incubating the antibody conjugate with 5.6 nm streptavidin-nanogold and then performed cryo-electron microscopy. We were able to visualize nanogold (1.4 nm) binding to only the inner arms of IgG, at positions next to both Fab arms (FIG. 15*a, b*). It appeared that there were two residing sites for nanogold on each Fab arm. One of the nanogolds is localized to the variable domain, which is the known location of the NBP. The other nanogold was located near the constant domain. The distance between two resident sites is about 6 nm; suggesting the flexibility of the peptide and the multiple conjugation sites on streptavidin, as well as the difference of the binding orientation in respect to Fab arm, because the EM image is a two-dimensional projection. The second conjugation site, which appeared to be at the constant domain, can be bound to the NBP but its location in the EM image is a result of the flexibility of the peptide and streptavidin conjugation. It should be noted that no binding was seen in the Fc arm or on the outer portion of the Fab further demonstrating consistency of site-specific conjugation. These two sites were also observed when F(ab)2 fragments were imaged. The nanogold was again found at positions close to the variable domain (FIG. 15*c,d*). In all cases, the nanogold is at a distance equivalent to one streptavidin from the Fab arm again confirming the site specificity provided by the combination of the indole targeting moiety and the peptide affinity element. These imaging studies were repeated and similar results were obtained (data not shown).

Our antibody-linker conjugate (trast-DS) produced a homogenous conjugate (FIG. 7*a*) on a nonreducing SDS-PAGE gel indicating no loss of interchain disulfide bonds through peptide conjugation as seen in some site specific conjugates. With the abundance of primary amines on IgG, DNDFB and DNFB can potentially randomly react with any of the primary airlines on the surface of the antibody. The absence of additional products indicates that conjugation did not occur randomly but was site-specific. The trast-DS conjugate was digested with pepsin and covalent ligation was maintained in the F(ab)2 arms (FIG. 7*b*). Again, a homogenous product was seen, further indicating the low probability of nonspecific binding.

The reactivity of DS affinity element was further investigated to explore optimal conditions for the crosslinking reaction. The optimal pH of the reaction was studied as shown in FIG. 7*d*. After 1 h the bands had increasing intensity as the pH was increased from 7.5 to 8.5 with the most products seen in 8.5. Beyond pH 8.5, no additional products were found (FIG. 16*a*). We further analyzed the optimal time for conjugation. Within 15 minutes of increased pH there is no difference in the amount of product created (FIG. 16*b*). In order to understand the efficacy of our peptide, we used different ratios of DS peptide to trastuzumab to discover the most efficient combination (FIG. 7*c*). It was observed that at molar ratios above 2.5 DS peptide: 1 trastuzumab, no additional products were seen on the western blot analysis. This saturability of binding further proves the site specificity of the targeting moiety affinity element combination. Through these optimization steps, it was found that at a 2.5:1 molar ratio of compound to antibody is sufficient for efficient ligation at pH 8.5 in 15 minutes.

We further analyzed our antibody conjugate by quantifying the number of peptide linker conjugated to each antibody. The antibodies conjugated to biotinylated DS affinity element were subjected to quantitative assay with a biotin quantification assay (Table 3). Free avidin was mixed with 4'-hydroxyazobenzene-2-carboxylic acid (HABA) that forms a complex that is a yellow chromophore with molar extinction coefficient 34000 $M^{-1}.cm^{-1}$ at 500 nm, However, biotin has much higher binding coefficient towards avidin than that of HABA. When biotin conjugated materials are mixed with the HABA-avidin complex, biotin replaces HABA to give a biotin-avidin complex that barely absorbs light at 500 nm. Thus, the chromophore concentration decreases. By measuring the absorbance difference at 500 nm using UV-Vis spectroscopy, the number of avidin-accessible biotin can be calculated. Using this method, we estimated that ~2 DS affinity elements were attached to each antibody, which corresponds to the two NBP that are found within each monoclonal IgG antibody. This number of conjugates per antibody is similar to other known site-specific antibodies[2,38,39,40]. As expected, the nonspecific sulfo-NHS-biotin conjugate can randomly react with different lysine side chains on the surface of the antibodies tested.

TABLE 3

This table indicates the number of the biotin per monoclonal antibody. Using a HABA-avidin complex with our conjugated biotinylated antibodies, the difference in absorbance at 500 nm is proportional to the number of biotin per antibody. Our DS peptide retains the site specificity that has an average biotin per antibody ratio between 1 and 3, whereas the positive control, NH2- reactive biotin to monoclonal antibodies, has an average of 5 to 8 biotin molecules conjugates to each antibody.

|  |  | mAb-NHS | mAb-DS | mAb | avidin-HRP |
|---|---|---|---|---|---|
| Bevacizumab | # of biotin | 4.47 | 2.3 | 0 | 1.401 |
| Cetuximab | # of biotin | 7.98 | 2.77 | 0 | 1.401 |
| Rituximab | # of biotin | 6.58 | 2.1 | 0 | 1.401 |
| IVIG | # of biotin | 9.09 | 2.21 | 0 | 1.401 |
| Trastuzumab | # of biotin | 6.33 | 1.6 | 0 | 1.401 |

An important factor to understand is the crosslinking efficiency of the indole:DS peptide:DNFB containing compound to trastuzumab. The tract-DS-biotin conjugate was generated as described above and incubated with neutravidin at 4:1, 10:1, and 30:1 ratios. Using size exclusion chromatography, the percentage of peptide that is able to conjugate to trastuzumab was determined. Comparing to a standard, we were able to determine the free trastuzumab, monomer (1 trastuzumab antibody, DS-biotin, and neutravidin), dimer/trimer (2-3 trastuzumab antibodies, 2-3 DS-biotins, and neutravidin), and tetramers (4 trastuzumab antibodies, 4 DS-biotins, and neutravidin) that were created by mixing trast-DS-biotin with neutravidin. Using area under the curve (AUC) to estimate the relative amount of each Ab-neutravidin complex, the number of free trastuzumab to the various conjugated forms was extrapolated. The reaction between affinity element and immunoglobulin was highly efficient with 79% of the antibodies crosslinked (FIG. 8a-d) when 5 molar excess of peptide to trastuzumab was used. The lack of absolute conjugation efficiency can result from peptides incorrectly oriented in the binding site thereby limiting the access of DNFB to the free amines within the NBP.

In Vitro Characterization

Figure 17:
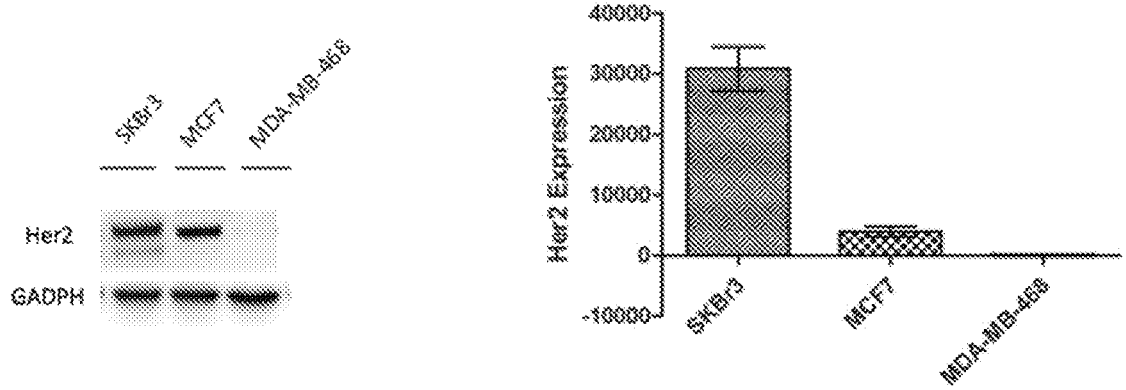
FIG. 17. (A) 30 µg protein from whole cell lysate (SKBr3, MCF7 and MDA-MB-468) were performed for Her2 expression level detection. (B) Band intensities were quantified through Image Lab 5.0 Software.

The site-specific ligation of a nucleotide binding pocket ligand targeting moiety in combination with a peptide affinity element containing linker and a cross-linking agent has broad utility. For example, cytotoxins can be easily conjugated to the C-terminus of the peptide affinity element, e.g., directly or through one or more ethylene glycol linker moieties, for the production of ADCs. As another example, ligands can be easily conjugated to the C-terminus of the peptide affinity element, e.g., directly or through one or more ethylene glycol linker moieties, to create bispecific antibodies. We demonstrated the ability of the targeting moiety, affinity element, cross-linking agent combination to be applied to other clinical antibodies thereby proving its application for many disease applications. Conjugation of a compound to the NBP which has close proximity of to the antigen binding site is a cause of concern. This proximity has the potential to affect the antigen binding ability. We tested the Trast-DS conjugate for binding to SKBR3, MCF7, and MDA-MB-468 cells. SKBR3 cells have a high expression of Her2 receptors, MCF7 cells have moderate Her2 expression, while MDA-MB-468 cells do not have Her2 expression (FIG. 17), The antigen binding ability of Trastuzumab and Trast-DS was confirmed using flow cytometry. (FIG. 9a-c).

By detection with Cy3 labelled anti-human IgG secondary antibody, Trast-DS did not display any fluorescent shift. TrastDS-MMAE, an immunotoxin generated through our conjugation method also retained the antigen binding ability (FIG. 9d-f). Both Her2 expressing cell lines showed similar binding affinity and specificity to the unmodified antibody.

Figure 10:
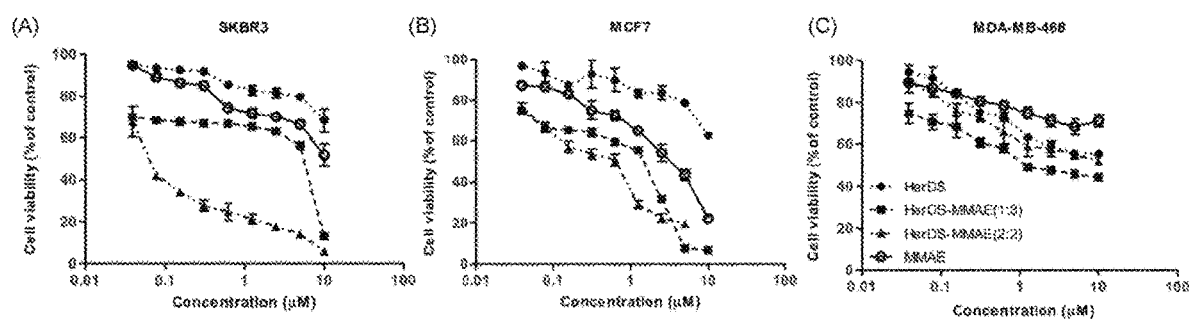
FIG. 10. Cells (A: SKBR3; B:MCF7; C:MDA-MB-468) were incubated with TrastDS conjugated with MMAE, at either 1:3 or 2:2 ratio. In cell lines with HER2 expression, SKBR3 and MCF7, a decreased in cell viability was seen in antibodies with MMAE conjugation. In the cell line lacking HER2 expression, MDA-MB-468 this effect was not as pronounced.

In order to determine the ability of the DS affinity element to serve as a conjugate linker, trast-DS was conjugated with biotinlyated MMAE with neutravidin thereby creating a cytotoxic mAb (FIG. 10). Anti-Her2-trastuzumab conjugated with MMAE were tested on Her2-expressing breast cancer cells for cytotoxicity (MCF7 cells and SKBR3 cells) and Her2 negative cells (MDA-MB-458) for selectivity. Cell viability of the three cell lines was compared with controls (neutravidin-biotin-MMAE complex and Trast-DS) and TrastDS-MMAE conjugates. SKBR3 and MCF7 cells showed decreased cell viability in a dose dependent manner compared to MDA-MB-468 cells, which was not significantly affected by the MMAE conjugation. Due to the valine-citrulline linker attached to the biotin-MMAE, the free drug is released only when biotin-MMAE complex is internalized[38]. This was confirmed when severe cytotoxicity was not observed in all three cell lines with the avidin-biotin-MMAE control. However, trastDS conjugates showed increased cytotoxicity in SKBR3 and MCF7 cells proving that MMAE (an antineoplastic agent) is effectively entering the cell in the Her2(+) cells and inhibiting the assembly of microtubule. This difference is likely resulting from the increased binding of trastuzumab to Her2(+) cells and the internalization of the cytotoxic antibody conjugate. It should be noted, however, MDA-MB-468 displayed some levels of nonspecific cytotoxicity. The immunoconjugates depicted a certain extent of receptor dependent cytotoxicity and provides a proof of concept that our site-specific conjugation technique serves as a good platform for target delivery of cytotoxic reagents. This technology can be applied to other conjugates, such as radioactive ligand conjugates or immunomodulin molecule conjugates.

Figure 11:
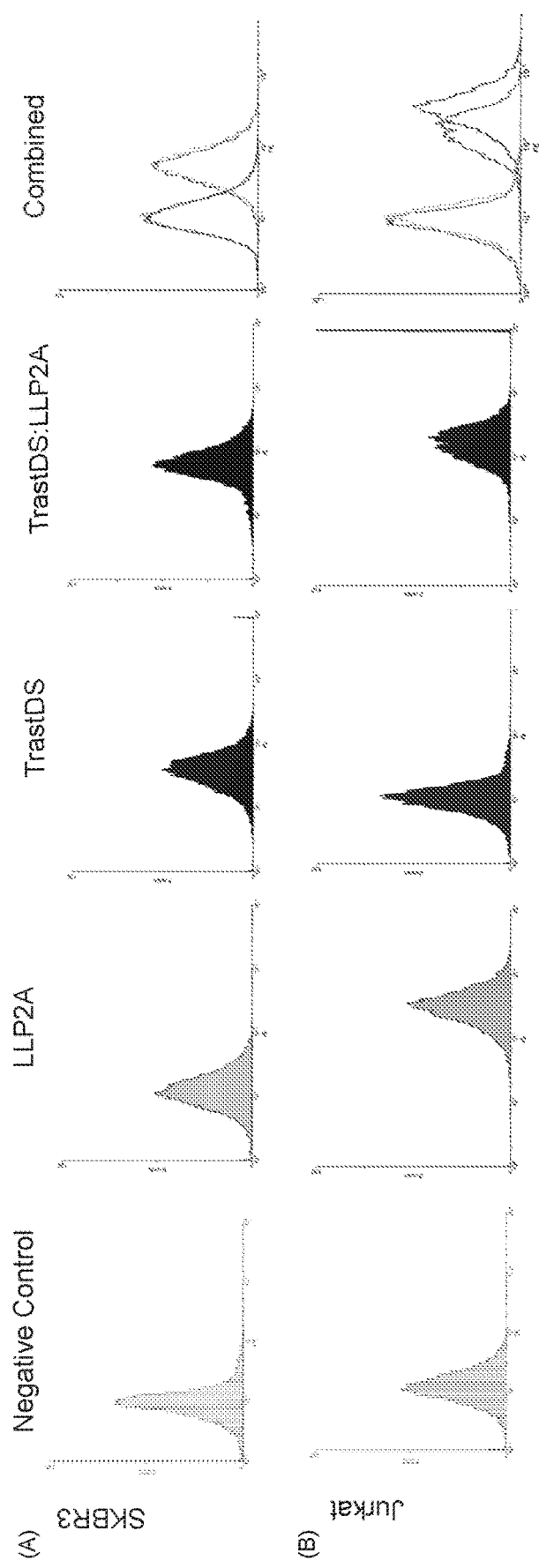
FIG. 11. Bispecific binding abilities for both Her2 and α4β1 integrin are shown. Biotinylated DS peptide was conjugated to trastuzumab creating trast-DS. Trast-DS was dialyzed and crosslinked at pH 8.5. 3:1 ratio of trast-DS to biotinylated LLP2A was bound to streptavidin-PE (SAPE). Controls (trast-DS only and LLP2A only) were conjugated to SAPE at a 4:1 molar ratio. 750 µM trast-DS, 750 µM trast-DS: LLP2A, 250 µM LLP2a were incubated with SKBR-3 human mammary gland/breast adenocarcinoma (A) and Jurkat human T lymphocyte (B) cells for 1 hour. Cells were run through flow cytometry to quantify cells.

We conjugated a ligand to the C-terminus of a compound containing a targeting moiety (e.g., indolyl), cross-linking agent (e.g., DNFB), and affinity element containing linker (e.g., DS-peptide), thereby creating a mAb that targets two antigens. In order to understand the multi-targeting ability of our IgG conjugate, trastDS was incubated with biotinylated LLP2A[41] and streptavidin PE (SAPE) at 3:1:1 ratio (trastDS: LLP2A: SAPE), LLP2A is a peptidomimetic compound with the ability to bind to α4β1 integrin on Jurkat cells. We added this TrastDS/LLP2A conjugate at 750 μM to SKBR-3 and Jurkat cells (FIG. 11) for 1 hr. The TrastDS/LLP2A conjugate was able to bind to both Jurkat and SKBR-3 cells. No loss of affinity was seen with SKBR-3 cells but some binding affinity was lost with the Jurkat cells, which may have resulted from the steric hindrance created from the antibody as measured by flow cytometry. Meanwhile, the control trastuzumab peptide bound only to SKBR-3 cells and not Jurkat cells. Similarly, the control LLP2A only bound to Jurkat cells and saw no binding with SKBR-3 cells. Here we have confirmed the bispecific nature of our compound that through the use of the peptide can produce binding to streptavidin, The TrastDS:LLP2A compound can be utilized to facilitate delivery of NK cells and T-cells to the tumor site for immunotherapy.

Conclusion

With the increased interest in covalent conjugation to antibodies, much effort has been placed into this technology to site-specifically control conjugation of a therapeutic payload to monoclonal antibodies producing homogeneous products. Heterogeneity in conjugation to antibodies results in toxicity and antibody instability[2]. We exploited previous knowledge on NBP reported by Rajagopalan et al[20] by employing OBOC combinatorial chemistry and novel screening strategy to develop NBP targeting compound that contains a targeting moiety and a linker containing a dipeptide affinity element in combination with a cross-linking agent. This targeting compound can site-specifically ligate therapeutic pay-load to the two NBPs on an antibody molecule, or an NBP containing antibody fragment. Through proximity ligation, the compound can be covalently linked to the immunoglobulin through the built-in dinitrofluorobenzene cross-linking agent, under very mild conditions, where 79% of antibodies are crosslinked within 15 minutes. This conjugation results in a homogenous product that does not affect the thiol stability of the antibody, which is unseen with other nonspecific chemical crosslinkers. Although the indole-Lys(DNFB)-Asp-Ser-containing compound can efficiently derivatize IVIG, it is less efficient with Centuximab. This indicates that more than one, and perhaps a few affinity elements and/or targeting moiety combinations may be needed to cover the NBPs of the entire spectrum of immunoglobulins. Therapeutic payloads can be introduced to the immunoglobulins via two general approaches: (i) direct site-specific ligation to antibody NBPs of a compound conjugated to a therapeutic payload, or (ii) site-specific ligation of azide-derivatized affinity element, followed by introduction of therapeutic payload via click chemistry[13].

Compared to other site-specific covalent modifications, this technique is mild, highly efficient, and can be used for many clinically available antibodies. This technique is simple and should be readily scalable, thereby shortening optimization time and can be quickly adapted for manufacturing antibody drug conjugates or bispecific antibodies. One unique feature of this antibody conjugation strategy is that it can be applied to polyclonal antibodies such as IVIG, making it possible to introduce pathogen-specific ligands to IVIG, generating neutralizing antibodies against infectious microbes, such as the Ebola virus.

REFERENCES (1) Carter, P. *Nature Reviews Cancer* 2001, 1, 118.

(2) Junutula, J. R.; Raab, H.; Clark, S.; Bhakta, S.; Leipold, D. D.; Weir, S.; Chen, Y.; Simpson, M.; Tsai, S. P.; Dennis, M. S.; Lu, Y. M.; Meng, Y. G.; Ng. C.; Yang. J. H.; Lee, C. C.; Duenas, E.; Dorrell, J.; Katta, V.; Kim, A.; McDorman, K.; Flagella, K.; Venook, R.; Ross, S.; Spencer, S. D.; Wong, W. L.; Lowman, H. B.; Vandlen, R; Sliwkowski, M. X.; Scheller, R. H.; Polakis, P.; Mallet, W. *Nat. Biotechnol.* 2008, 26, 925.

(3) Wu, A. M.; Seiner, P. D. *Nat. Biotechnol.* 2005, 23, 1137.

(4) Verma, S.; Miles, D.; Gianni, L.; Krop, I. E.; Welslau, M.; Baselga, J.; Pegram, M.; Oh, D. Y.; Dieras, V.; Guardino, E.; Fang, L.; Lu, M. W.; Olsen, S.; Blackwell, K.; Grp, E. S. *N. Engl. J. Med.* 2012, 367, 1783.

(5) de Clare, R. A.; McGinn, K.; Kwitkowski, V.; Bullock, J.; Khandelwal, A.; Habtemariam, B.; Ouyang, Y. L.; Saber, H.; Lee, K.; Koti, K.; Rothmann, M.; Shapiro, M.; Borrego, F.; Clouse, K.; Chen, X. H.; Brown, J.; Akinsanya, L.; Kane, R.; Kaminskas, E.; Farrell, A.; Pazdur, R. *Clin. Cancer Res.* 2012, 18, 5845.

(6) Beck, A.; Haeuw, J. F.; Wurch, T.; Goetsch, L.; Bailly, C.; Corvaia, N. *Discov. Med.* 2010, 53, 329.

(7) Axup, J. Y.; Bajjuri, K. M.; Ritland, M.; Hutchins, B. M.; Kim, C. H.; Kazane, S. A.; Halder, R.; Forsyth, J. S.; Santidrian, A. F.; Stafin, K.; Lu, Y. C.; Tran, H.; Seller, A. J.; Biroce, S. L.; Szydlik, A.; Pinkstaff, J. K.; Tian, F.; Sinha, S. C.; Felding-Habermann, B.; Smider, V. V.; Schultz, P. G. *Proc. Natl. Acad. Sci. U.S.A.* 2012, 109, 16101.

(8) Graziani, E. I.; Tumey, L. N. In *Biotherapeutics: Recent Developments Using Chemical and Molecular Biology;* Jones, L. H., McKnight, A. J., Eds.; Royal Soc Chemistry: Cambridge, 2013, p 145.

(9) Shen, B. Q.; Xu, K. Y.; Liu, L. N.; Raab, H.; Bhakta, S.; Kenrick, M.; Parsons-Reponte, K. L.; Tien, J.; Yu, S. F.; Mai, E.; Li, D. W.; Tibbitts, J.; Baudys, J.; Saadi, O. M.; Scales, S. J.; McDonald, P. J.; Hass, P. E.; Eigenbrot, C.; Nguyen, T.; Solis, W. A.; Fuji, R. N.; Flagella, K. M.; Patel, D.; Spencer, S. D.; Khawlil, L. A.; Ebens, A.; Wong, W. L.; Vandlen, R.; Kaur, S.; Sliwkowski, M. X.; Scheller, R. H.; Polakis, P.; Junutula, J. R. *Nat. Biotechnol.* 2012, 30, 184.

(10) Hofer, T.; Thomas, J. D.; Burke, T R.; Rader, C. *Proc. Natl. Acad. U.S.A.* 2008, 105, 12451.

(11) Witus, L. S.; Moore, T.; Thuronyi, B. W.; Esser-Kahn, A. P.; Scheck, R. A.; Iayarone, A. T.; Francis, M. B., *J. Am. Chem. Soc.* 2010, 132, 16812.

(12) Witus, L. S.; Netirojjanakul, C.; Palla, K. S.; Muehl, E. M.; Weng, C. H.; Iavarone, A. T.; Francis, M. B. *J. Am. Chem. Soc.* 2013, 135, 17223.

(13) Ban, H.; Gavrilyuk, J.; Barbas, C. F. *J. Am. Chem. Soc.* 2010, 132, 1523.

(14) Gavrilyuk, J.; Ban, H.; Nagano, M.; Hakamata, W.; Barbas, C. F. *Bioconjugate Chem.* 2012, 23, 2321.

(15) Josten, A. E.; Haalck, L.; Spener, F.; Meusel, M. *J. Immunol. Methods* 2000, 240, 47.

(16) Kamiya, N.; Takazawa, T., Tanaka, T.; Ueda, H.; Nagamune, T. *Enzyme Microb. Technol.* 2003, 33, 492.

(17) Mindt, T. L.; Jungi, V.; Wyss, S.; Friedli, A.; Pla, G.; Novak-Hofer, I.; Grunberg, J.; Schibli, R. *Bioconjugate Chem.* 2008, 19, 271.

(18) Gilmore, J. M.; Scheck, R. A.; Esser-Kahn, A. P.; Joshi, N. S.; Francis, M. B. *Angew. Chem.-Int. Edit.* 2006, 45, 5307.

(19) Woodnutt, G.; Violand, B.; North, M. *Curr. Opin. Drug Discov. Dev.* 2008, 11, 754.

(20) Rajagopalan, K.; Pavlinkova, G.; Levy, S.; Pokkuluri, P. R.; Schiffer, M.; Haley, B. E.; Kohler, H. *Proc. Natl. Acad. Sci. U.S.A.* 1996, 93, 6019.

(21) Alves, N. J.; Mustafaoglu, N.; Bilgicer, B. *Biosens. Bioelectron.* 2013, 49, 387.

(22) Handlogten, M. W.; Kiziltepe, T.; Moustakas, D. T.; Bilgicer, B. *Chem. Biol.* 2011, 18, 1179.

(23) Alves, N. J.; Stimple, S. D.; Handlogten, M. W.; Ashley, J. D.; Kiziltepe, T.; Bilgicer, B. *Analytical Chemistry* 2012, 84, 7721.

(24) Marquez, B. V.; Beck, H. E.; Aweda, T. A.; Phinney, B.; Holsclaw, C.; Jewell, W.; Tran, D.; Day, J. J.; Peiris, M. N.; Nwosu, C.; Lebrilla, C.; Meares, C. F. *Bioconjugate Chem.* 2012, 23, 1080.

(25) Morris, G. M.; Huey, R.; Lindstrom, W.; Sanner, M. F.; Belew, R. K.; Goodsell, D. S.; Olson, A. J. *Journal of Computational Chemistry* 2009, 30, 2785.

(26) Solis, F. J.; Wets, R. J. B. *Math. Oper. Res.* 1981, 6, 19.

(27) Grosdidier, A.; Zoete, V.; Michielin, O. *Nucleic acids research* 2011, 39, W270.

(28) Grosdidier, A.; Zoete, V.; Michielin, O. *J Comput Chem* 2011.

(29) Halgren, T. A. *J Comput Chem* 1996, 17, 490.

(30) Cho, H. S.; Mason, K.; Ramyar, K. X.; Stanley, A. M.; Gabelli, S. B.; Denney, D. W.; Leahy, D. J. *Nature* 2003, 421, 756.

(31) Lam, K. S.; Salmon, S. E.; Hersh, E. M.; Hruby, V. J.; Kazmierski, W. M.; Knapp, R. J. *Nature* 1991, 354, 82.

(32) Lehman, A.; Gholami, S.; Hahn, M.; Lam, K. *J. Comb. Chem.* 2006, 8, 562.

(33) Alves, N. J.; Mustafaoglu, N.; Bilgicer, B. *Bioconjug Chem* 2014, 25, 1198.

(34) Alves, N. J.; Mustafaoglu, N.; Bilgicer, B. *Biosensors & bioelectronics* 2013, 49, 387.

(35) Cui, H. T.; Thomas, J. D.; Burke, T. R.; Rader, C. *Journal of Biological Chemistry* 2012, 287, 28206.

(36) Doppalapudi, V. R.; Huang, J.; Liu, D. G.; Jin, P.; Liu, B.; Li, L. N.; Desharnais, J.; Hagen, C.; Levin, N. J.; Shields, M. J.; Parish, M.; Murphy, R. E.; Del Rosario, J.; Oates, B. D.; Lai, J. Y.; Matin, M. J.; Ainekulu, Z.; Bhat, A.; Bradshaw, C. W.; Woodnutt, G.; Lerner, R. A.; Lappe, R. W. *Proc. Natl. Acad. Sci. U.S.A.* 2010, 107, 22611.

(37) Wang, L. T.; Amphlett, G; Blattler, W. A.; Lambert, J. M.; Zhang, W. *Protein Sci.* 2005, 14, 2436.

(38) Panowksi, S.; Bhakta, S.; Raab, H.; Polakis, P.; Junutula, J. R. mAbs 2014, 6, 34.

(39) Jeger, S.; Zimmermann, K.; Blanc, A.; Grunberg, J.; Honer, M.; Hunziker, P.; Struthers, H.; Schibli, R. *Angewandte Chemie (International ed. in English)* 2010, 49, 9995.

(40) Strop, P.; Liu, S. H.; Dorywalska, M.; Delaria, K.; Dushin, R. G.; Tran, T. T.; Ho, W. H.; Farias, S.; Casas, M. G.; Abdiche, Y.; Zhou, D.; Chandrasekaran, R.; Samain, C.; Loo, C.; Rossi, A.; Rickert, M.; Krimm, S.; Wong, T.; Chin, S. M.; Yu, J.; Dilley, J.; Chaparro-Riggers, J.; Filzen, G. F.; O'Donnell, C. J.; Wang, F.; Myers, J. S.; Pons, J.; Shelton, D. L.; Rajpal, A. *Chemistry & biology* 2013, 20, 161.

(41) Peng, L.; Liu, R. W.; Marik, J.; Wang, X. B.; Takada, Y.; Lam, K. S. Nat. Chem. Biol. 2006, 2, 381.

Example 2

Figure 19:
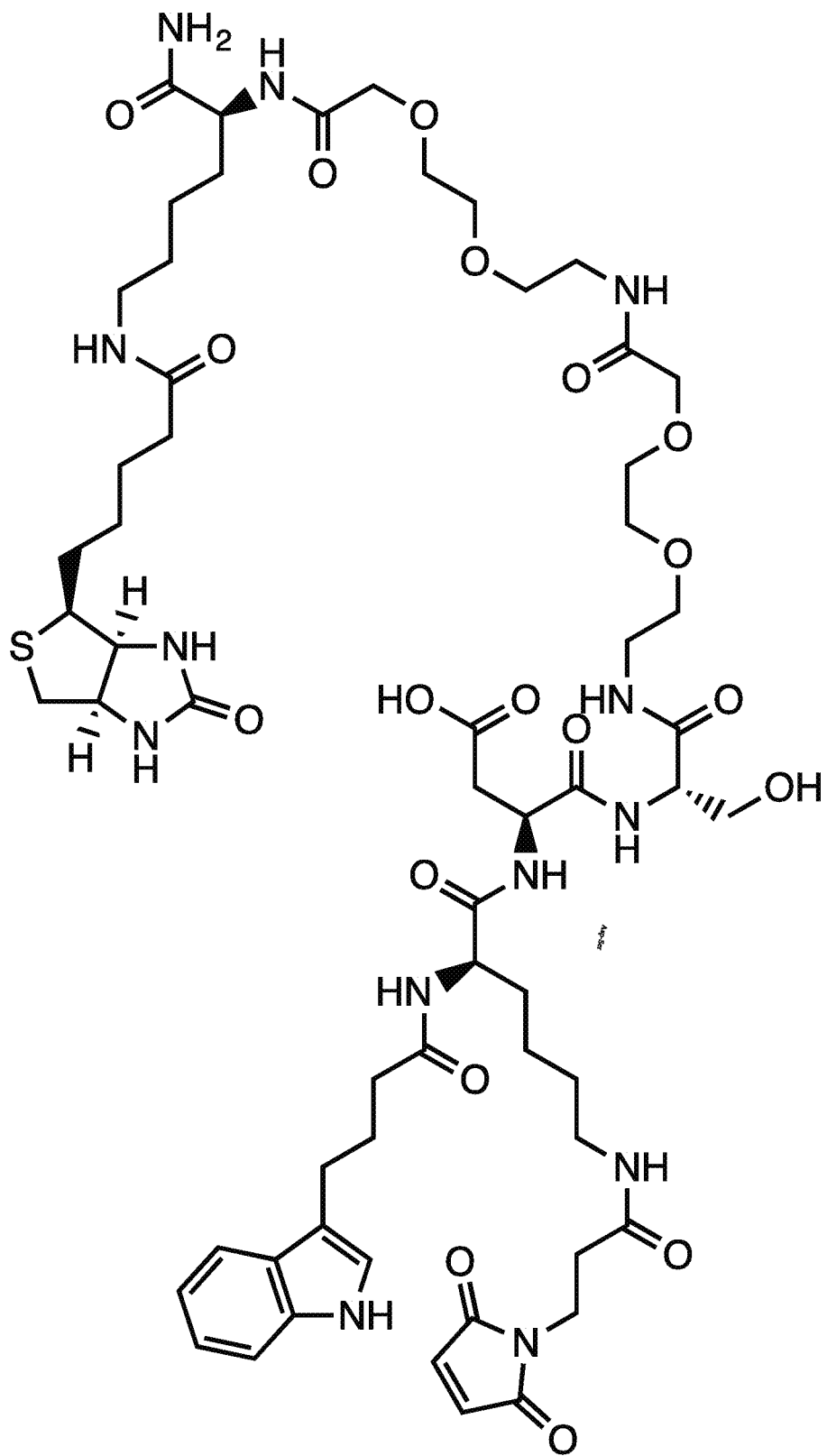
FIG. 19. Depicts a compound described herein containing a maleimide cross-linking agent, an indole targeting moiety, a linker containing a lysine-aspartate-serine amino acid sequence, and a biotin active agent.

Synthesis and Characterization of Antibody Conjugates with Maleimide Cross-Linker Trastuzumab, bevacizumab, rituximab, and nivolumab were individually conjugated to a compound containing a maleimide (M) cross-linking agent, and an aspartate-serine-containing linker (DS), herein referred to as an MDS compound (e.g., FIG. 19). The MDS compound (50 µM) was incubated with 10 µM antibody at 37° C. (pH 7.5) for 1 h in a shaking incubator. Cross-linking occurred by increasing the pH of the sample to 8.5 and incubating for 1 h at room temperature, thereby forming Trast-MDS or TMDS, BMDS, RMDS, and NMDS, respectively. In some cases, the MDS compound contained a biotinylated active agent. Samples were then dialyzed overnight at 4° C. to remove unbound peptides, with frequent water changes.

Compounds containing a maleimide cross-linking agent, an aspartate-serine-containing linker, and 1, 2, or 4 dihydroxyphenylalanine (DOPA) functional groups, herein referred to generically as MDS-DOPA and specifically as MDS-1DOPA, MDS-2DOPA, and MDS-4DOPA respectively. Successful synthesis was confirmed by mass-spectrometry (See, FIGS. 20, 22, and 32).

Trastuzumab was conjugated to MDS-1DOPA, MDS-2DOPA, and MDS-4DOPA. MDS-DOPA compounds (50 µM) were independently incubated with 10 µM trastuzumab at 37° C. (pH 7.5) for 1 h in a shaking incubator. Cross-linking occurred by increasing the pH of the sample to 8.5 and incubating for 1 h at room temperature, thereby forming Trast-MDS-1DOPA, Trast-MDS-2DOPA, and Trast-MDS-4DOPA. Samples were then dialyzed overnight at 4° C. to remove unbound peptides, with frequent water changes.

Figure 21:
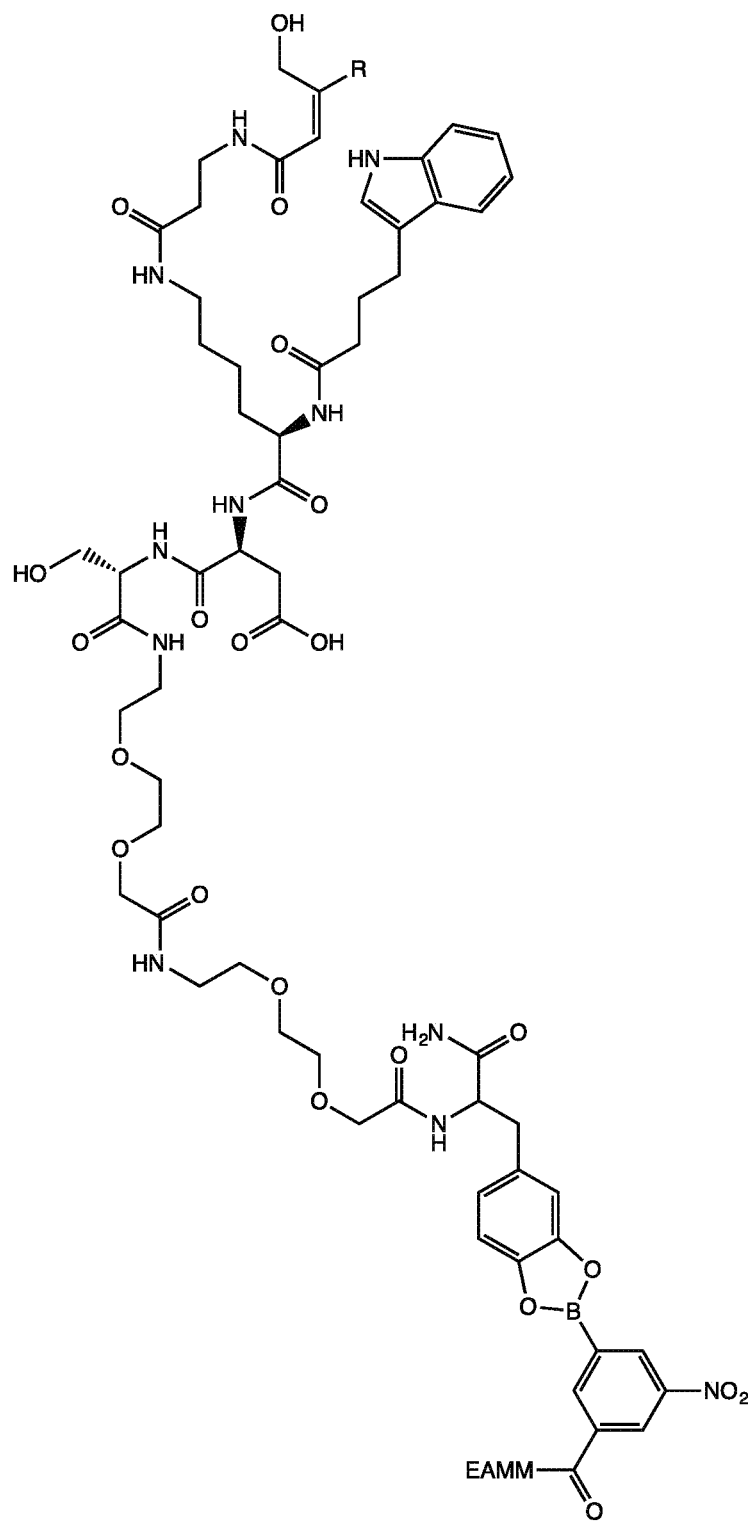
FIG. 21. Depicts a conjugate formed between the compound depicted in FIG. 20, an antibody represented by R (e.g., trastuzumab), and the boronic acid MMAE biologically active agent (e.g., Trast-MDS-DOPA-BA-MMAE).
Figure 23:
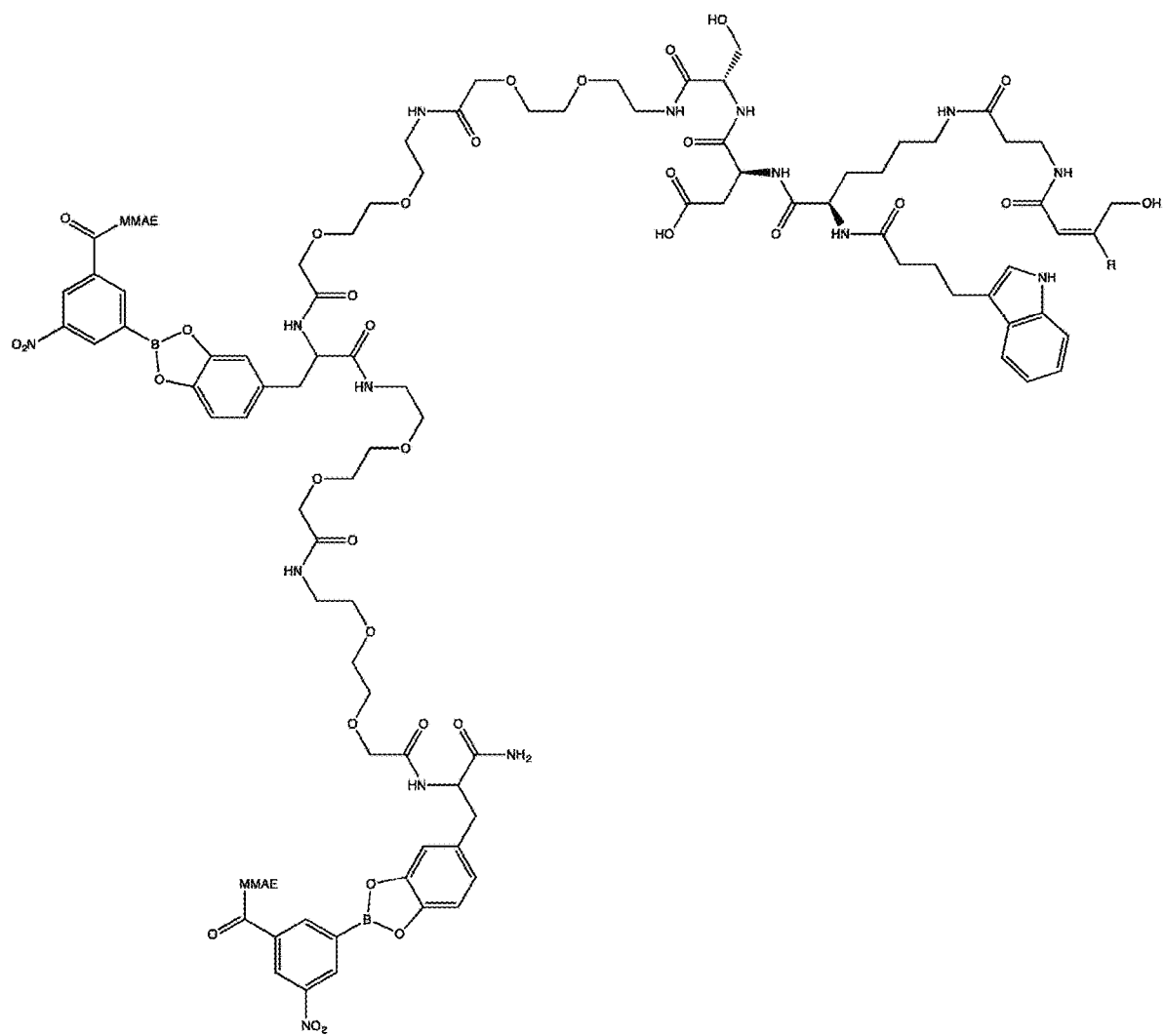
FIG. 23. Depicts a conjugate formed between the compound depicted in FIG. 22, an antibody represented by R (e.g., trastuzumab), and two boronic acid MMAE biologically active agents (e.g., Trast-MDS-2DOPA-BA-MMAE).
Figure 33:
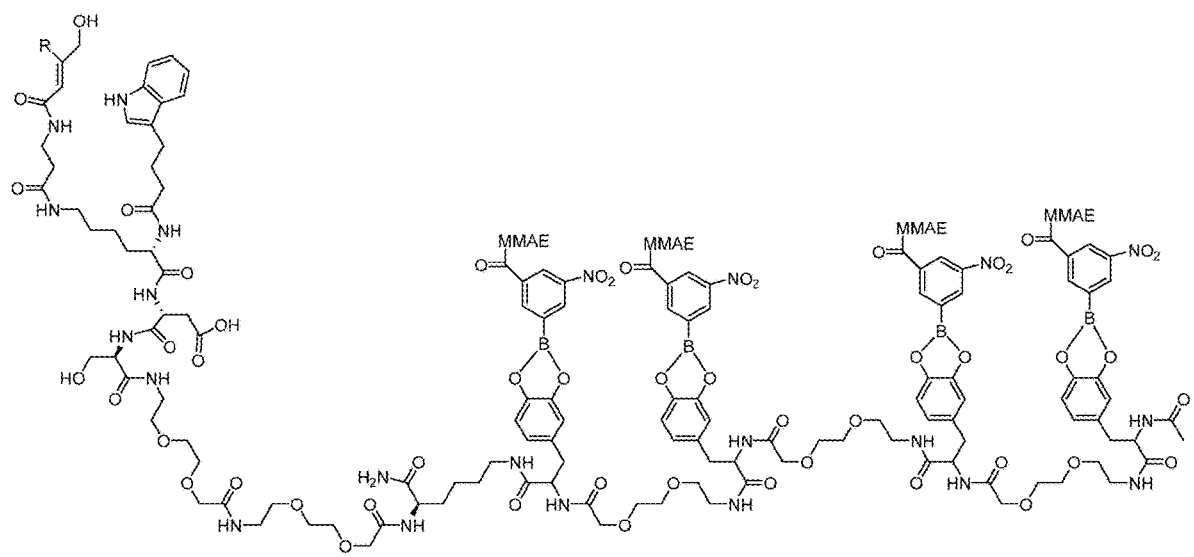
FIG. 33. Depicts a conjugate formed between the compound depicted in FIG. 32, an antibody represented by R (e.g., trastuzumab), and two boronic acid MMAE biologically active agents (e.g., Trast-MDS-4DOPA-BA-MMAE).

Trast-MDS-1(DOPA, Trast-MDS-2DOPA, and Trast-MDS-4DOPA were individually incubated with BA-MMAE peptide (FIG. 18) at 1:10 ratio at pH 8.5 for 1 hour at room temperature, thereby forming Trast-MDS-1DOPA-BA-MMAE (FIG. 21, R represents trastuzumab), Trast-MDS-2DOPA-BA-MMAE (FIG. 23, R represents trastuzumab), and Trast-MDS-4DOPA-BA-MMAE (FIG. 33, R represents trastuzumab). Samples were then dialyzed overnight at 4° C. to remove unbound peptides, with frequent water changes.

Figure 24:
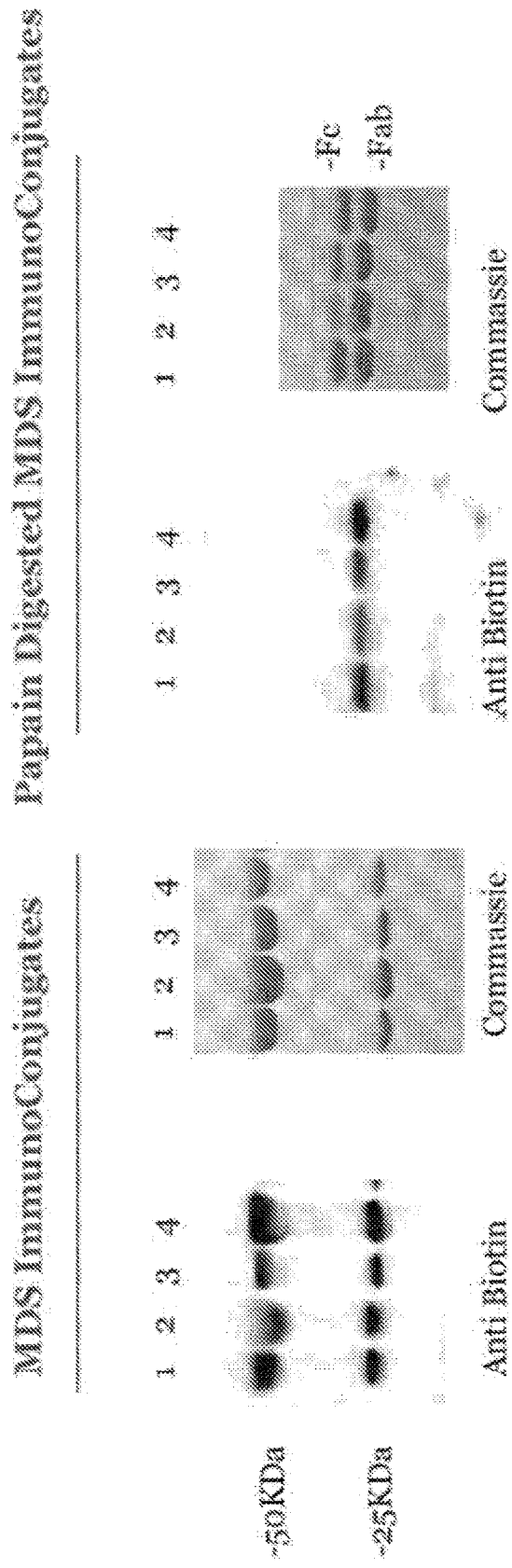
FIG. 24. (A) Western blot analysis of four different antibodies conjugated to the biotin compound depicted in FIG. 19 indicates that the compound conjugates to both the heavy and light chain of all four antibodies. (B) Western blot analysis of papain digested conjugated antibody indicates that conjugation occurs in the Fab fragment and not the Fc region. (C) Biotin quantification indicates that an approximately a 2:1 ratio of biotin to antibody in the conjugated antibody.

TMDS, BMDS, RMDS, and NMDS containing a biotin active agent were analyzed by western blotting with anti-biotin detection reagent, gel electrophoresis with coomassie blue detection reagent, and biotin quantification assay with HABA biotin complex (FIG. 24). The results indicated that the MDS compound retains site specificity and has an average biotin per antibody ratio approximately 2, whereas the positive control, NH2-reactive biotin to monoclonal antibodies, has an average of 5-10 biotin molecules conjugates to each antibody.

Figure 25:
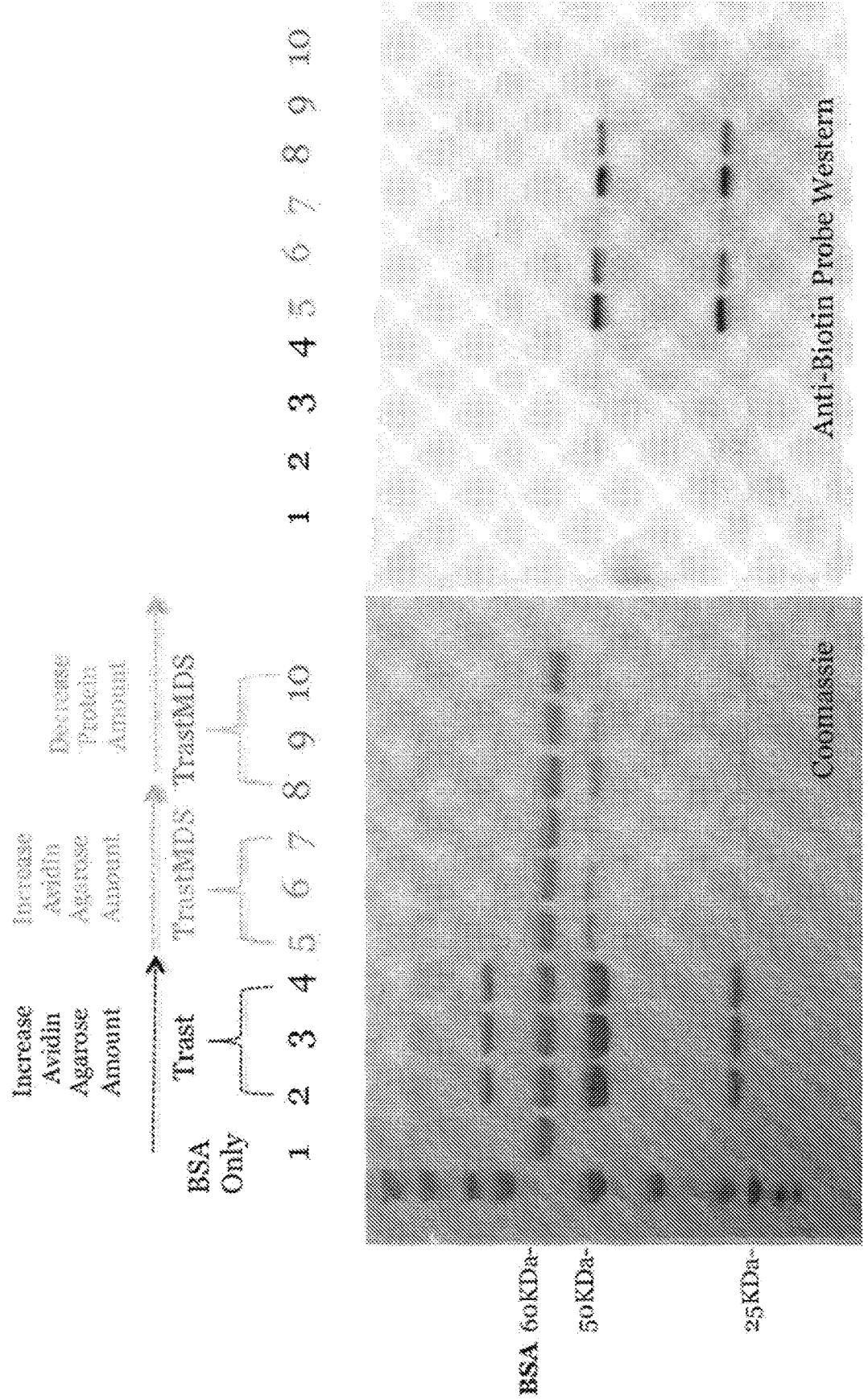
FIG. 25. Illustrates conjugation efficiency between the compound of FIG. 19 and the antibody trastuzumab (Trast-MDS). Lanes 2, 3, and 4 contain unmodified trastuzumab, and incubation with avidin agarose does not decrease the amount of antibody in solution. Lanes 5, 6, and 7 contain TrastMDS, and incubation with increasing amounts of avidin agarose decreases the amount of antibody in solution. Lanes 8, 9, and 10 contain avidin agarose and incubating the avidin agarose with decreasing amounts of TrastMDS decreases the amount of antibody in solution.

Trast-MDS was analyzed to determine the efficiency of the maleimide cross-linking reaction (FIG. 25). Conjugation efficiency is determined by comparing the band intensity between lane 7/10 and lanes 2/3/4 of FIG. 25. The results indicated that greater than 90% of the MDS compound conjugated to trastuzumab under the experimental conditions.

Figure 26:
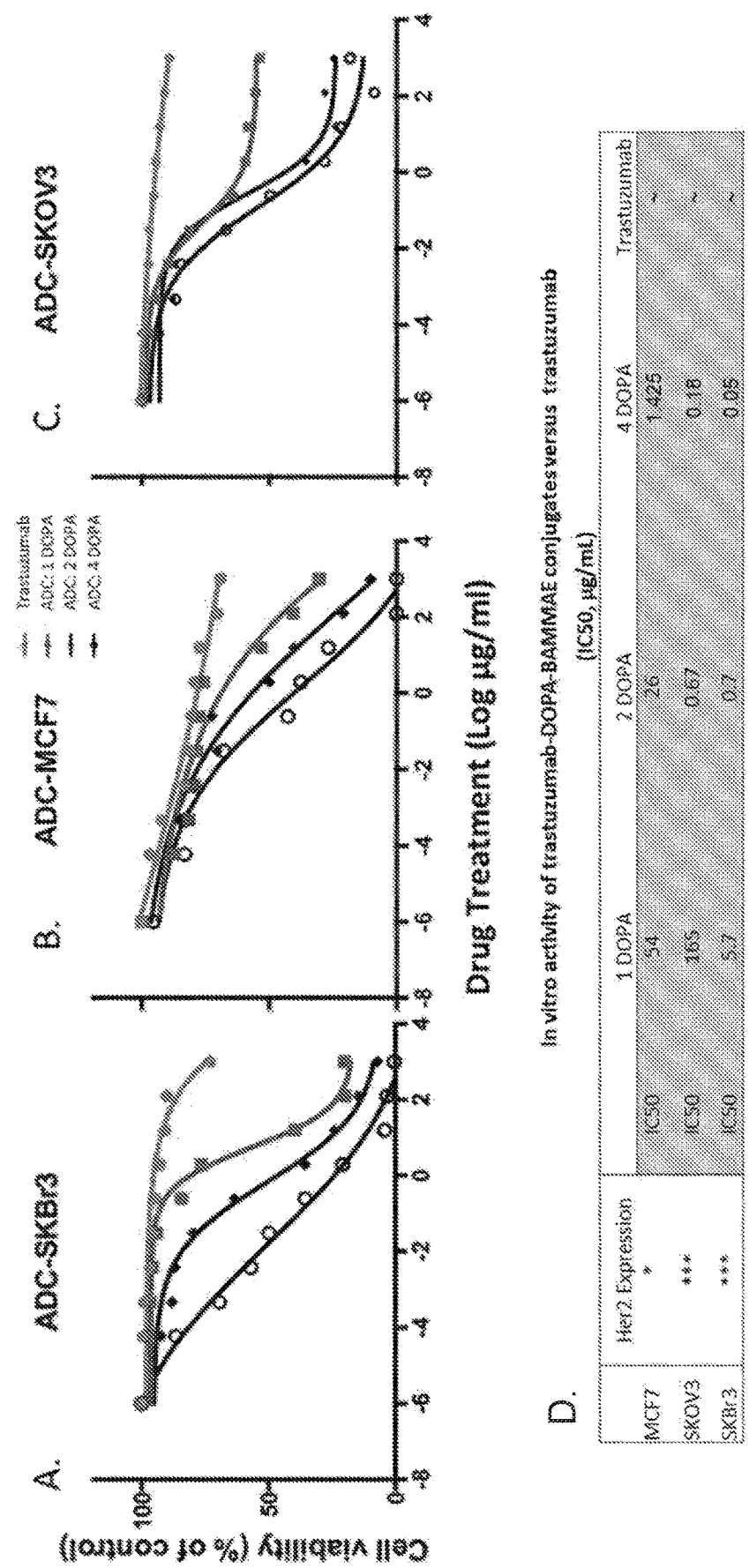
FIG. 26. Illustrates the effect of an antibody drug conjugate (ADC) compound of FIGS. 21 and 23, where R is trastuzumab, (1DOPA and 2DOPA respectively), on viability of cancer cell lines SKBr3, MCF7, and SKOV3. The 4 DOPA compound is a trastuzumab-DOPA-boronic acid MMAE compound containing four dihydroxyphenylalanine moieties, each bound to a boronic acid MMAE moiety. The column labeled trastuzumab refers to unconjugated antibody.

Trastuzumab-MDS-DOPA-BAMMAE conjugates were tested for in vitro cell killing (FIG. 26). Cells (A: SKBR3; B: MCF7; C: SKOV3) were incubated with Trast-MDS conjugated with Moronic Acid MMAE. In cell lines with HER2 triple positive expression (SKBR3 and SKOV3), decreased cell viability was seen for antibodies with MMAE conjugation. In the cell line that has lower HER2 expression (MCF7), this effect was not as pronounced. (D) $IC_{50}$ values for Trastuzumab-1/2/4DOPA-BA-MMAE and Trastuzumab alone.

Example 3

Synthesis and Characterization of Bi-Specific Antibody Conjugates

Figure 27:
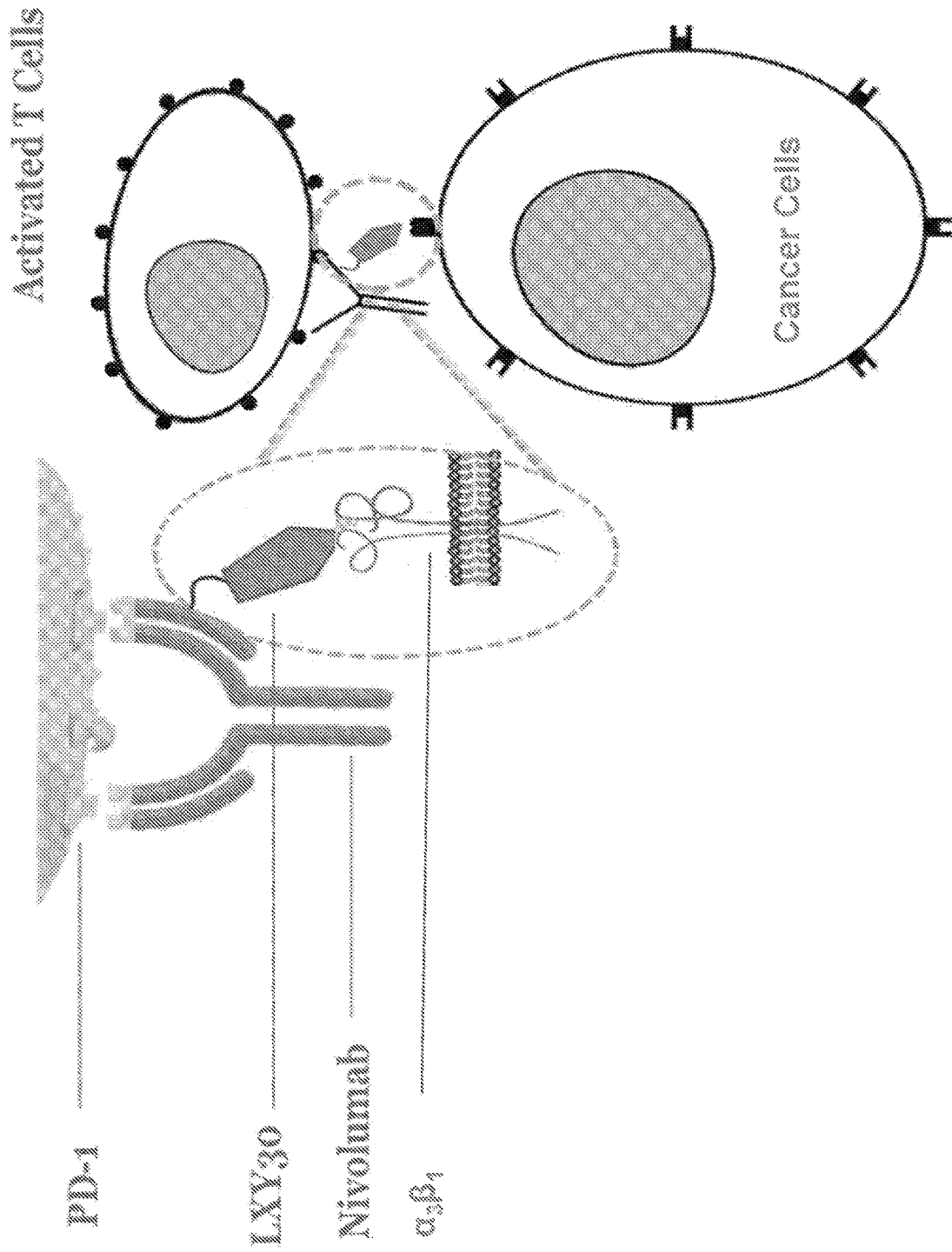
FIG. 27. Illustrates a schematic for a use of an antibody conjugate described herein for cross-linking activated T cells to target cancer cells. In the schematic depicted, the nivolumab antibody binds to and inhibits the T cell surface checkpoint antigen PD-1, and is conjugated to a compound containing: a maleimide cross-linking agent, an indole targeting moiety, a linker containing a lysine-aspartate-serine amino acid sequence, and an active agent containing an $\alpha_3\beta_1$-integrin ligand LXY30 (Xiao et al., EJNMMI Res. 2016 December; 6(1):18), Binding of the antibody to the T cell and the ligand to a target cancer cell that expresses $\alpha_3\beta_1$-integrin delivers an activated T cell to the target cancer cell, enhancing anti-tumor efficacy.

The anti-PD-1 checkpoint inhibitor antibody Nivolumab was conjugated to a cancer cell targeting ligand LXY30 to generate NMDS bi-functional antibody conjugates for enhanced effector cell killing as depicted in the schematic illustrated in FIG. 27.

NMDS preparation: MDS compound (50 µM) was incubated with 10 µM Nivolumab at 37° C. (pH 7.5) for 1 h in a shaking incubator. Cross-linking occurred by increasing the pH of the sample to 8.5 by 0.1 N ammonium solution and incubating for 1 h at room temperature, thereby generating NMDS. Samples were then dialyzed overnight at 4° C. to remove unbound peptides, with frequent water changes.

NMDS-LXY30 preparation: Biotinlyated. LXY30 is synthesized, purified and lyophilized prior to complex formation in lam lab. Bi-functional NMDS-LXY30 immunoconjugate is formed with 3:1:1 ratio between biotinlyted LXY30, Streptavidin-Alexa488 and NMDS or biotinlyted LXY30, NeutrAvidin and NMDS respectively in PBS at room temperature for 20 minutes.

Electrophoresis: 5 µg biotinylated LXY3O, NMDS, Strepavidin Alexa 488, and generated bi-functional immunoconjugate were loaded onto a 4-12% Tris-glycine gel (Life Technologies, Inc., Gaithersburg, Md.) under non-reducing condition. Bands were detected later by Coomassie blue staining and GFP fluorescent channel.

Size Exclusion Chromatography (SEC): 5 μg of each samples were subjected analysis on SEC chromatography.

Figure 28:
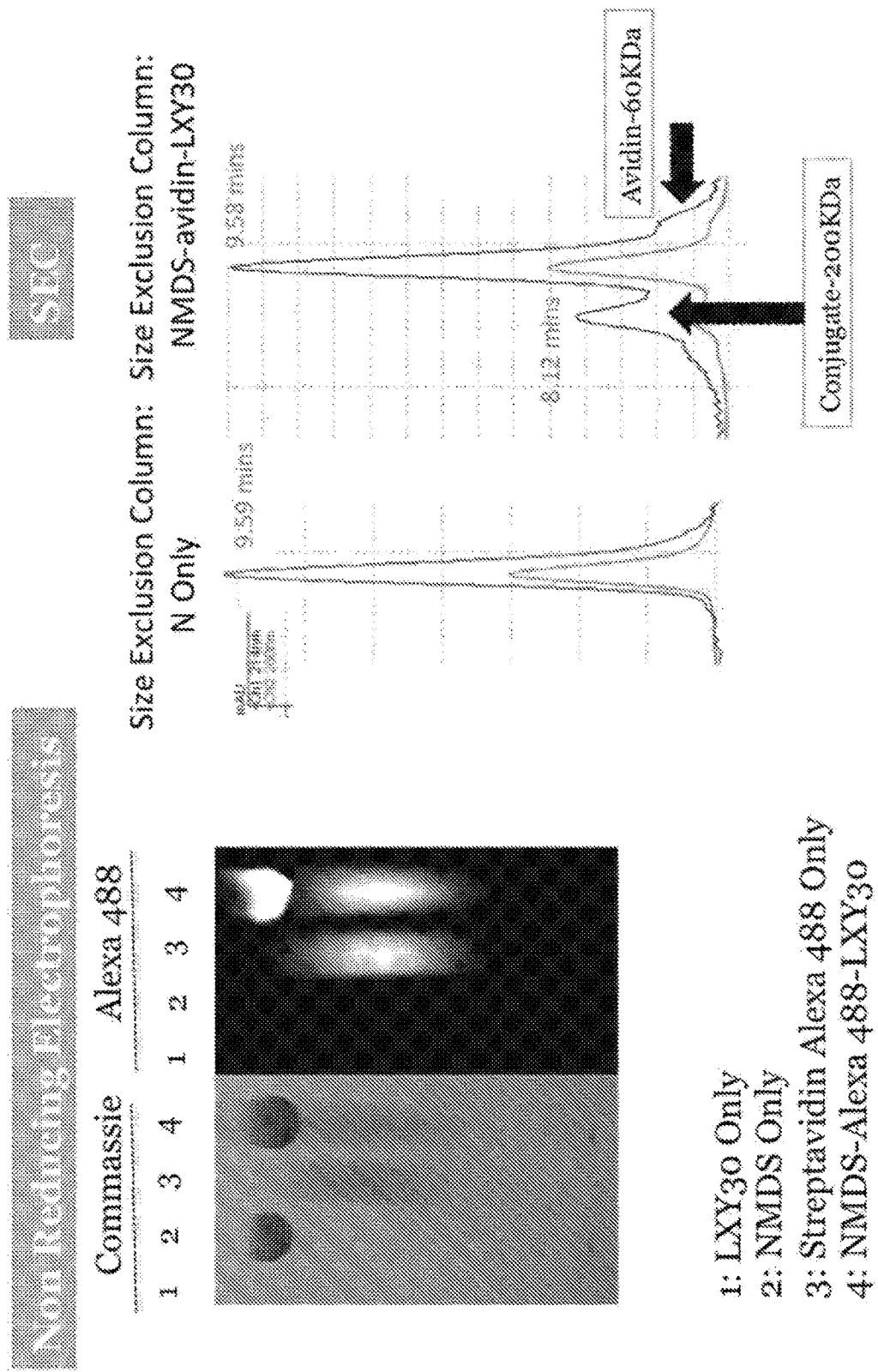
FIG. 28. Depicts successful conjugation of nivolumab (N) to a compound described herein containing a maleimide cross-linking agent (M), an indole targeting moiety, a linker containing a lysine-aspartate-serine amino acid sequence (DS), and an active agent containing a biotinylated LYX30 peptide to generate a bi-functional antibody conjugate. "NMDS Only" refers to nivolumab (N) conjugated to the compound described herein containing a maleimide cross-linking agent (M), an indole targeting moiety, and a linker containing a lysine-aspartate-serine amino acid sequence (DS). Conjugation is confirmed by gel electrophoresis and fluorescence detection of streptavidin Alexa 488 labeling, as well as size exclusion chromatography.

The results are depicted in FIG. 28. In FIG. 28, panel a., one homogeneous band under non reducing condition electrophoresis analysis in lane 4 is both detected by Coomassie blue staining and GFP fluorescent channel, demonstrating the successful generation of bi-functional NMDS-LXY30 immunoconjugate with biotinlyted LXV30, Streptavidin-Alexa488 and NMDS. In panel b. an extra peak found under size exclusion chromatography analysis with bi-functional NMDS-LXY30 sample comparing to nivolumab only. By calculating the peak retention time, the molecular size of extra peak yields 200 KDa, which is very close to the predicted MW for hi-functional NMDS-LXY30 immunoconjugate, 210 KDa. The extra shoulder peak on the bi-functional sample represents extra neutrAvidin in the complex, yields at 60 KDa.

The NMDS-LXY30 immunoconjugate was tested for tumor targeting and in vitro cell killing. SKOV3, and U87 cells were plated in 48-well plates at 20000 cells per well and allowed to adhere overnight at 37° C. in a humidified atmosphere of 5% CO2. 4% PFA were then used to fix the cells for 20 minutes at room temperature after the seeding. Cell were stained with 1 μg/ml bi-functional conjugates and followed by 500 ng GST tagged PD-1 protein for one hour at room temperature. Anti-GST horseradish peroxidase (HRP) and 3,3'-diaminobenzidine (DAB) were incubated sequentially for color development. Similar immunohistochemistry was performed on SKOV3 cells with 1 μg/ml biotin-LXY30, followed by avidin-HRP and DAB as positive control.

The results are depicted in FIG. 29. In FIG. 29, picture 1, and picture 2, the only color change is found in panel D, demonstrating that the generated hi-functional conjugates bind to PD-1 protein. The location of the color deposit demonstrates the in-functional conjugates also bind with integrin (α3β1) expressed on the target cell membrane. The table shows results of several control experiments designed to rule out false positive results from cross reactivity within the reagents. Picture 3 shows the color deposit preferentially located on the cell membrane, when target cells are incubated with biotin-LXY30 and detected with avidin HRP/DAB, as in the bi-functional conjugate experiment.

Figure 30:
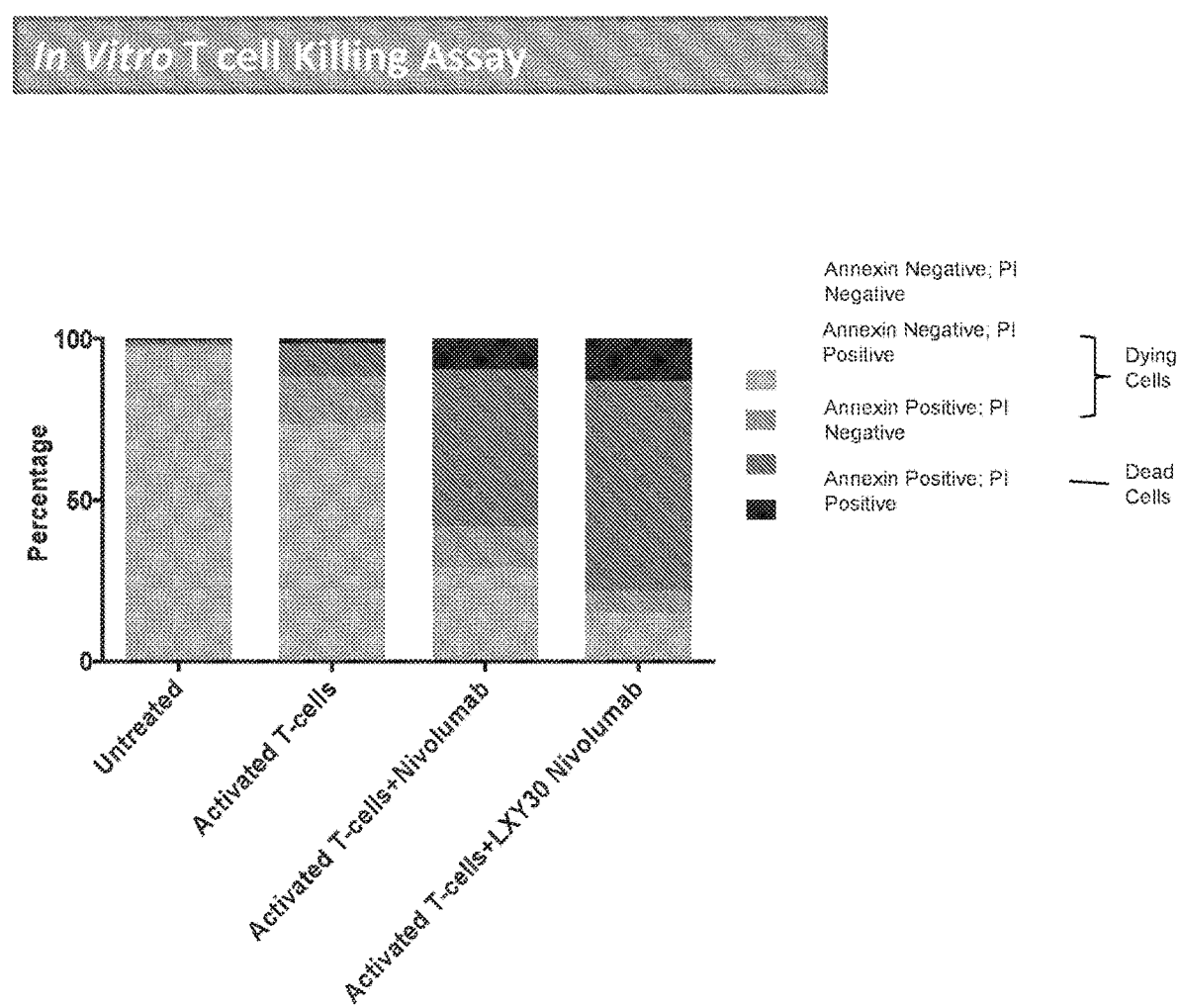
FIG. 30. Depicts results of an in vitro T cell killing assay monitored and quantified by flow cytometry. Untreated target cells (SKOV3) showed little cytotoxicity. Target cells treated with activated T cells showed a moderate amount of cell killing. The addition of the checkpoint inhibitor nivolumab increased target cell killing. The use of the bifunctional nivolumab and LXV30 conjugate NMDS-LYX30 increased the number of dead and dying target cells by 14.4% as compared to nivolumab.

In vitro cytotoxicity assays were performed to analyze the effect of the NMDS-LYX30 bi-functional immunoconjugate on T cell targeting of an α3β1 integrin expressing target cell. Target cells (SKOV3) were labeled with GFP. The labeled target cells were plated in 6-well plates at 30000 cells per well and allowed to adhere overnight at 37° C. in a humidified atmosphere of 5% CO2. PBMCs were isolated from healthy volunteer donor and activated with anti-CD3, anti-CD28 (1 ug/ml) for 72 hours prior to co-incubation with target cells. The activated PBMCs were co-cultured with target cells at E:T=10:1 ratio for 12 hours at 37° C. in a humidified atmosphere of 5% CO2 with or without 100 ng/ml immunoconjugates contained medium. At the end of the incubation, the cells were lifted by trypsin and collected from the plate. The cells were resuspended in equal volume of PBS containing 2% FBS, 1 mmol/L EDTA, Propidium iodine (PI) and Annexin V-APC for 15 minutes. The fluorescent intensity of GFP, PI and APC were recorded by a FACs machine. 10000 events of target cells were recorded by gating GFP positive channel. The percentage of live/dead cells was calculated by the different cell population containing different amount of annexin V or PI. The number of dying target cells and dead target cells were increased by 14.4% with bi-functional immunoconjugate treatment comparing to nivolumab treatment alone, indicating that the bi-functional conjugates improved anti-tumor therapeutic effect. The results are depicted in FIG. 30.

Figure 31:
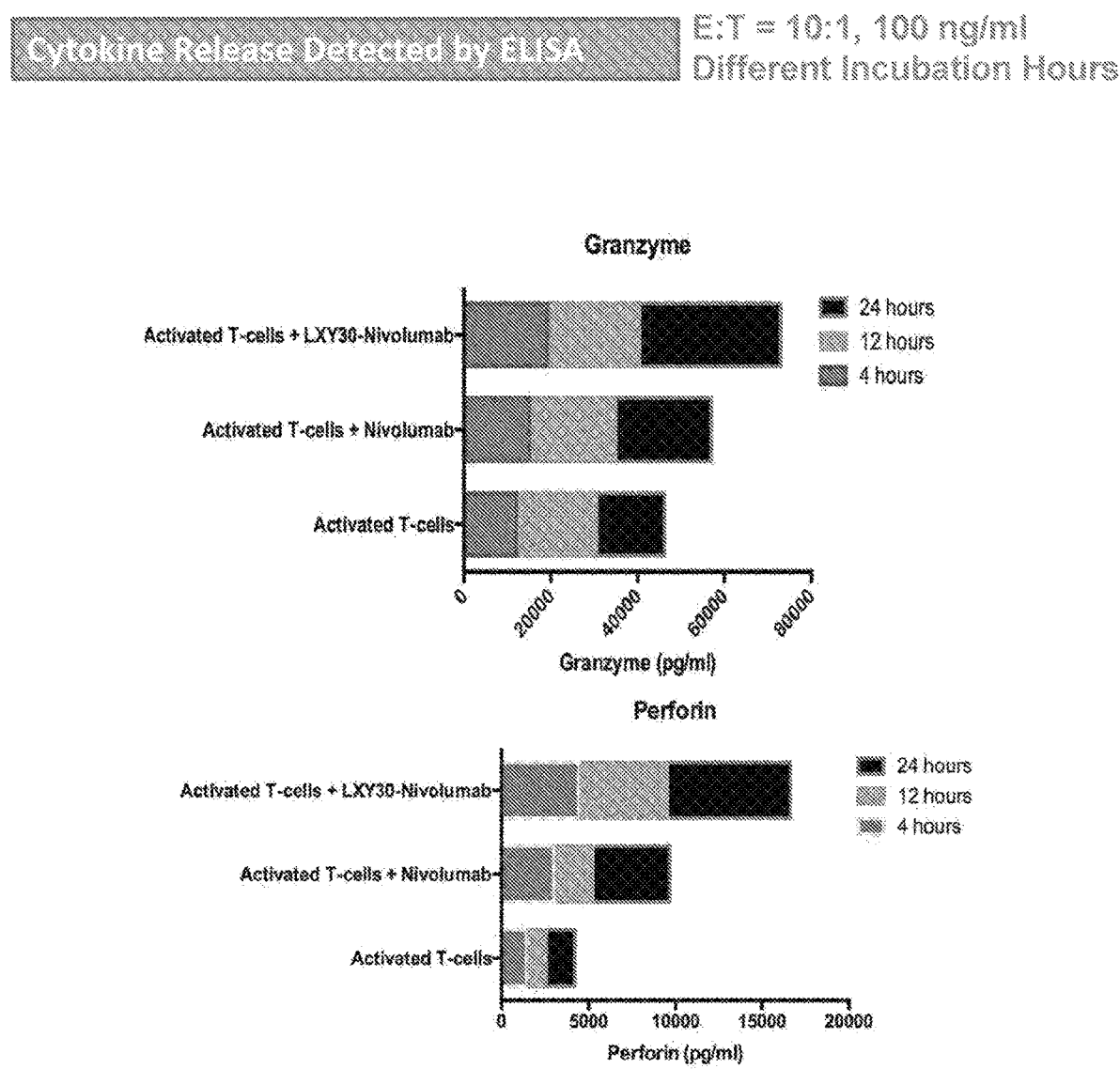
FIG. 31. Depicts the improved T cell killing of target cells with the bifunctional NMDS-LYX30 immunoconjugate as measured by ELISA detection of cytokine (top: Granzyme B, bottom: perforin) release at multiple timepoints.

Soluble perforin (Cell Sciences), and granzyme B (eBioscience) were detected from growth media at three different incubation time, 4 hours, 12 hours and 24 hours by ELBA according to the manufacture's protocols. Effector cells: target cells ratio=10:1 with or without 100 ng/ml immunoconjugates contained medium. The results are depicted in FIG. 31. Elevated perforin and granzyme B level were detected from the media at all three different time points with bi-functional incubation indicating that the improved anti-tumor therapeutic effect is due to cytotoxic T cell killing pathway.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound comprising:
   i) a targeting moiety that specifically binds a nucleotide binding pocket of an antibody;
   ii) a cross-linking agent;
   iii) an active agent or a conjugating agent; and
   iv) a linker, wherein the linter comprises an amino acid sequence, and the amino acid sequence comprises negatively charged amino acids, and wherein the linker covalently links:
      a) the targeting moiety,
      b) the cross-linking agent, and
      c) the active agent or conjugating agent.

2. The compound of claim 1, wherein the amino acid sequence has affinity for a nucleotide binding pocket of an antibody.

3. The compound of claim 1, wherein the linker comprises: i) an amino acid sequence; and ii) an ethylene glycol dimer or a PEG polymer.

4. The compound of claim 3, wherein the linker comprises a lysine-aspartate-serine amino acid sequence and the ethylene glycol dimer.

5. The compound of claim 4, wherein the compound has a formula of:

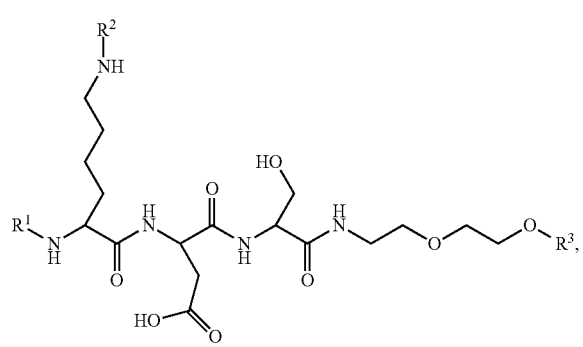

wherein, $R^1$ comprises the targeting moiety that specifically binds to the nucleotide binding pocket of an antibody;

$R^2$ comprises the cross-linking agent; and $R^3$ comprises the active agent or conjugating agent.

6. The compound of claim 1, wherein the targeting moiety that specifically binds a nucleotide binding pocket of an antibody comprises a purine or a purine analogue.

7. The compound of claim 6, wherein the purine or purine analogue comprises an indole.

8. The compound of claim 6, wherein the purine or purine analogue is indole-3-butyrate.

9. The compound of claim 1, wherein the compound comprises a formula of:

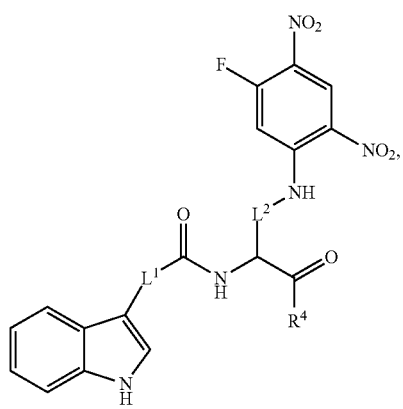

wherein $L^1$ and $L^2$ are independently a $C_1$-$C_{10}$ alkylene, and $R^4$ is represented by the following formula:

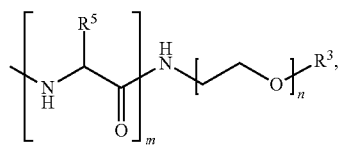

wherein $R^5$ is an amino acid side chain, m and n are independently from 1 to 10, and $R^3$ comprises the active agent or conjugating agent.

10. The compound of claim 1, wherein the compound comprises a formula of:

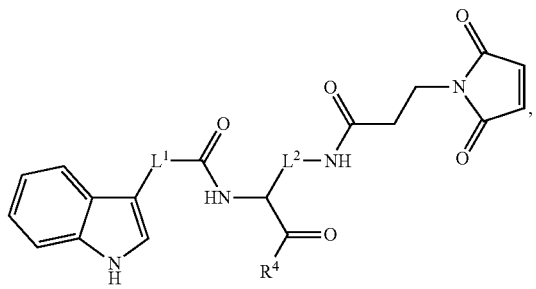

wherein $L^1$ and $L^2$ are independently a $C_1$-$C_{10}$ alkylene, and $R^4$ is represented by the following formula:

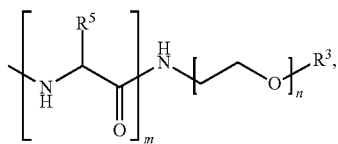

wherein $R^5$ is an amino acid side chain, m and n are independently from 1 to 10, and $R^3$ comprises the active agent or conjugating agent.

11. The compound of claim 9, wherein m is at least 2, and the at least two amino acid side chains comprise a dipeptide affinity element that increases the affinity of the targeting moiety for the nucleotide binding pocket of the antibody.

12. The compound of claim 9, wherein the compound has a formula of:

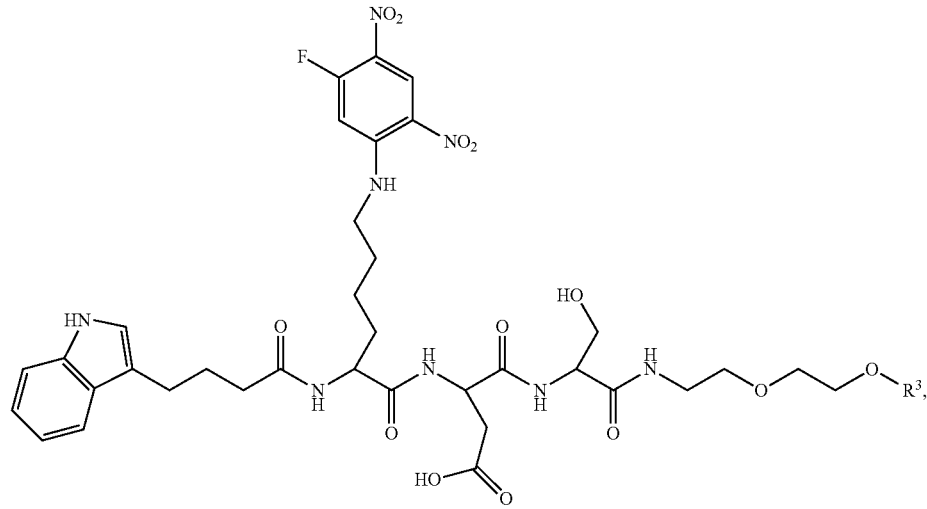

wherein $R^3$ is the active agent or conjugating agent.

13. The compound of claim 10, wherein the compound has a formula of:

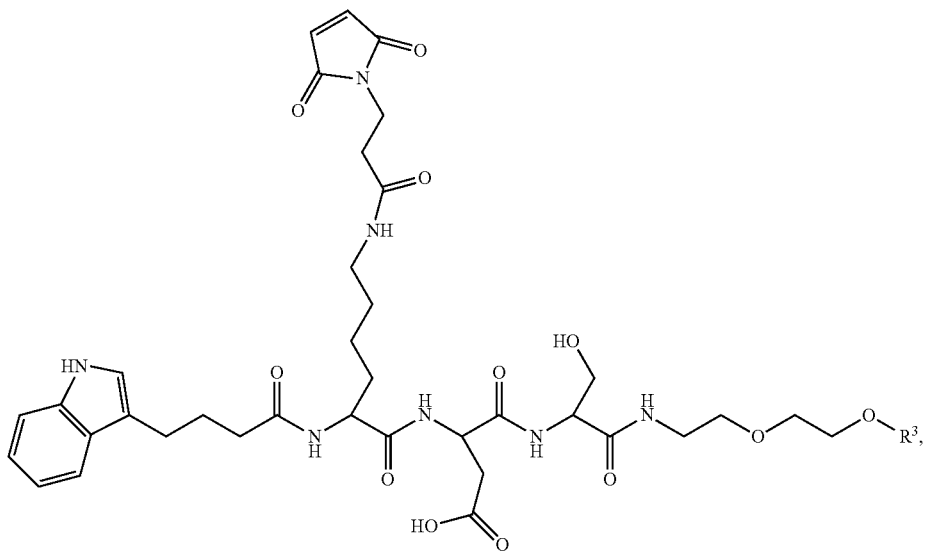
wherein R³ is the active agent or conjugating agent.
14. The compound of claim 1, wherein the compound comprises a formula of:
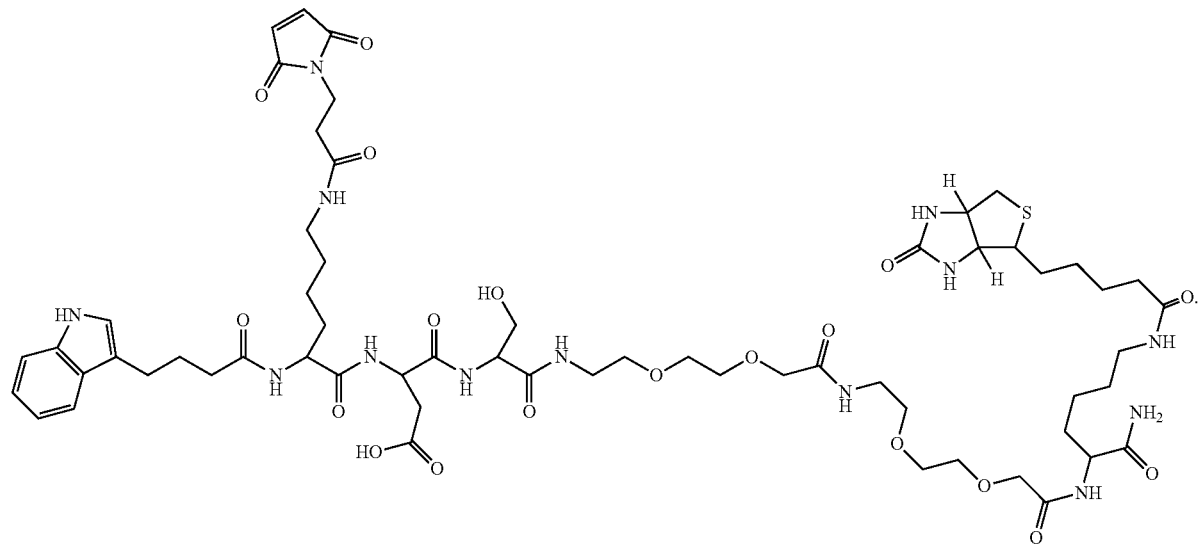 [SMILES: NC(=O)C(CCCCNC(=O)CCCCC1SCC2NC(=O)NC21)NC(=O)COCCOCCNC(=O)COCCOCCNC(=O)C(CO)NC(=O)C(CC(=O)O)NC(=O)C(CCCCNC(=O)CCN1C(=O)C=CC1=O)NC(=O)CCCc1c[nH]c2ccccc12]
15. The compound of claim 1, wherein the compound comprises a formula selected from the group consisting of:
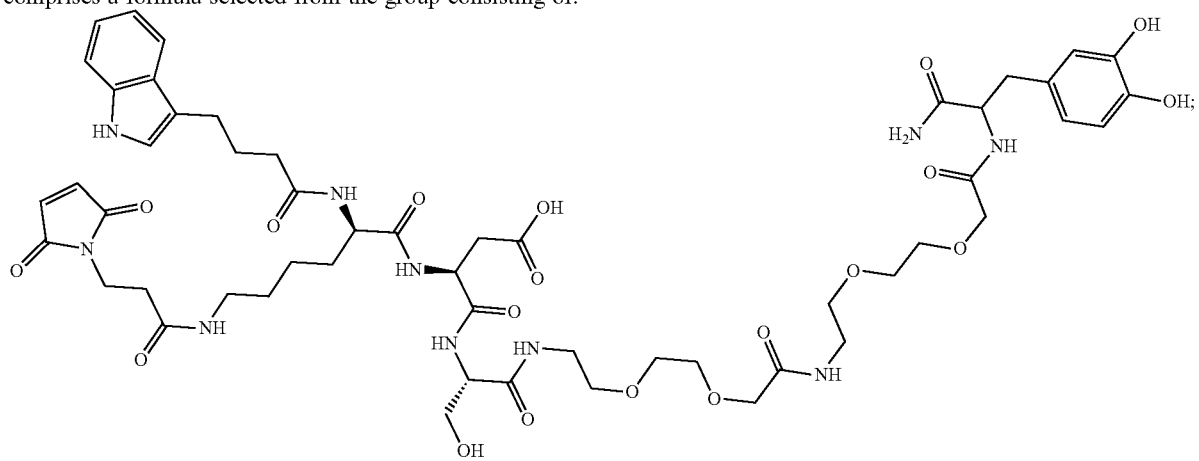

-continued

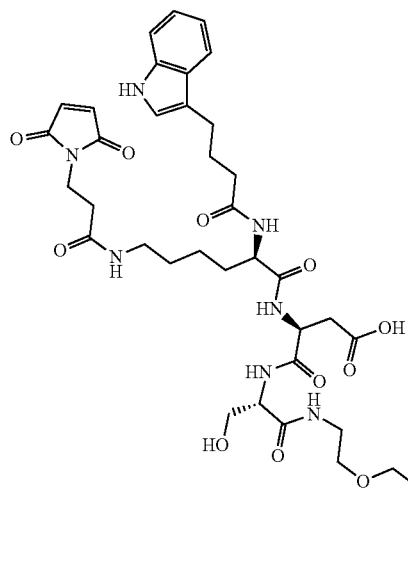

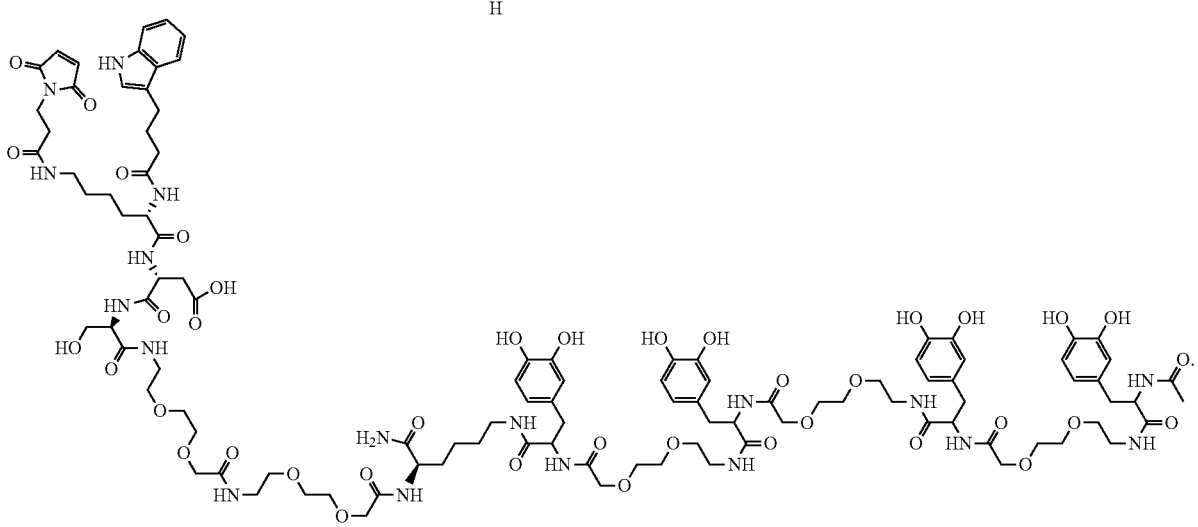

16. A method for covalently conjugating an antibody to a molecular payload, wherein the molecular payload comprises a compound of claim 1, the method comprising:
   a) forming a reaction mixture comprising the antibody and the molecular payload under conditions suitable to form a non-covalent binding interaction between a nucleotide binding pocket of the antibody and a targeting moiety of the molecular payload, wherein the reaction mixture is an aqueous solution having a pH of less than about 7.5; and
   b) raising the pH of the reaction mixture above about 8.0, under conditions suitable to form a covalent bond between the antibody and the cross-linking agent.

17. The method of claim 16, wherein the method comprises
   a) forming the reaction mixture comprising the antibody, a 5-fold molar excess of the compound of claim 12 relative to nucleotide binding pockets of the antibody, and PBS 7.0 or PBS 7.5;
   b) incubating the reaction mixture of a) for at least about 0.25 h at a temperature of from about 4° C. to about 37° C.;
   c) removing unbound compound of claim 12 by dialysis or size exclusion chromatography;
   d) raising the pH of the reaction mixture to about 8.5, under conditions suitable to form a covalent bond between the antibody and the compound of claim 12 by adding a basic solution comprising 0.1 M sodium bicarbonate pH 8.5, 0.1 N NaOH or 0.1 N NH$_4$OH; and
   e) incubating the reaction mixture of d) for at least about 0.25 h at a temperature of from about 4° C. to about 37° C.

18. The method of claim 17, wherein $R^3$ of the compound of claim 17 comprises a conjugating agent comprising an alkyne or azide and the method further comprises:
   f) introducing into the reaction mixture a copper (I) catalyst and an active agent comprising an azide or alkyne that is reactive to the alkyne or azide of the conjugating agent, thereby conjugating the active agent to the conjugating agent.

19. The method of claim 17, wherein $R^3$ of the compound of claim 17 comprises a conjugating agent comprising a 1,2-dihydroxybenzene moiety, and the method further comprises:
   f) introducing into the reaction mixture an active agent comprising a boronic acid moiety that is reactive to the 1,2-dihydroxybenzene moiety of the conjugating agent, thereby conjugating the active agent to the conjugating agent.

20. A compound of claim 1 comprising the following formula:

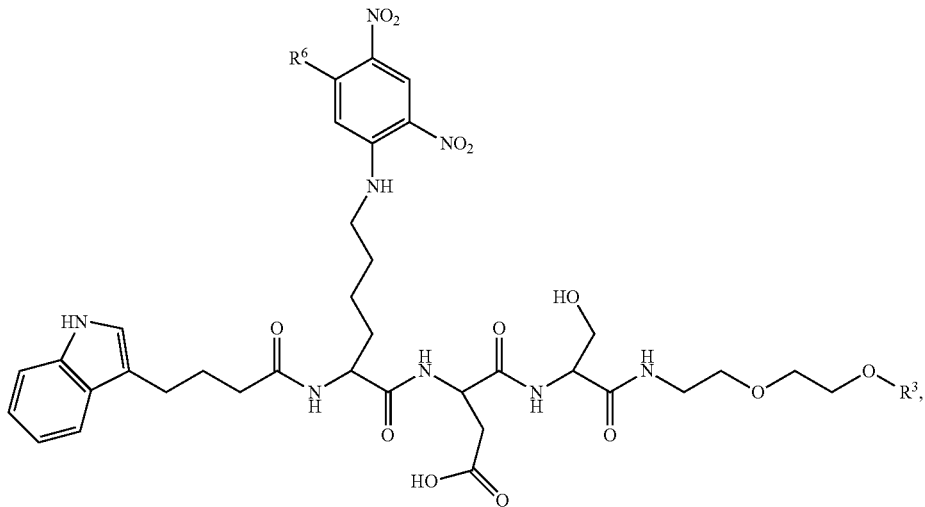

wherein $R^6$ is an antibody and $R^3$ comprises an active agent or conjugating agent.

21. A compound of claim 1 comprising the following formula:

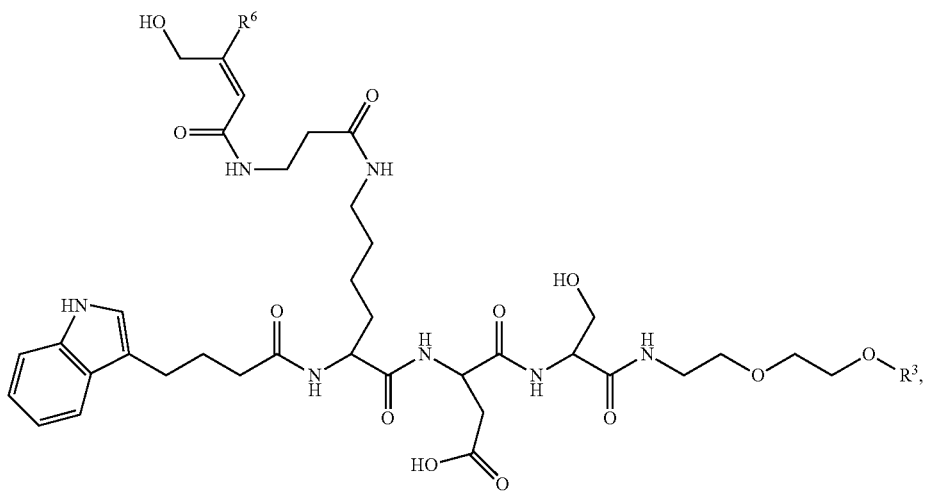

wherein $R^6$ is an antibody and $R^3$ comprises an active agent or conjugating agent.

* * * * *